(12) United States Patent
Babu et al.

(10) Patent No.: US 7,388,002 B2
(45) Date of Patent: Jun. 17, 2008

(54) NUCLEOSIDES, PREPARATION THEREOF AND USE AS INHIBITORS OF RNA VIRAL POLYMERASES

(75) Inventors: Yarlagadda S. Babu, Birmingham, AL (US); Pooran Chand, Birmingham, AL (US); Yahya El-Kattan, Hoover, AL (US); Minwan Wu, Vestavia Hills, AL (US)

(73) Assignee: BioCryst Pharmaceuticals, Inc., Birmingham, AL (US)

( * ) Notice: Subject to any disclaimer, the term of this patent is extended or adjusted under 35 U.S.C. 154(b) by 47 days.

(21) Appl. No.: 11/269,819

(22) Filed: Nov. 9, 2005

(65) Prior Publication Data

US 2006/0122391 A1 Jun. 8, 2006

Related U.S. Application Data

(63) Continuation-in-part of application No. 10/437,179, filed on May 14, 2003, now abandoned, which is a continuation-in-part of application No. PCT/US02/36621, filed on Nov. 14, 2002.

(60) Provisional application No. 60/331,322, filed on Nov. 14, 2001.

(51) Int. Cl.
C07D 473/34 (2006.01)
C07D 473/00 (2006.01)
C07F 9/6561 (2006.01)
A61K 31/675 (2006.01)
A61K 31/52 (2006.01)
A61K 31/5377 (2006.01)
A61P 31/14 (2006.01)

(52) U.S. Cl. .................... 514/81; 544/118; 544/244; 544/265; 544/276; 544/277; 514/234.2; 514/263.2; 514/263.22; 514/263.23; 514/263.38; 514/263.4

(58) Field of Classification Search ............. 514/234.2, 514/263.2, 263.22, 263.23, 263.38, 263.4, 514/81; 544/276, 277, 244, 265, 118
See application file for complete search history.

(56) References Cited

U.S. PATENT DOCUMENTS

| | | | | |
|---|---|---|---|---|
| 5,650,510 | A * | 7/1997 | Webb et al. | 544/244 |
| 6,057,305 | A * | 5/2000 | Holy et al. | 514/81 |
| 2004/0014722 | A1* | 1/2004 | Babu et al. | 514/81 |
| 2005/0009043 | A1* | 1/2005 | Becker et al. | 435/6 |
| 2005/0033051 | A1* | 2/2005 | Babu et al. | 544/243 |
| 2005/0059637 | A1* | 3/2005 | Krawczyk | 514/81 |
| 2005/0080053 | A1* | 4/2005 | Babu et al. | 514/81 |
| 2008/0008682 | A1* | 1/2008 | Chong et al. | 514/81 |

FOREIGN PATENT DOCUMENTS

| | | |
|---|---|---|
| EP | 0 206 459 A2 | 12/1986 |
| EP | 0 269 947 A1 | 6/1988 |
| WO | WO 2004106350 A1 * | 12/2004 |

OTHER PUBLICATIONS

PERBOST M. Nucleosides & nucleotides 1992, vol. 11, No. 8, pp. 1529-1537.*
He, et al. Tetrahedron 65 8505 (2005).*
Schaeffer, J. Med. Chem 15, 456 (1972).*
Wu et al, Nucleosides, Nucleotides & Nucleic Acids (Oct. 2005), 24(10-12), 1543-1568.*
Wu et al, Nucleosides, Nucleotides & Nucleic Acids (Oct. 2005), 24(10-12), 1597-1611.*
Wu et al, Nucelosides, Nucleotides & Nucleic Acids (Oct. 2005), 24(10-12), 1569-1585.*
"Synthesis of Acyclic Nucleoside and Nucleotide Analogues from Amino Acids: A Convenient Approach to a PMEA-PMPA Hybrid" Jeffrey et al., Tetrahedron vol. 56, No. 29, Jul. 14, 2000, pp. 5077-5083.
"Synthesis and Antiviral Activity of Methyl Derivatives of 9-[2-(Phosphonomethoxy)ethyl]guanine" Yu et al., Journal of Medicinal Chemistry, vol. 35, No. 16, Aug. 17, 1992, pp. 2958-2969.
"Acyclic Purine Phosphonate Analogues as Antiviral Agents. Synthesis and Structure-Activity Relationships" Kim et al. Journal of Medicinal Chemistry vol. 33, No. 4, Apr. 1990, pp. 1207-1213.
XP-002116171 "Acyclic nucleotide analogs. IV. Phosphonylmethoxyalkyl and Phosphonylalkyl Derivatives of Adenine" Rosenberg et al., Collection of Czechoslovak Chemical Communications, Institute of Organic Chemistry and Biochemistry, vol. 53, No. 11B, 1988, pp. 2753-2777.

* cited by examiner

Primary Examiner—Mark L Berch
(74) Attorney, Agent, or Firm—Connolly Bove Lodge & Hutz LLP

(57) ABSTRACT

Compounds represented by the formula:

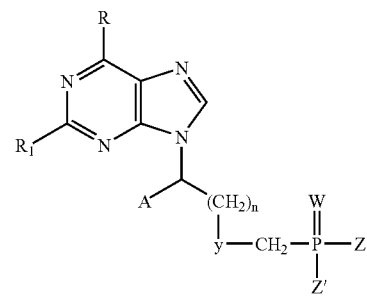

(I)

A is $(CH_2)_nR_2$, $-CH=CH_2$, $CH_2-CH=CH_2$, $O(CH_2)_nR_2$, $CH(OH)CH_3$, $CH(OH)CH_2OH$, $CH_2-CH(OH)CH_3$, $CH_2CH(OH)CH_2OH$, or $CH(OH)CH(OH)CH_3$,
$R, R_1$ individually is H, $NH_2OH$, Cl, Br, I, aryl, substituted aryl, heterocycle, $NR_3R_4$, $OR_3$ or $SR_3$,
$R_2$ is H, OH, F, $N_3$, $NH_2$, $CO_2H$, SH, alkyl, substituted alkyl, S-alkyl, O-acyl, $CONH_2$, or CONH-alkyl,
n is 1-3,
y is O, S or NH,
W is O or S,
Z, Z' individually is $OR_3$, $OR_4$, $O(CH_2)_m-O-(CH_2)_xCH_3$, NH—CH (alkyl)$CO_2R_3$, alkyl, substituted alkyl, $OCH_2CH_2S-C(O)CH_3$, $OCH_2CH_2S-C(O)CH(CH_3)_2$, $OCH_2CH_2S-C(O)C(CH_3)_3$, $OCH_2CH_2-SC(O)$aryl, $OCH_2CH_2-S-S-OCH_2CH_2OH$, $OCH_2OC(O)C(CH_3)_3$, $OCH_2-O-C(O)OCH(CH_3)_2$, or $OCH_2-O-C(O)CH(CH_3)_2$
$R_3$, $R_4$ individually is H, alkyl, substituted alkyl, aryl, or substituted aryl;

Both $R_3$ and $R_4$ can form a monocyclic ring of 4-7 atoms with N or optionally a further heteroatom in the ring;
m is 1-3,
x is 0-19;
and pharmaceutically acceptable salts thereof and prodrugs thereof are provided.

16 Claims, No Drawings

NUCLEOSIDES, PREPARATION THEREOF AND USE AS INHIBITORS OF RNA VIRAL POLYMERASES

CROSS REFERENCES TO RELATED APPLICATIONS

This application is a continuation-in-part of application Ser. No. 10/437,179 filed May 14, 2003 now abandoned, entitled NUCLEOSIDES, PREPARATION THEREOF AND USE AS INHIBITORS OF RNA VIRAL POLYMERASES, which in turn is a continuation-in-part of PCT/US02/36621, which designated the US, filed Nov. 14, 2001, and which in turn claims the benefit of Ser. No. 60/331,322, filed Nov. 14, 2001; entire disclosures of which are incorporated herein by reference.

TECHNICAL FIELD

The present disclosure relates to certain nucleosides and particularly to nucleosides that are useful as inhibitors of viral RNA polymerases such as, but not limited to, hepatitis B, hepatitis C, Polio, Coxsackie A and B, Rhino, Echo, small pox, Ebola, and West Nile virus polymerases.

The present disclosure also relates to pharmaceutical compositions comprising the composition of the present disclosure, as well as methods of using the compounds in inhibiting viral RNA polymerases and treating patients suffering from diseases caused by various RNA viruses.

The present disclosure also relates to a method for producing the compounds of the present invention.

BACKGROUND

Hepatitis C virus (HCV), as a particular example of an RNA virus, has infected an estimated 170 million people worldwide, leading to a major health crisis as a result of the disease. Indeed, during the next few years the number of deaths from HCV-related liver disease and hepatocellular carcinoma may overtake those caused by AIDS. Egypt is the hardest hit country in the world, with 23% of the population estimated to be carrying the virus; whereas, in the USA the prevalence of chronic infections has recently been determined to be around 1.87% (2.7 million persons). HCV infections become chronic in about 50% of cases. Of these, about 20% develop liver cirrhosis that can lead to liver failure, including hepatocellular carcinoma.

The NS5B region of HCV encodes a 65 KDa RNA-dependent RNA polymerase (RdRp) thought to be responsible for viral genome replication. RdRps function as the catalytic subunit of the viral replicase required for the replication of all positive-strand viruses. The NS5B protein has been well characterized, shown to possess the conserved GDD motif of RNA-dependent RNA polymerases and in vitro assay systems have been reported. Cellular localization studies revealed that NS5B is membrane-associated in the endoplasmic reticulum like NS5A, suggesting that those two proteins may remain associated with one another after proteolytic processing. Additional evidence suggests that NS3, NS4A and NS5B interact with each other to form a complex that function as part of the replication machinery of HCV.

The X-ray crystal structure of NS5B apoenzyme has now been determined and three very recent publications describe the unusual shape of the molecule. This unique shape for a polymerase, resembling a flat sphere, is attributed to extensive interactions between the fingers and thumb subdomains in such a way that the active site is completely encircled, forming a cavity 15 Å across and 20 Å deep. Modeling studies showed that the NS5B apoenzyme can accommodate the template-primer without large movement of the subdomains, suggesting that the structure is preserved during the polymerization reaction.

There are only a few reports of weak inhibitors of the polymerase. These include some nucleotide analogues, gliotoxin and the natural product cerulenin.

Accordingly, it would be desirable to develop inhibitors of RNA viral polymerases.

SUMMARY

The present disclosure relates to novel compounds and in particular, compounds that are represented by the formula:

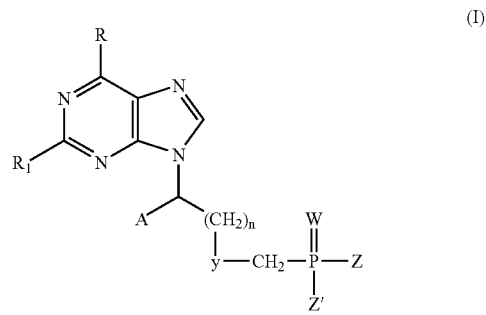

(I)

A is $(CH_2)_nR_2$, $-CH=CH_2$, $CH_2-CH=CH_2$, $O(CH_2)_nR_2$, $CH(OH)CH_3$, $CH(OH)CH_2OH$, $CH_2-CH(OH)CH_3$, $CH_2CH(OH)CH_2OH$, or $CH(OH)CH(OH)CH_3$, $R, R_1$ individually is H, $NH_2OH$, Cl, Br, I, aryl, substituted aryl, heterocycle, $NR_3R_4$, $OR_3$, or $SR_3$, $R_2$ is H, OH, F, $N_3$, $NH_2$, $CO_2H$, SH, alkyl, substituted alkyl, S-alkyl, O-acyl, $CONH_2$, or CONH-alkyl, n is 1-3, y is O, S or NH, W is O or S, Z, Z' individually is $OR_3$, $OR_4$, $O(CH_2)_m-O-(CH_2)_xCH_3$, $NH-CH(alkyl)CO_2R_3$, alkyl, substituted alkyl, $OCH_2CH_2S-C(O)CH_3$, $OCH_2CH_2S-C(O)CH(CH_3)_2$, $OCH_2CH_2S-C(O)C(CH_3)_3$, $OCH_2CH_2-SC(O)aryl$, $OCH_2CH_2-S-S-OCH_2CH_2OH$, $OCH_2OC(O)(CH_3)_3$, $OCH_2-O-C(O)OCH(CH_3)_2$, or $OCH_2-O-C(O)CH(CH_3)_2$, $R_3$, $R_4$ individually is H, alkyl, substituted alkyl, aryl, or substituted aryl, Both $R_3$ and $R_4$ can form a monocyclic ring of 4-7 atoms with N and optionally other heteroatom in the ring, m is 1-3, x is 0-19;

and pharmaceutically acceptable salts thereof and prodrugs thereof.

The following formulae II to VIII further illustrate, some purine derivatives according to the present disclosure:

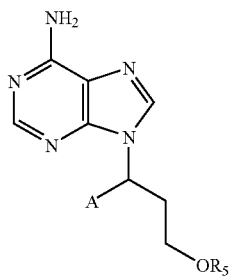

R$_5$ is H,

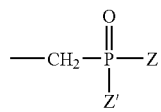

A is CH$_2$OH, CH$_2$OCH$_3$, CH$_2$N$_3$, CH$_2$NH$_2$, CH(OH)CH$_3$, CH$_2$F, or =CH$_2$,

Z, Z' individually is OR$_3$, OR$_4$, O(CH$_2$)$_m$—O—(CH$_2$)$_x$CH$_3$, NH—CH(alkyl)CO$_2$R$_3$, alkyl, substituted alkyl, OCH$_2$CH$_2$S—C(O)CH$_3$, OCH$_2$CH$_2$S—C(O)CH(CH$_3$)$_2$, OCH$_2$CH$_2$S—C(O)C(CH$_3$)$_3$, OCH$_2$CH$_2$—SC(O)aryl, OCH$_2$CH$_2$—S—S—OCH$_2$CH$_2$OH, OCH$_2$OC(O)C(CH$_3$)$_3$, OCH$_2$—O—C(O)OCH(CH$_3$)$_2$, or OCH$_2$—O—C(O)CH(CH$_3$)$_2$, R$_3$, R$_4$ individually is H, alkyl, substituted alkyl, aryl, or substituted aryl, Both R$_3$ and R$_4$ can form a monocyclic ring of 4-7 atoms with N or other heteroatom in the ring, m is 1-3, x is 0-19;

and pharmaceutically acceptable salts thereof and prodrugs thereof.

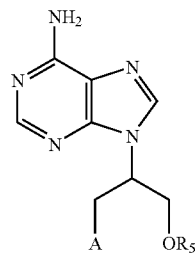

R$_5$ is H,

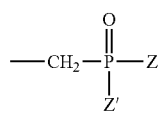

A is CH$_2$OH, CH$_2$N$_3$, CH$_2$NH$_2$, CH$_2$OCH$_3$, CH$_3$, or CH(OH)CH$_3$,

Z, Z' individually is OR$_3$, OR$_4$, O(CH$_2$)$_m$—O—(CH$_2$)$_x$CH$_3$, NH—CH(alkyl)CO$_2$R$_3$, alkyl, substituted alkyl, OCH$_2$CH$_2$S—C(O)CH$_3$, OCH$_2$CH$_2$S—C(O)CH(CH$_3$)$_2$, OCH$_2$CH$_2$S—C(O)C(CH$_3$)$_3$, OCH$_2$CH$_2$—SC(O)aryl, OCH$_2$CH$_2$—S—S—OCH$_2$CH$_2$OH, OCH$_2$OC(O)C(CH$_3$)$_3$, OCH$_2$—O—C(O)OCH(CH$_3$)$_2$, or OCH$_2$—O—C(O)CH(CH$_3$)$_2$, R$_3$, R$_4$ individually is H, alkyl, substituted alkyl, aryl, or substituted aryl, Both R$_3$ and R$_4$ can form a ring of 4-7 atoms with N or other heteroatom in the ring, m is 1-3, x is 0-19;

and pharmaceutically acceptable salts thereof and prodrugs thereof.

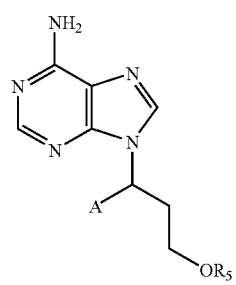

R$_5$=H,

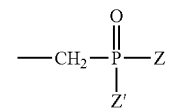

A is CH$_2$OH, CH$_2$OCH$_3$, CH$_2$N$_3$, CH$_2$NH$_2$, CH(OH)CH$_3$, CH$_2$F, =CH$_2$, or CH$_2$CH$_2$OH

Z,Z' individually is OH, —O—CH$_2$OC(O)C(CH$_3$)$_3$, or —O—CH$_2$OC(O)OCH(CH$_3$)$_2$, and pharmaceutically acceptable salts thereof and prodrugs thereof.

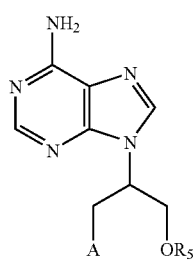

R$_5$ is H,

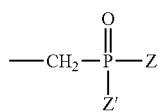

A is $CH_2OH$, $CH_2N_3$, $CH_2NH_2$, $CH_2OCH_3$, $CH_3$, or $CH(OH)CH_3$,

Z,Z' individually is OH, —O—$CH_2$—OC(O)C$(CH_3)_2$, or $OCH_2OC(O)OCH(CH_3)_2$, and pharmaceutically acceptable salts thereof and prodrugs thereof.

$OCH_2CH_2$—S—S—$OCH_2CH_2OH$, $OCH_2OC(O)C(CH_3)_3$, $OCH_2$—O—C(O)OCH$(CH_3)_2$, or $OCH_2$—O—C(O)CH$(CH_3)_2$, $R_3$, $R_4$ individually is H, alkyl, substituted alkyl, aryl, or substituted aryl, Both $R_3$ and $R_4$ can form a ring of 4-7 atoms with N or other heteroatom in the ring m is 1-3, x is 0-19;

and pharmaceutically acceptable salts thereof and prodrugs thereof.

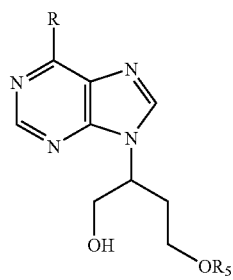
(VI)

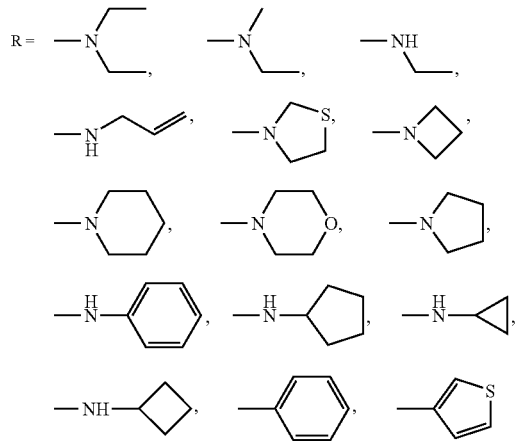

$R_5$ is H,

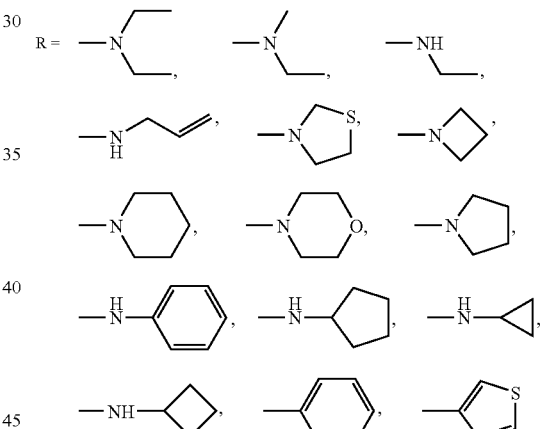
(VII)

$R_5$ is H,

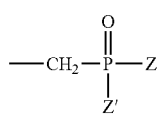

Z, Z' individually is $OR_3$, $OR_4$, O$(CH_2)_m$—O—$(CH_2)_xCH_3$, NH—CH(alkyl)CO$_2R_3$, alkyl, substituted alkyl, $OCH_2CH_2S$—C(O)CH$_3$, $OCH_2CH_2S$—C(O)CH$(CH_3)_2$, $OCH_2CH_2S$—C(O)C$(CH_3)_3$, $OCH_2CH_2$—SC(O)aryl,

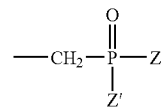

Z, Z' individually is OH, —O—$CH_2OC(O)C(CH_3)_3$, or —$OCH_2OC(O)OCH(CH_3)_2$;

and pharmaceutically acceptable salts thereof and prodrugs thereof.

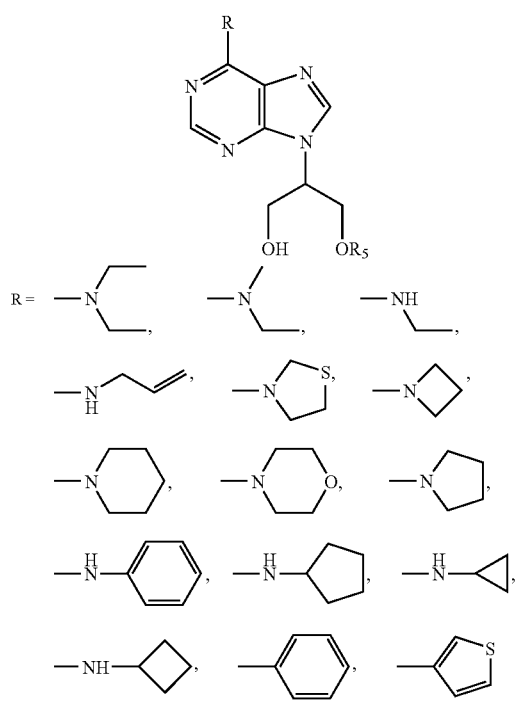

(VIII)

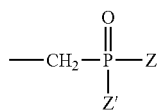

$R_5$=H,

—CH$_2$—P(=O)(Z')—Z

Z, Z' individually is OH, —O—CH$_2$OC(O)C(CH$_3$)$_3$, or —OCH$_2$OC(O)OCH(CH$_3$)$_2$;

and pharmaceutically acceptable salts thereof and prodrugs thereof.

Another aspect of the present disclosure relates to pharmaceutical composition containing at least one of the above-disclosed compounds.

The present disclosure also relates to a method for inhibiting RNA polymerases in a patient by administering to the patient at least one of the above-disclosed compounds in an amount sufficient to inhibit viral RNA polymerases, such as HCV, small pox, Ebola virus, and West Nile virus.

The present disclosure is also concerned with methods of using the compounds of the present invention in treating a patient suffering from RNA viral infections such as HCV, HBV, small pox, Ebola, polio, West Nile, and Rhino viral infection by administering to the patient an effective amount of at least one of the above-disclosed compounds.

Still other objects and advantages of the present disclosure will become readily apparent by those skilled in art from the following detailed description, wherein it is shown and described preferred embodiments of the disclosure, simply by way of illustration of the best mode contemplated of carrying out the disclosure. As will be realized, the disclosure is capable of other and different embodiments, and its several details are capable of modifications in various obvious aspects, without departing from the disclosure. Accordingly, the description to be regarded as illustrative in nature and not as restrictive.

BEST AND VARIOUS MODES

In particular, the present disclosure relates to compounds represented by the formula:

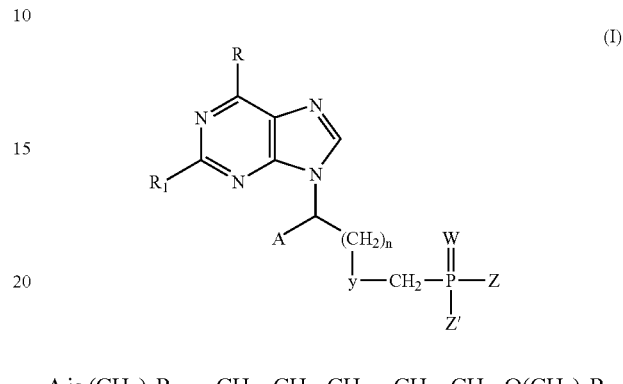

A is (CH$_2$)$_n$R$_2$, —CH=CH$_2$, CH$_2$—CH=CH$_2$, O(CH$_2$)$_n$R$_2$, CH(OH)CH$_3$, CH(OH)CH$_2$OH, CH$_2$—CH(OH)CH$_3$, CH$_2$CH(OH)CH$_2$OH, or CH(OH)CH(OH)CH$_3$,

R, R$_1$ individually is H, NH$_2$OH, Cl, Br, I, aryl, substituted aryl, heterocycle, NR$_3$R$_4$, OR$_3$, or SR$_3$, R$_2$ is H, OH, F, N$_3$, NH$_2$, CO$_2$H, SH, alkyl, substituted alkyl, S-alkyl, O-acyl, CONH$_2$, or CONH-alkyl, n is 1-3, y is O, S, or NH, W is O or S, Z, Z' individually is OR$_3$, OR$_4$, O(CH$_2$)$_m$—O—(CH$_2$)$_x$CH$_3$, NH—CH(alkyl)CO$_2$R$_3$, alkyl, substituted alkyl, OCH$_2$CH$_2$S—C(O)CH$_3$, OCH$_2$CH$_2$S—C(O)CH(CH$_3$)$_2$, OCH$_2$CH$_2$S—C(O)C(CH$_3$)$_3$, OCH$_2$CH$_2$—SC(O)aryl, OCH$_2$CH$_2$—S—S—OCH$_2$CH$_2$OH, OCH$_2$OC(O)C(CH$_3$)$_3$, OCH$_2$—O—C(O)OCH(CH$_3$)$_2$, or OCH$_2$—O—C(O)CH(CH$_3$)$_2$, R$_3$, R$_4$ individually is H, alkyl, substituted alkyl, aryl, or substituted aryl, Both R$_3$ and R$_4$ can form a monocyclic ring of 4-7 atoms with N and optionally other heteroatom in the ring, m is 1-3, x is 0-19;

and pharmaceutically acceptable salts thereof and prodrugs thereof.

The following formulae II to VIII further illustrate, some purine derivatives according to the present disclosure:

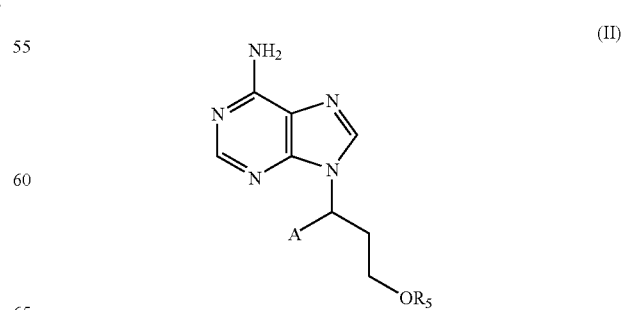

R$_5$ is H,

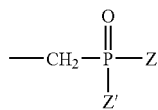

A is $CH_2OH$, $CH_2OCH_3$, $CH_2N_3$, $CH_2NH_2$, $CH(OH)CH_3$, $CH_2F$, or $=CH_2$,

Z, Z' individually is $OR_3$, $OR_4$, $O(CH_2)_m-O-(CH_2)_xCH_3$, $NH-CH(alkyl)CO_2R_3$, alkyl, substituted alkyl, $OCH_2CH_2S-C(O)CH_3$, $OCH_2CH_2S-C(O)CH(CH_3)_2$, $OCH_2CH_2S-C(O)C(CH_3)_3$, $OCH_2CH_2-SC(O)aryl$, $OCH_2CH_2-S-S-OCH_2CH_2OH$, $OCH_2OC(O)C(CH_3)_3$, $OCH_2-O-C(O)OCH(CH_3)_2$, or $OCH_2-O-C(O)CH(CH_3)_2$, $R_3$, $R_4$ individually is H, alkyl, substituted alkyl, aryl, or substituted aryl, Both $R_3$ and $R_4$ can form a monocyclic ring of 4-7 atoms with N or other heteroatom in the ring, m is 1-3, x is 0-19;

and pharmaceutically acceptable salts thereof and prodrugs thereof.

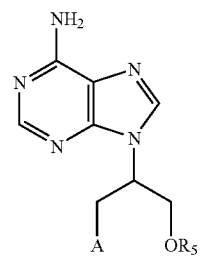

(III)

$R_5$ is H,

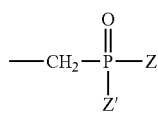

A is $CH_2OH$, $CH_2N_3$, $CH_2NH_2$, $CH_2OCH_3$, $CH_3$, or $CH(OH)CH_3$,

Z, Z' individually is $OR_3$, $OR_4$, $O(CH_2)_m-O-(CH_2)_xCH_3$, $NH-CH(alkyl)CO_2R_3$, alkyl, substituted alkyl, $OCH_2CH_2S-C(O)CH_3$, $OCH_2CH_2S-C(O)CH(CH_3)_2$, $OCH_2CH_2S-C(O)C(CH_3)_3$, $OCH_2CH_2-SC(O)aryl$, $OCH_2CH_2-S-S-OCH_2CH_2OH$, $OCH_2OC(O)C(CH_3)_3$, $OCH_2-O-C(O)OCH(CH_3)_2$, or $OCH_2-O-C(O)CH(CH_3)_2$, $R_3$, $R_4$ individually is H, alkyl, substituted alkyl, aryl, or substituted aryl, Both $R_3$ and $R_4$ can form a ring of 4-7 atoms with N or other heteroatom in the ring, m is 1-3, x is 0-19;

and pharmaceutically acceptable salts thereof and prodrugs thereof.

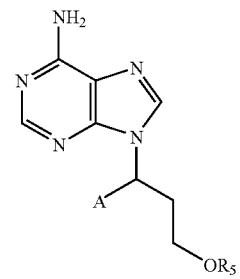

(IV)

$R_5$ is H,

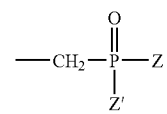

A is $CH_2OH$, $CH_2OCH_3$, $CH_2N_3$, $CH_2NH_2$, $CH(OH)CH_3$, $CH_2F$, $=CH_2$, or $CH_2CH_2OH$,

Z,Z' individually is OH, $-O-CH_2OC(O)C(CH_3)_3$, or $-O-CH_2OC(O)OCH(CH_3)_2$, and pharmaceutically acceptable salts thereof and prodrugs thereof.

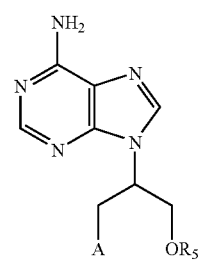

(V)

$R_5$ is H,

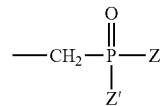

A is $CH_2OH$, $CH_2N_3$, $CH_2NH_2$, $CH_2OCH_3$, $CH_3$, or $CH(OH)CH_3$,

Z,Z' individually is OH, $-O-CH_2-OC(O)C(CH_3)_2$, or $OCH_2OC(O)OCH(CH_3)_2$, and pharmaceutically acceptable salts thereof and prodrugs thereof.

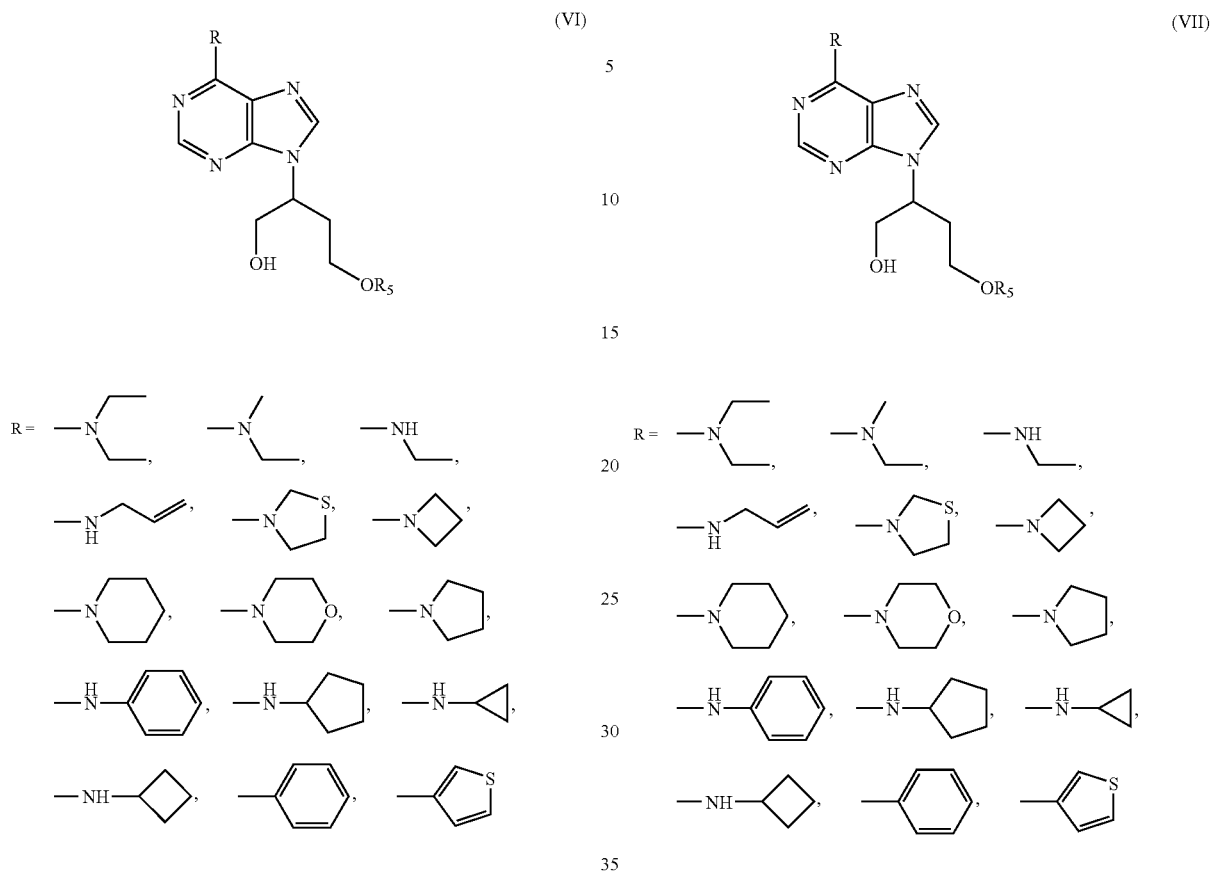

(VI)

R₅ is H,

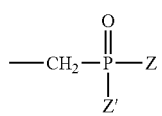

Z, Z' individually is OR₃, OR₄, O(CH₂)ₘ—O—(CH₂)ₓCH₃, NH—CH(alkyl)CO₂R₃, alkyl, substituted alkyl, OCH₂CH₂S—C(O)CH₃, OCH₂CH₂S—C(O)CH(CH₃)₂, OCH₂CH₂S—C(O)C(CH₃)₃, OCH₂CH₂—SC(O)aryl, OCH₂CH₂—S—S—OCH₂CH₂OH, OCH₂OC(O)C(CH₃)₃, OCH₂—O—C(O)OCH(CH₃)₂, or OCH₂—O—C(O)CH(CH₃)₂, R₃, R₄ individually is H, alkyl, substituted alkyl, aryl, or substituted aryl, Both R₃ and R₄ can form a ring of 4-7 atoms with N or other heteroatom in the ring, m is 1-3, x is 0-19;

and pharmaceutically acceptable salts thereof and prodrugs thereof.

(VII)

R₅ is H,

Z, Z' individually is OH, —O—CH₂OC(O)C(CH₃)₃, or —OCH₂OC(O)OCH(CH₃)₂;

and pharmaceutically acceptable salts thereof and prodrugs thereof

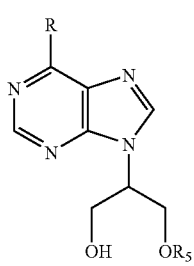

(VIII)

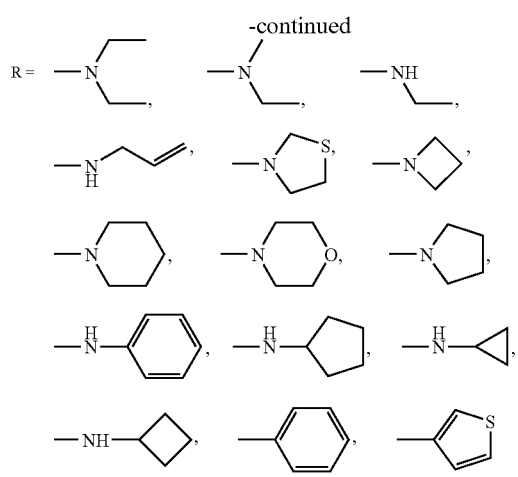

R₅ is H,

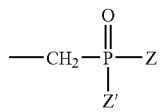

Z, Z' individually is OH, —O—CH₂OC(O)C(CH₃)₃, —OCH₂OC(O)OCH(CH₃)₂;

and pharmaceutically acceptable salts thereof and prodrugs thereof.

Definition of Terms

Listed below are definitions of various terms used to describe this invention. These definitions apply to the terms as they are used throughout this specification, unless otherwise limited in specific instances, either individually or as part of a larger group.

The term "alkyl" refers to straight or branched chain unsubstituted hydrocarbon groups of 1 to 20 carbon atoms, preferably 1 to 8 carbon atoms. The expression "lower alkyl" refers to unsubstituted alkyl groups of 1 to 4 carbon atoms. Alkyl groups may be substituted with halo (Cl, F, Br, I), OH, etc.

Within the above-described definitions, certain embodiments are preferred. Preferred alkyl groups are lower alkyl groups containing 1 to about 8 carbon atoms, and more preferably 1 to about 5 carbon atoms, and can be straight, branched-chain or cyclic saturated aliphatic hydrocarbon groups.

Examples of suitable alkyl groups include methyl, ethyl and propyl. Examples of branched alkyl groups include isopropyl and t-butyl. An example of a suitable aralkyl group is phenethyl. Examples of suitable cycloalkyl groups typically contain 3-8 carbon atoms and include cyclopropyl, cyclobutyl, cyclopentyl and cyclohexyl. The aromatic or aryl groups are preferably phenyl and alkyl substituted aromatic groups (aralkyl) such as phenyl $C_{1-3}$ alkyl and benzyl.

The terms "substituted alkyl" refer to an alkyl group substituted by, for example, one to four substituents, such as halo, trifluoromethyl, trifluoromethoxy, hydroxy, alkoxy, cycloalkyloxy, heterocyclooxy, oxo, alkanoyl, aryloxy, alkanoyloxy, amino, alkylamino, arylamino, aralkylamino, cycloalkylamino, heterocycloamino, disubstituted amines in which the 2 amino substituents are selected from alkyl, aryl or aralkyl, alkanoylamine, aroylamino, aralkanoylamino, substituted alkanolamino, substituted arylamino, substituted aralkanoylamino, thiol, alkylthio, arylthio, aralkylthio, cycloalkylthio, heterocyclothio, alkylthiono, arylthiono, aralkylthiono, alkylsulfonyl, arylsulfonyl, aralkylsulfonyl, sulfonamido (e.g. SO₂NH₂), substituted sulfonamido, nitro, cyano, carboxy, carbamyl (e.g. CONH₂), substituted carbamyl (e.g. CONH alkyl, CONH aryl, CONH aralkyl or cases where there are two substituents on the nitrogen selected from alkyl, aryl or aralkyl), alkoxycarbonyl, aryl, substituted aryl, guanidino and heterocyclos, such as indolyl, imidazolyl, furyl, thienyl, thiazolyl, pyrrolidyl, pyridyl, pyrimidyl and the like. Where noted above where the substituent is further substituted it will be with halogen, alkyl, alkoxy, aryl or aralkyl.

The term "halogen" or "halo" refers to fluorine, chlorine, bromine and iodine.

The term "aryl" refers to monocyclic or bicyclic aromatic hydrocarbon groups having 6 to 12 carbon atoms in the ring portion, such as phenyl, naphthyl, biphenyl and diphenyl groups, each of which may be substituted.

The term "substituted aryl" refers to an aryl group substituted by, for example, one to four substituents such as alkyl; substituted alkyl, halo, trifluoromethoxy, trifluoromethyl, hydroxy, alkoxy, azido, cycloalkyloxy, heterocyclooxy, alkanoyl, alkanoyloxy, amino, alkylamino, aralkylamino, hydroxyalkyl, aminoalkyl, azidoalkyl, alkenyl, alkynyl, allenyl, cycloalkylamino, heterocycloamino, dialkylamino, alkanoylamino, thiol, alkylthio, cycloalkylthio, heterocyclothio, ureido, nitro, cyano, carboxy, carboxyalkyl, carbamyl, alkoxycarbonyl, alkylthiono, arylthiono, alkysulfonyl, sulfonamido, aryloxy and the like. The substituent may be further substituted by halo, hydroxy, alkyl, alkoxy, aryl, substituted aryl, substituted alkyl or aralkyl. "Substituted benzyl" refers to a benzyl group substituted by, for example, any of the groups listed above for substituted aryl.

The term "acyl" refers to the residual moiety of a carboxylic acid group without the OH group of the acid and includes alkyl and acyl carboxylic acids. The alkyl group typically contains about 1-20 carbon atoms and more typically about 1-8 carbon atoms. The acyl group typically contains 6-12 carbon atoms. Examples of suitable acyl groups include acetyl and benzoyl.

The terms "heterocycle" refer to an optionally substituted, fully saturated or unsaturated, aromatic or nonaromatic cyclic group, for example, which is a 4 to 7 membered monocyclic, 7 to 11 membered bicyclic, or 10 to 15 membered tricyclic ring system, which has at least one heteroatom and at least one carbon atom in the ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized and the nitrogen heteroatoms may also optionally be quaternized. The heterocyclic group may be attached at any heteroatom or carbon atom.

Prodrug forms of the compounds bearing various nitrogen functions (amino, hydroxyamino, amide, etc.) may include the following types of derivatives where each R group individually may be hydrogen, substituted or unsubstituted alkyl, aryl, alkenyl, alkynyl, heterocycle, alkylaryl, aralkyl, aralkenyl, aralkynl, cycloalkyl or cycloalkenyl groups as defined earlier.

(a) Carboxamides, —NHC(O)R
(b) Carbamates, —NHC(O)OR
(c) (Acyloxy)alkyl Carbamates, NHC(O)OROC(O)R (d) Enamines, —NHCR(=CHCO$_2$R) or —NHCR(=CHCONR$_2$)

(e) Schiff Bases, —N=CR$_2$ (f) Mannich Bases (from carboximide compounds), RCONHCH$_2$NR$_2$ Preparations of such prodrug derivatives are discussed in various literature sources (examples are: Alexander et al., J. Med. Chem. 1988, 31, 318; Aligas-Martin et al., PCT WO pp/41531, p. 30). The nitrogen function converted in preparing these derivatives is one (or more) of the nitrogen atoms of a compound of the disclosure.

Prodrug forms of carboxyl-bearing compounds of the disclosure include esters (—CO$_2$R) where the R group corresponds to any alcohol whose release in the body through enzymatic or hydrolytic processes would be at pharmaceutically acceptable levels. Another prodrug derived from a carboxylic acid form of the invention may be a quaternary salt type

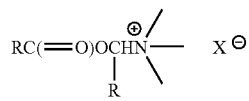

of structure described by Bodor et al., J. Med. Chem. 1980, 23, 469.

It is of course understood that the compounds of the present disclosure relate to all optical isomers and stereoisomers at the various possible atoms of the molecule.

Pharmaceutically acceptable salts of the compounds of the present disclosure include those derived from pharmaceutically acceptable inorganic or organic acids. Examples of suitable acids include hydrochloric, hydrobromic, sulfuric, nitric, perchloric, fumaric, maleic, phosphoric, glycollic, lactic, salicyclic, succinic, toluene-p-sulfonic, tartaric, acetic, citric, methanesulfonic, formic, benzoic, malonic, naphthalene-2-sulfonic, trifluoroacetic and benzenesulfonic acids. Salts derived from appropriate bases include alkali such as sodium and ammonia.

The compounds of the present disclosure can be synthesized by persons skilled in the art once aware of the present disclosure without undue experimentation.

However, the following schemes illustrate methods for preparing compounds of the present disclosure. In order to facilitate an understanding of the present disclosure, the general methods will be discussed with respect to preparing various preferred compounds of the present disclosure.

Scheme 1.

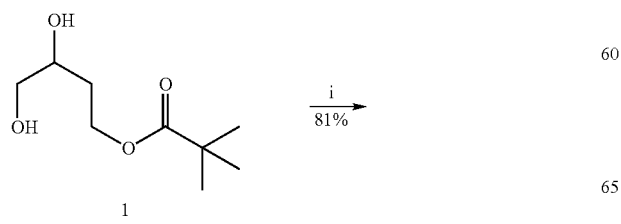

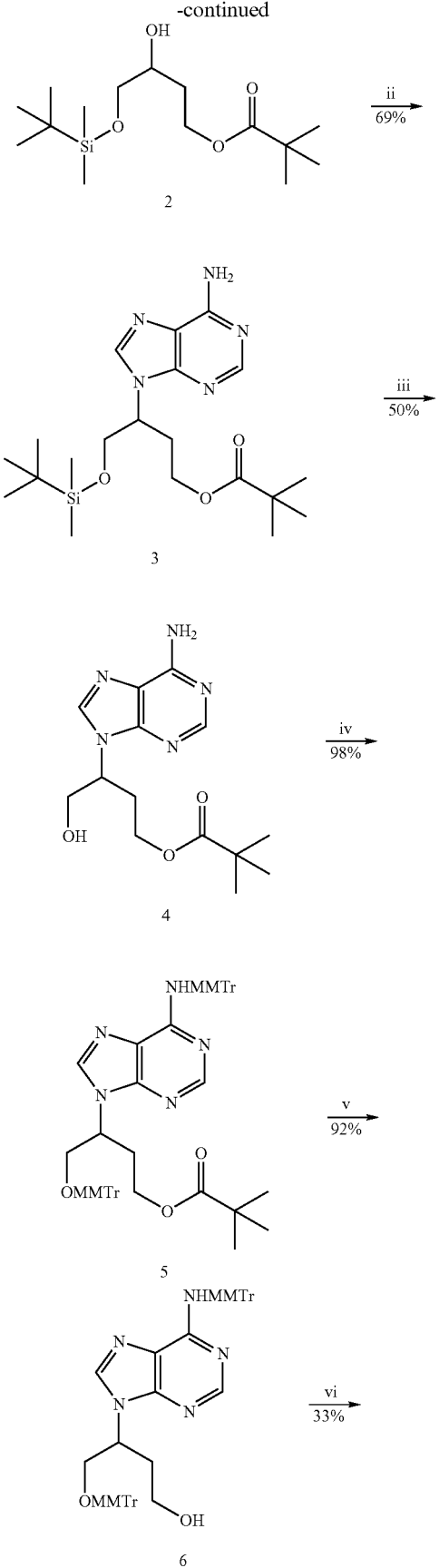

17
-continued
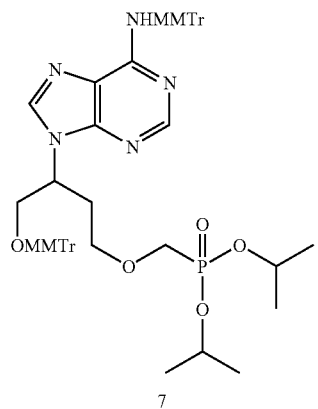
7
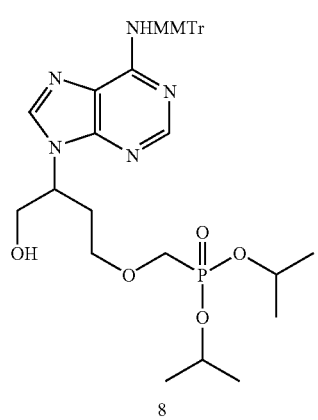
8
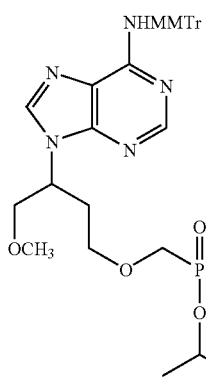
9
MMTr = Monomethoxytrityl
Reagents: i) TBDMS-Cl, imidazole; ii) Adenine, Ph₃P, DEAD; iii) Bu₄NF, THF;
iv) MMTrCl, pyridine; v) NaOH; vi) NaH, TsO—CH₂—P(O)(O—iPr)₂;
vii) HCl, CH₃CN; viii) NaH, CH₃I.
18
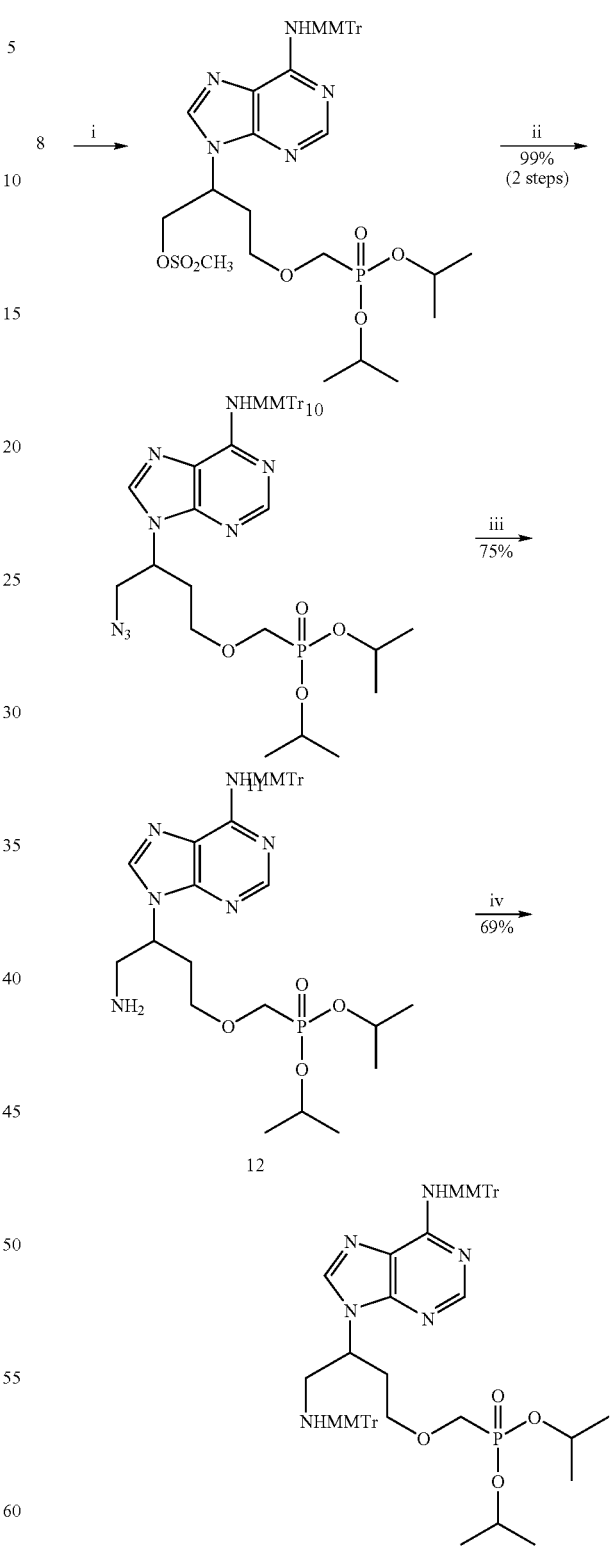
Reagents: i) MsCl; ii) NaN₃; iii) Ph₃P, H₂O, THF; iv) MMTrCl, pyridine.

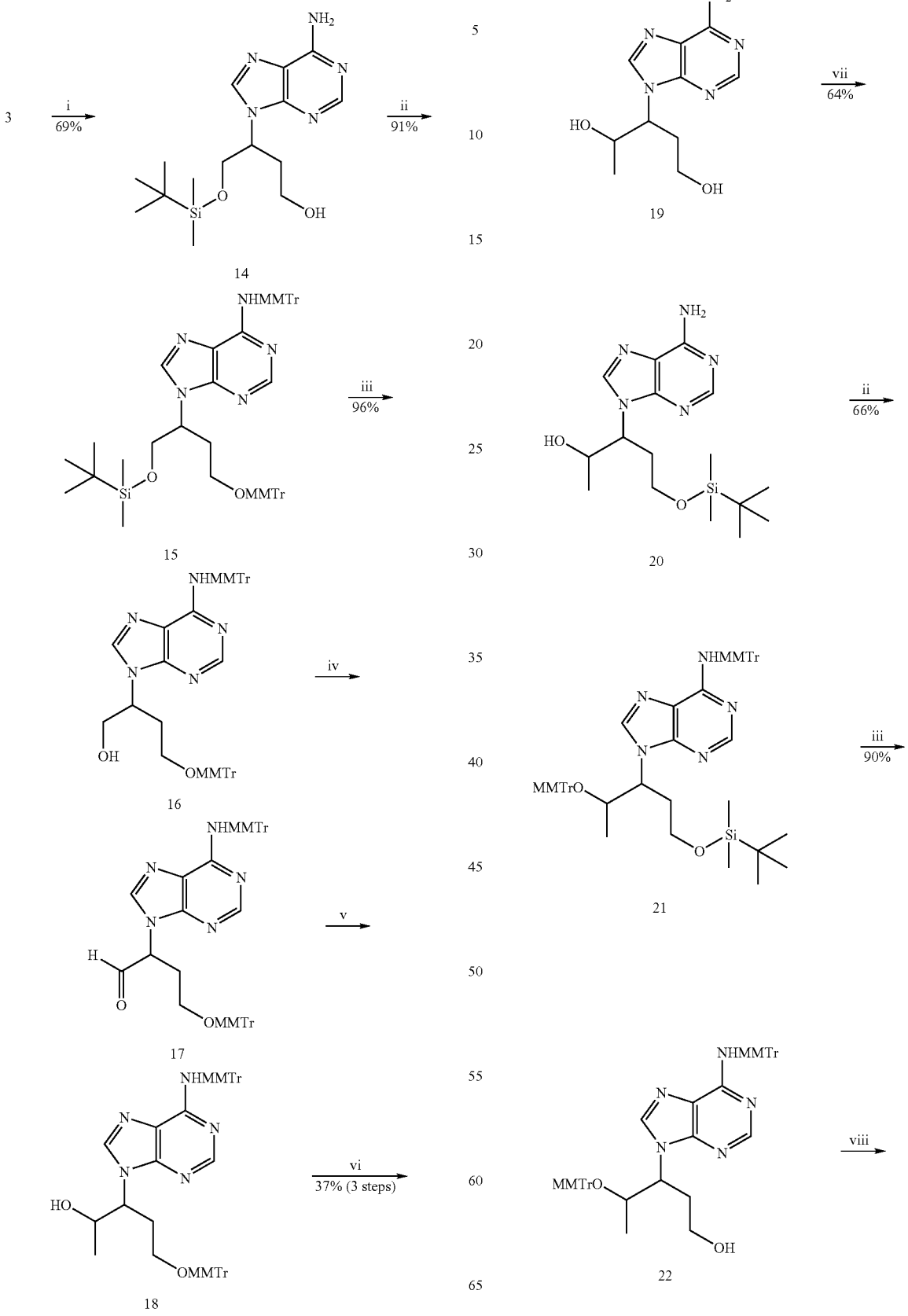

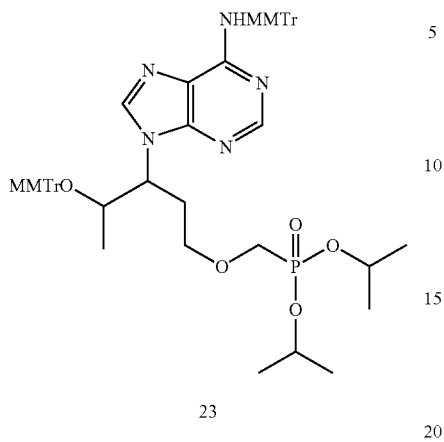
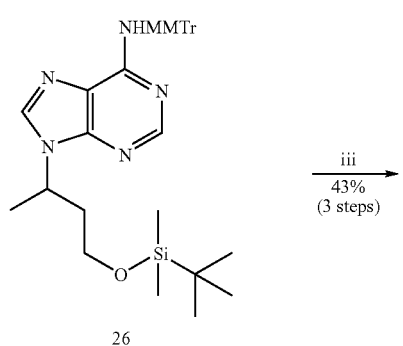
Reagents: i) NaOMe; ii) MMTrCl, pyridine; iii) Bu₄NF, THF; iv) Dess-Martin;
v) MeMgBr; vi) HCl; vii) TBDMS-Cl, imidazole; viii) NaH, TsO—CH₂—P(O)(O-ip)₂.
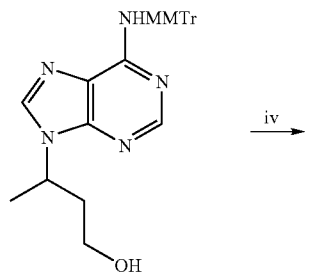
Scheme 4.
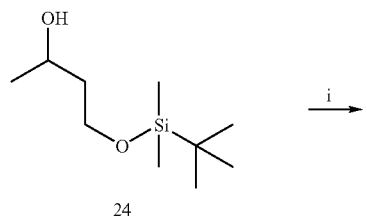
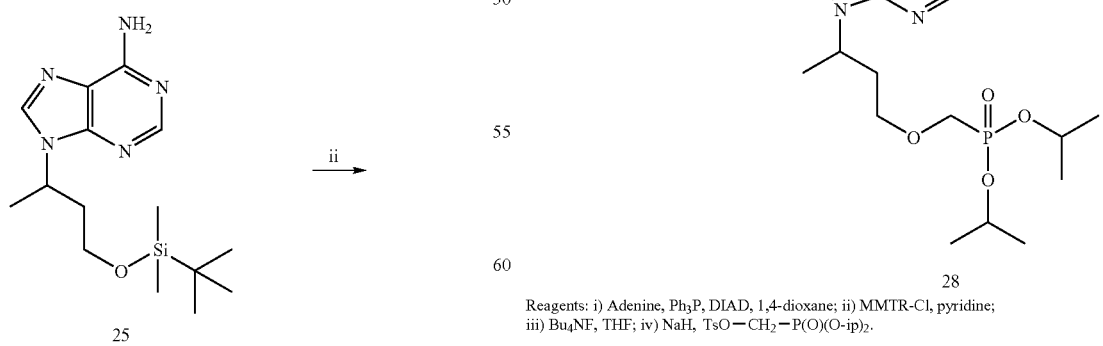
Reagents: i) Adenine, Ph₃P, DIAD, 1,4-dioxane; ii) MMTR-Cl, pyridine;
iii) Bu₄NF, THF; iv) NaH, TsO—CH₂—P(O)(O-ip)₂.

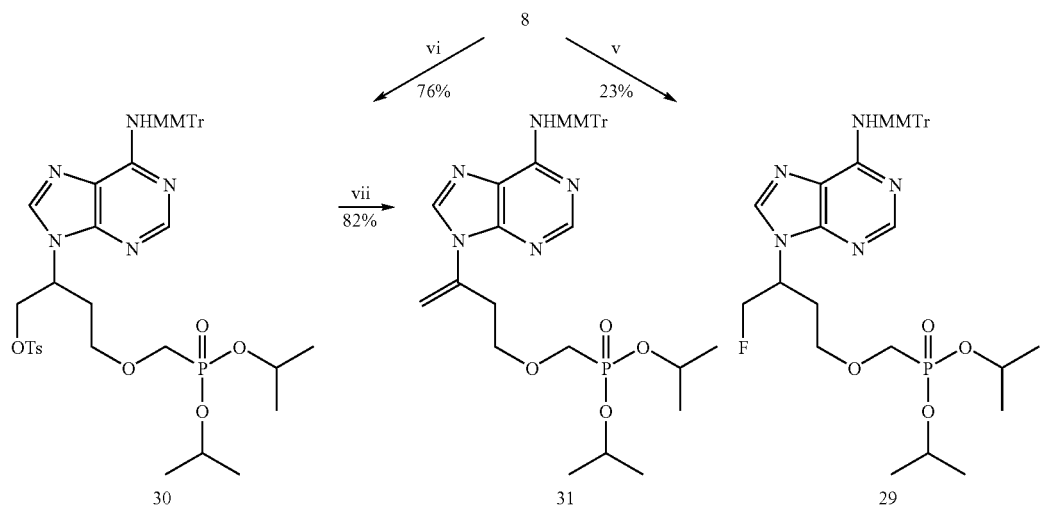
Scheme 5.
Reagents: v) DAST, Et₃N; vi) TsCl; vii) NaI, DBU.
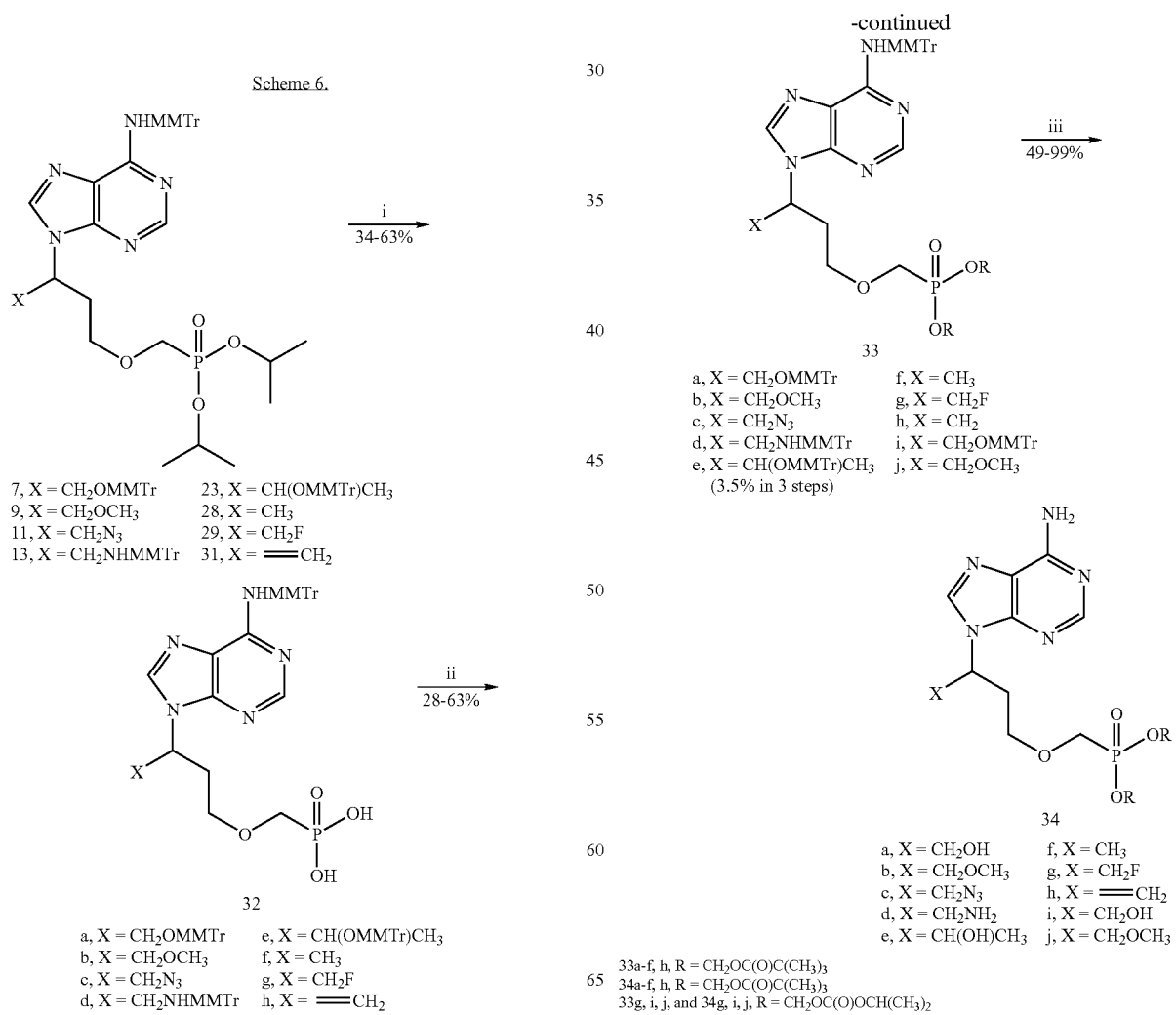
Scheme 6.

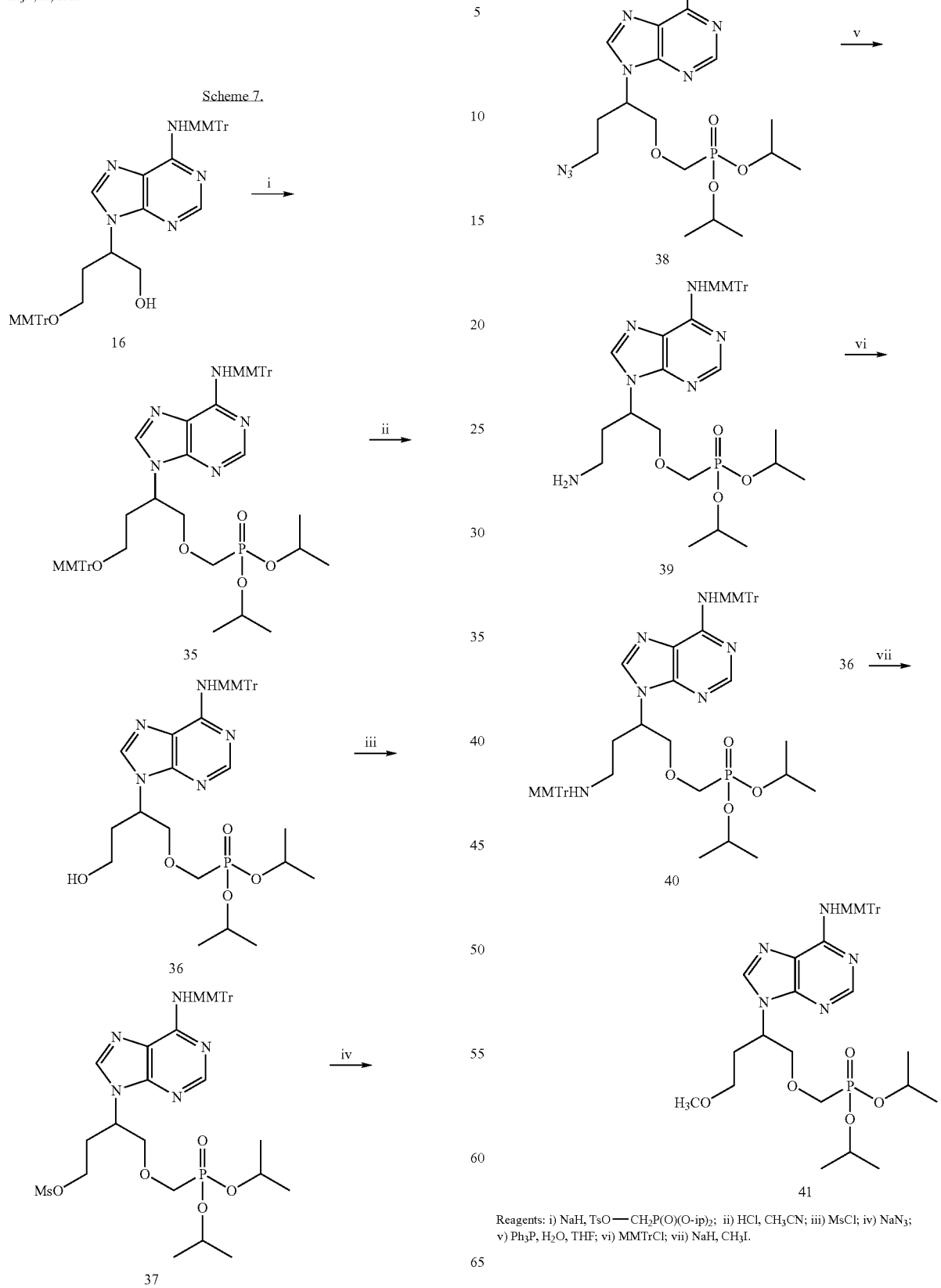

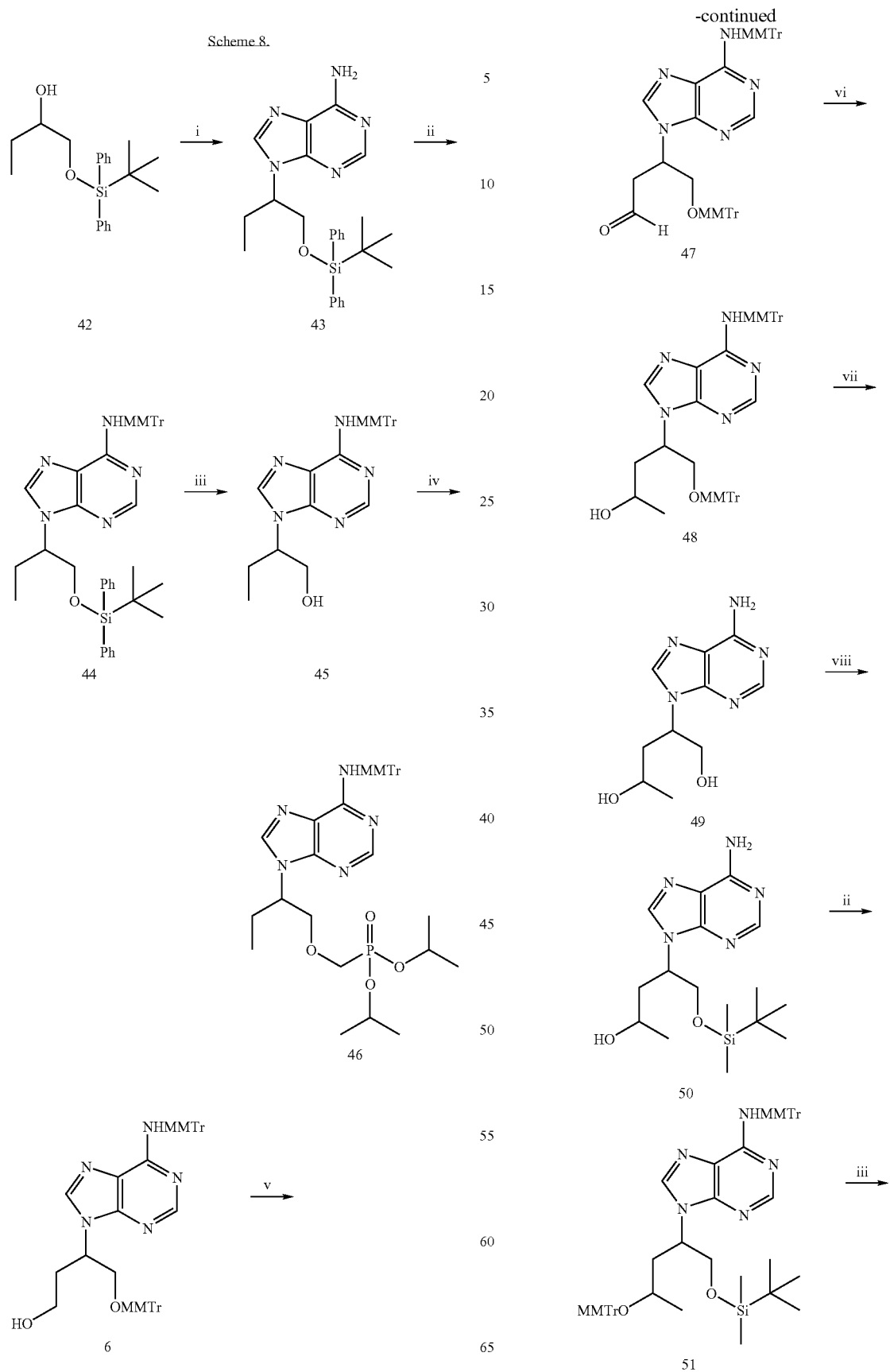

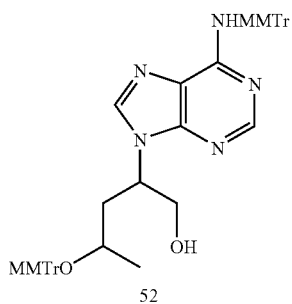

52

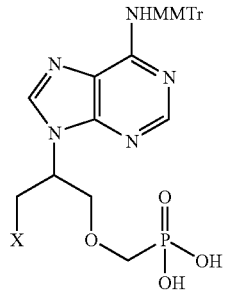

54 a, X = CH$_2$OMMTr
b, X = CH$_2$N$_3$
c, X = CH$_2$NHMMTr
d, X = CH$_2$OCH$_3$
e, X = CH$_3$
f, X = CH(OMMTr)CH$_3$

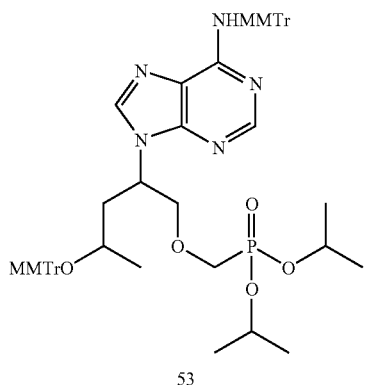

53

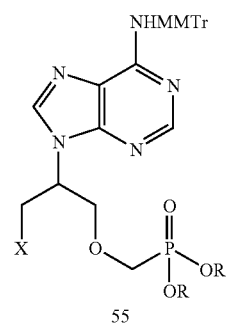

55 a, X = CH$_2$OMMTr
b, X = CH$_2$N$_3$
c, X = CH$_2$NHMMTr
d, X = CH$_2$OCH$_3$
e, X = CH$_3$
f, X = CH(OMMTr)CH$_3$

Reagents: i) Adenine, Ph$_3$P, DIAD; ii) MMTr—Cl; iii) Bu$_4$NF, THF; iv) NaH, TsO—CH$_2$—P(O)(O—iPr)$_2$; v) Dess-Martin; vi) CH$_3$MgBr; vii) HCl; viii) TBDMS—Cl, imidazole.

Scheme 9.

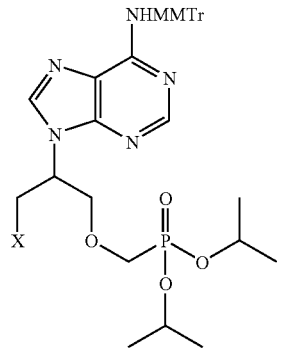

35, X = CH$_2$OMMTr
38, X = CH$_2$N$_3$
40, X = CH$_2$NHMMTr
41, X = CH$_2$OCH$_3$
46, X = CH$_3$
53, X = CH(OMMTr)CH$_3$

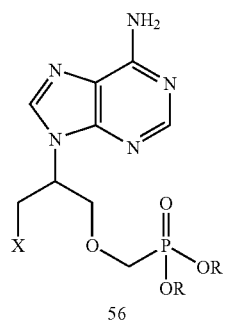

56 a, X = CH$_2$OH
b, X = CH$_2$N$_3$
c, X = CH$_2$NH$_2$
d, X = CH$_2$OCH$_3$
e, X = CH$_3$
f, X = CH(OH)CH$_3$ 55-56a, b, e, f, R = CH$_2$OC(O)C(CH$_3$)$_3$
55-56c, d, R = CH$_2$OC(O)OCH(CH$_3$)$_2$

Reagents: i) TMSI, Et$_3$N; ii) ClCH$_2$OC(O)C(CH$_3$)$_3$ or ClCH$_2$OC(O)O(CH$_3$)$_2$, Et$_3$N; iii) HCl.

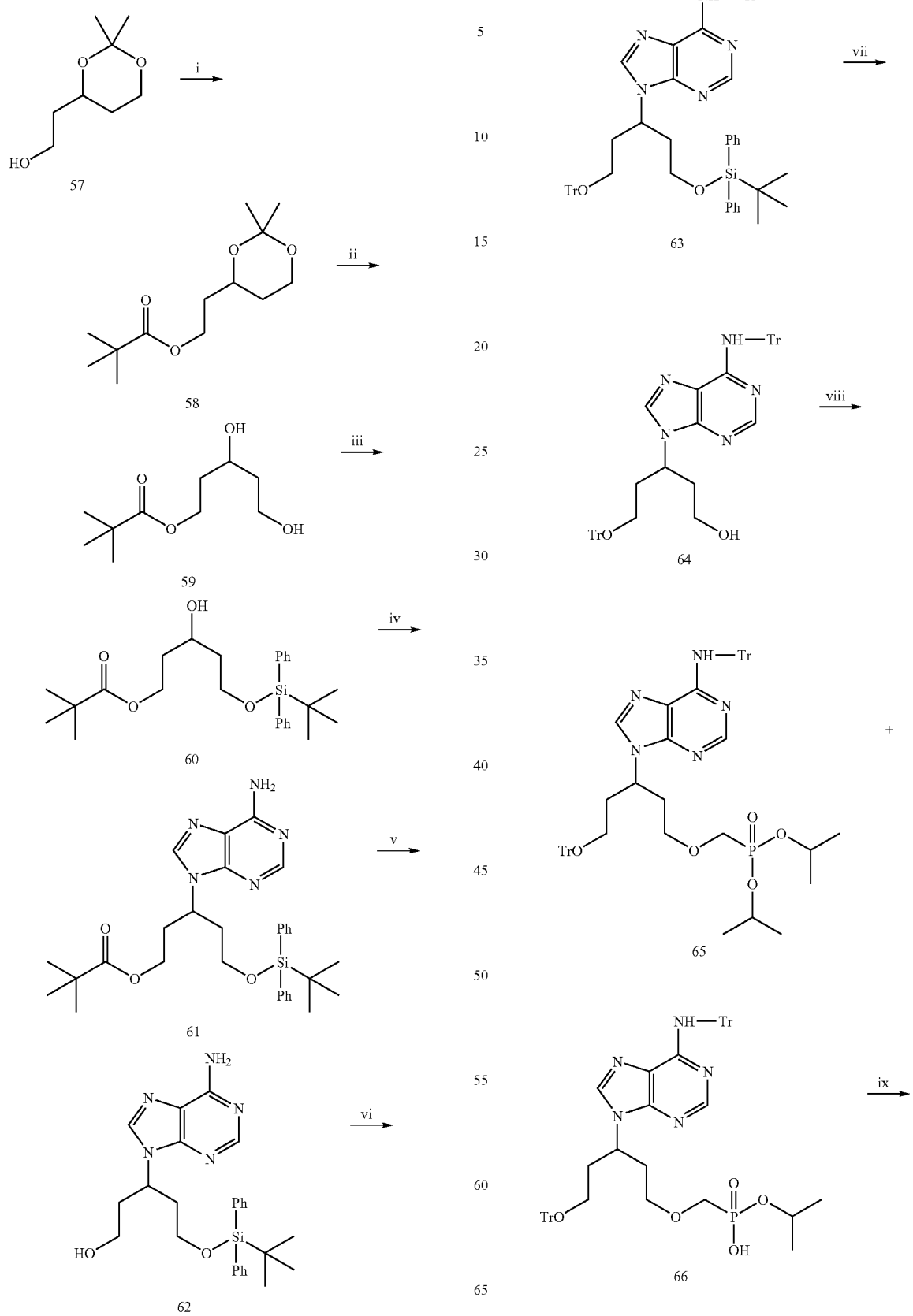

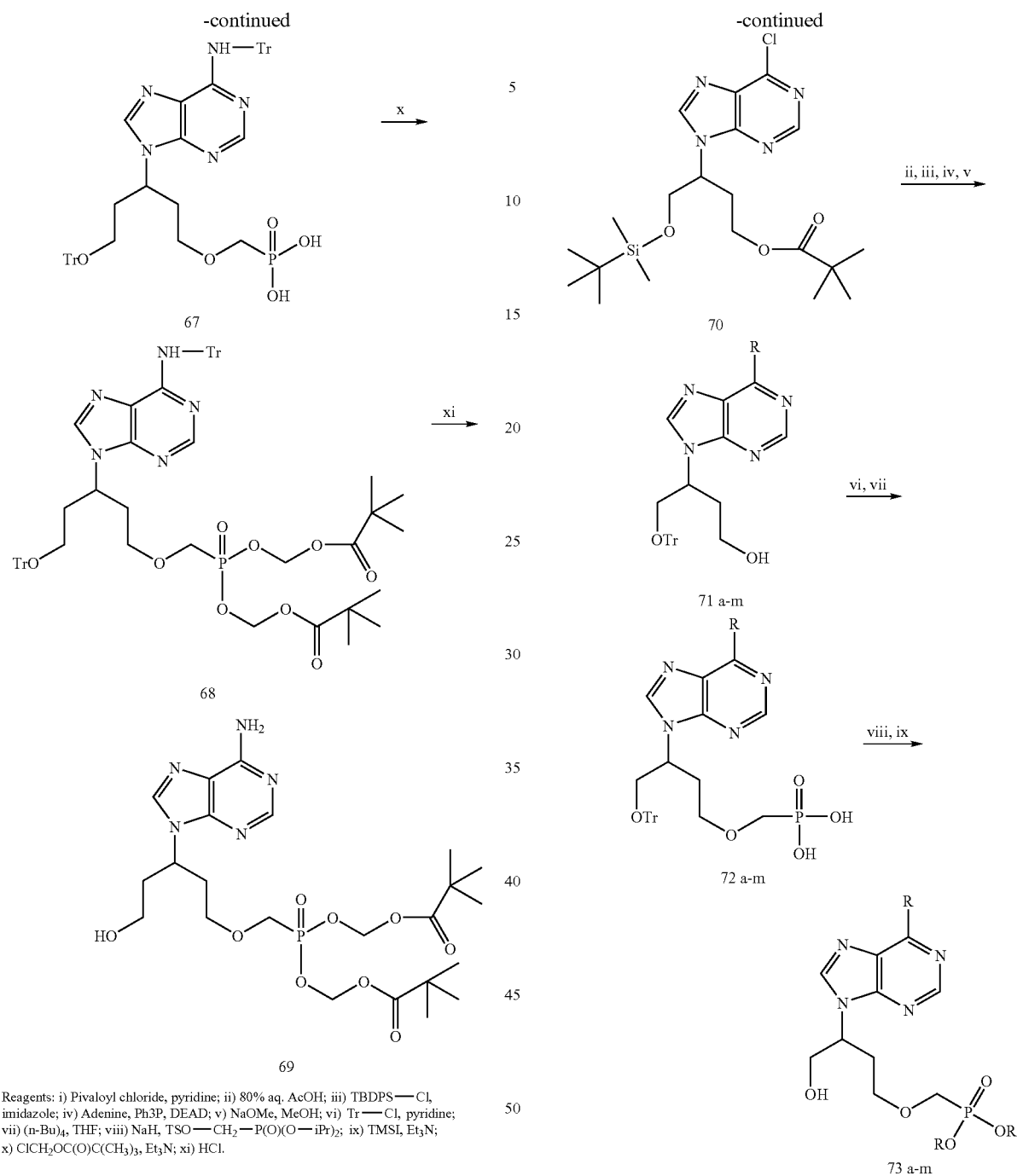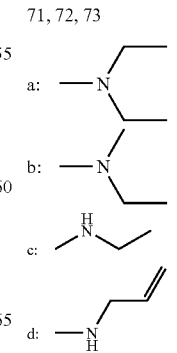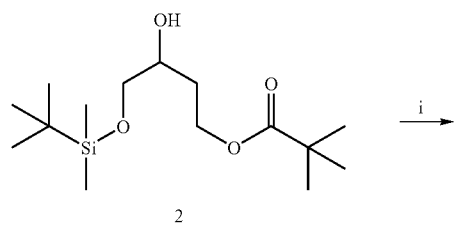

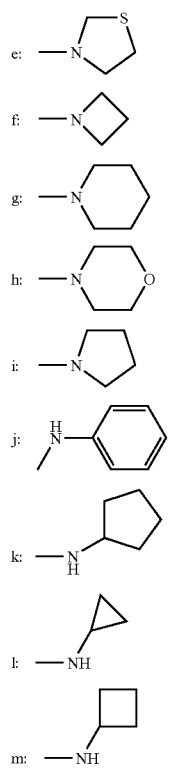

e:
f:
g:
h:
i:
j:
k:
l:
m:

73c, d, k: R = CH₂OC(O)C(CH₃)₃
73a-b, e-j, l, m: R = CH₂OC(O)OCH(CH₃)₂

Reagents: i) 6-Chloropurine, Ph₃P, DIAD; ii) Amine, EtOH, Et₃N; iii) Bu₄NF, THF; iv) TrCl, pyridine; v) NaOMe; vi) NaH, TsO—CH₂—P(O)(O—iPr)₂; vii) TMSI, Et₃N; viii) ClCH₂OC(O)C(CH₃)₃ or ClCH₂OC(O)OCH(CH₃)₂, Et₃N; ix) HCl, CH₃CN.

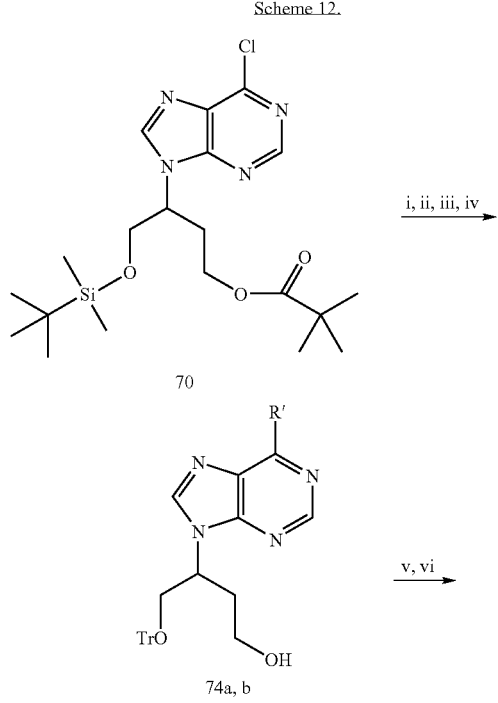

Scheme 12.

70

74a, b

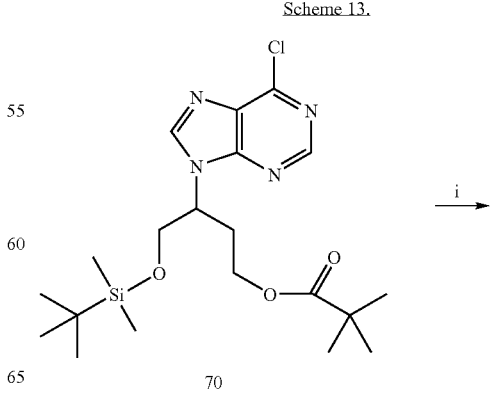

75a, b 76a, b 76a, b: R = CH₂OC(O)C(CH₃)₃

74-76a: R' = phenyl 74-76b: R' = 3-thienyl

Reagents: i) R'B(OH)₂, PdCl₂(PPh₃)₂, NaHCO₃; ii) Bu₄NF, THF; iii) TrCl, pyridine; iv) NaOMe; v) NaH, TsO—CH₂—P(O)(O—iPr)₂; vi) TMSI, Et₃N; vii) ClCH₂OC(O)C(CH₃)₃, Et₃N; viii) HCl, CH₃CN.

Scheme 13.

70

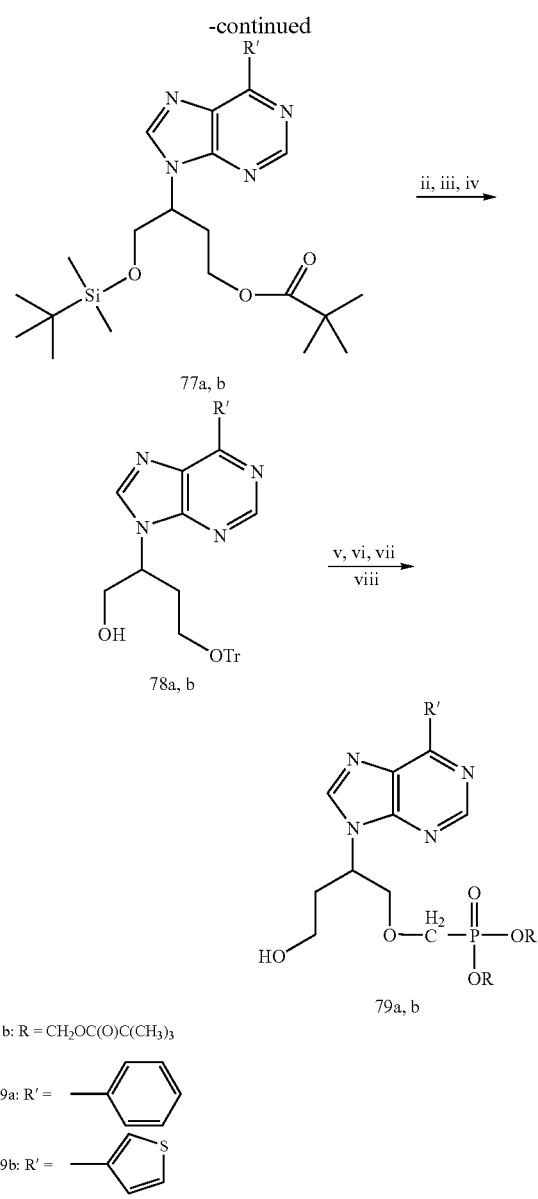

79a, b: R = CH₂OC(O)C(CH₃)₃

77-79a: R' = phenyl 77-79b: R' = thienyl

Reagents: i) R'B(OH)₂, PdCl₂(Ph₃P)₂, NaHCO₃; ii) NaOMe; iii) TrCl, pyridine; iv) Bu₄NF, THF; v) NaH, TsO—CH₂—P(O)(O—iPr)₂; vi) TMSI, Et₃N; vii) ClCH₂OC(O)C(CH₃)₃, Et₃N; viii) HCl, CH₃CN.

Examples of some specific compounds within the scope of the present disclosure are:

(±)-9-[(1-Hydroxymethyl)(3-tert-butylcarbonyloxy)propyl]adenine (4)

(±)-9-[(1-Monomethoxytrityloxymethyl)(3-hydroxy)propyl]-N⁶-monomethoxytrityladenine (6)

(±)-9-[(1-Monomethoxytrityloxymethyl)(3-(diisopropylphosphono)methoxy)propyl]-N⁶-monomethoxytrityladenine (7)

(±)-9-[(1-Hydroxymethyl)(3-(diisopropylphosphono)methoxy)propyl]-N⁶-monomethoxytrityladenine (8)

(±)-9-[(1-Mthoxymethyl)(3-(diisopropylphosphono)methoxy)propyl]-N⁶-monomethoxytrityladenine (9)

(±)-9-[(1-Azidomethyl)(3-(diisopropylphosphono)methoxy)propyl]-N⁶-monomethoxytrityladenine (11)

(±)-9-[(1-Aminomethyl)(3-(diisopropylphosphono)methoxy)propyl]-N⁶-monomethoxytrityladenine (12)

(±)-9-[(1-N-Monomethoxytritylaminomethyl)(3-(diisopropylphosphono)methoxy)propyl]-N⁶-monomethoxytrityladenine (13)

(±)-9-[(1-Hydroxymethyl)(3-monomethoxytrityloxy)propyl]-N⁶-monomethoxytrityladenine (16)

(±)-9-[(1-(2-Hydroxy)ethyl)(3-hydroxy)propyl]adenine (19)

(±)-9-[(1-(2-Monomethoxytrityloxy)ethyl)(3-hydroxy)propyl]-N⁶-monomethoxytrityladenine (22)

(±)-9-[((1-(2-Monomethoxytrityloxy)ethyl)(3-(diisopropylphosphono)methoxy)propyl]-N⁶-monomethoxytrityladenine (23)

(±)-9-[(1-Methyl)(3-hydroxy)propyl]-N⁶-monomethoxytrityladenine (27)

(±)-9-[((1-Methyl)(3-(diisopropylphosphono)methoxy)propyl]-N⁶-monomethoxytrityladenine (28)

(±)-9-[(1-Fluoromethyl)(3-(diisopropylphosphono)methoxy)propyl]-N⁶-monomethoxytrityladenine (29)

(±)-9-[(1-Tosyloxymethyl)(3-(diisopropylphosphono)methoxy)propyl]-N⁶-monomethoxytrityladenine (30)

(±)-9-[(1-Methylene)(3-(diisopropylphosphono)methoxy)propyl]-N⁶-monomethoxytrityladenine (31)

(±)-9-[(1-Monomethoxytrityloxymethyl)(3-phosphonomethoxy)propyl]-N⁶-monomethoxytrityladenine (32a)

(±)-9-[(1-Methoxymethyl)(3-phosphonomethoxy)propyl]-N⁶-monomethoxytrityladenine (32b)

(±)-9-[(1-Azidomethyl)(3-phosphonomethoxy)propyl]-N⁶-monomethoxytrityladenine (32c)

(±)-9-[(1-N-Monomethoxytritylaminomethyl)(3-phosphonomethoxy)propyl]-N⁶-monomethoxytrityladenine (32d)

(±)-9-[(1-(2-Monomethoxytrityloxy)ethyl)(3-phosphonomethoxy)propyl]-N⁶-monomethoxytrityladenine (32e)

(±)-9-[(1-Methyl)(3-phosphonomethoxy)propyl]-N⁶-monomethoxytrityladenine (32f)

(±)-9-[(1-Fluoromethyl)(3-phosphonomethoxy)propyl]-N⁶-monomethoxytrityladenine (32g)

(±)-9-[(1-Methylene)(3-phosphonomethoxy)propyl]-N⁶-monomethoxytrityladenine (32h)

Butyloxycarbonylmethylphosphono)methoxy)propyl]-N⁶-monomethoxytrityladenine (33a)

(±)-9-[(1-Methoxymethyl)(3-(di-tert-butyloxycarbonylmethylphosphono)methoxy)propyl]-N⁶-monomethoxytrityladenine (33b)

(±)-9-[(1-Azidomethyl)(3-(di-tert-butyloxycarbonylmethylphosphono)methoxy)propyl]-N⁶-monomethoxytrityladenine (33c)

(±)-9-[(1-N-Monomethoxytritylaminomethyl)(3-(di-tert-butyloxycarbonylmethylphosphono)methoxy)propyl]-N⁶-monomethoxytrityladenine (33d)

(±)-9-[(1-(2-Monomethoxytrityloxy)ethyl)(3-(di-tert-butyloxycarbonylmethylphosphono)methoxy)propyl]-N⁶-monomethoxytrityladenine (33e)

(±)-9-[(1-Methyl)(3-(di-tert-butyloxycarbonylmethylphosphono)methoxy)propyl]-N⁶-monomethoxytrityladenine (33f)

(±)-9-[(1-Fluoromethyl)(3-(di-isopropyloxycarbonyloxymethylphosphono)methoxy)propyl]-N⁶-monomethoxytrityladenine (36g)

(±)-9-[(1-Methylene)(3-(di-tert-butyloxycarbonylmethylphosphono)methoxy)propyl]-N⁶-monomethoxytrityladenine (33h)

(±)-9-[(1-Monomethoxytrityloxymethyl)(3-(di-isopropyloxycarbonyloxymethyl-phosphono)methoxy)propyl]-N⁶-monomethoxytrityladenine (33i)

(±)-9-[(1-Methoxymethyl)(3-(di-isopropyloxycarbonyloxymethylphosphono)methoxy)-propyl]-N⁶-monomethoxytrityladenine (33j)

(±)-9-[(1-Hydroxymethyl)(3-(di-tert-butyloxycarbonylmethylphosphono)methoxy)propyl]-adenine (34a)

(±)-9-[(1-Methoxymethyl)(3-(di-tert-butyloxycarbonylmethylphosphono)methoxy)propyl]-adenine (34b)

(±)-9-[(1-Azidomethyl)(3-(di-tert-butyloxycarbonylmethylphosphono)methoxy)propyl]-adenine (34c)

(±)-9-[(1-Aminomethyl)(3-(di-tert-butyloxycarbonylmethylphosphono)methoxy)propyl]-adenine (37d)

(±)-9-[(1-(2-Hydroxy)ethyl)(3-(di-tert-butyloxycarbonylmethylphosphono)methoxy)propyl]-adenine (37e)

(±)-9-[(1-Methyl)(3-(di-tert-butyloxycarbonylmethylphosphono)methoxy)propyl]adenine (37f)

(±)-9-[(1-Fluoromethyl)(3-(di-isopropyloxycarbonyloxymethylphosphono)methoxy)propyl]-adenine (34g)

(±)-9-[(1-Methylene)(3-(di-tert-butyloxycarbonylmethylphosphono)methoxy)propyl]-adenine (34h)

(±)-9-[(1-Hydroxymethyl)(3-(di-isopropyloxycarbonyloxymethylphosphono)methoxy)-propyl]adenine (34i)

(±)-9-[1-[(Diisopropylphosphono)methoxy]methyl][(3-azido)propyl]-$N^6$-monomethoxytrityladenine (38)

(±)-9-[1-[(Diisopropylphosphono)methoxy]methyl][(3-amino)propyl]-$N^6$-monomethoxytrityladenine (39)

(±)-9-[1-[(Diisopropylphosphono)methoxy]methyl][(3-(methoxy)propyl]-$N^6$-monomethoxytrityladenine (41)

(±)-9-[1-Hydroxymethyl]propyl-$N^6$-monomethoxytrityladenine (45)

(±)-9-[1-[(Diisopropylphosphono)methoxy]methyl][propyl]-$N^6$-monomethoxytrityladenine (46)

(±)-9-[1-[(Phosphonomethoxy)methyl][(3-monomethoxytrityloxy)propyl]-$N^6$-monomethoxytrityladenine (54a)

(±)-9-[1-[(Phosphonomethoxy)methyl][(3-azido)propyl]-$N^6$-monomethoxytrityladenine (54b)

(±)-9-[1-[(Phosphonomethoxy)methyl][(3-monomethoxytritylamino)propyl]-$N^6$-monomethoxytrityladenine (54c)

(±)-9-[1-[(Phosphonomethoxy)methyl][(3-methoxy)propyl]-$N^6$-monomethoxytrityladenine (54d)

(±)-9-[1-[(Phosphonomethoxy)methyl]propyl]-$N^6$-monomethoxytrityladenine (54e)

(±)-9-[1-[(Phosphonomethoxy)methyl][((3-monomethoxytrityloxy)butyl]-$N^6$-monomethoxytrityladenine (54f)

(±)-9-[1-[(Di-tert-butylcarbonyloxymethylphosphonomethoxy)methyl][(3-monomethoxytrityloxy)propyl]-$N^6$-monomethoxytrityladenine (55a)

(±)-9-[1-[(Di-tert-butylcarbonyloxymethylphosphonomethoxy)methyl][(3-azido)propyl]-$N^6$-monomethoxytrityladenine (55b)

(±)-9-[1-[(Di-isopropyloxycarbonyloxymethylphosphonomethoxy)methyl][(3-monomethoxytritylamino)propyl]-$N^6$-monomethoxytrityladenine (55c)

(±)-9-[1-[(Di-isopropyloxycarbonyloxymethylphosphonomethoxy)methyl][(3-methoxy)propyl]-$N^6$-monomethoxytrityladenine (55d)

(±)-9-[1-[(Di-tert-butylcarbonyloxymethylphosphonomethoxy)methyl][propyl]-$N^6$-monomethoxytrityladenine (55e)

(±)-9-[1-[(Di-tert-butylcarbonyloxymethylphosphonomethoxy)methyl][(3-monomethoxytrityloxy)butyl]-$N^6$-monomethoxytrityladenine (55f)

(±)-9-[1-[(Di-tert-butylcarbonyloxymethylphosphonomethoxy)methyl][(3-hydroxy)propyl]adenine (56a)

(±)-9-[1-[(Di-tert-butylcarbonyloxymethylphosphonomethoxy)methyl][(3-azido)propyl]adenine (56b)

(±)-9-[1-[(Di-isopropyloxycarbonyloxymethylphosphonomethoxy)methyl][(3-amino)propyl]adenine (56c)

(±)-9-[1-[(Di-isopropyloxycarbonyloxymethylphosphonomethoxy)methyl][(3-methoxy)propyl]adenine (56d)

(±)-9-[1-[(Di-tert-butylcarbonyloxymethylphosphonomethoxy)methyl]propyl]adenine (56e)

(±)-9-[1-[(Di-tert-butylcarbonyloxymethylphosphonomethoxy)methyl][(3-hydroxy)butyl]adenine (56f)

(±)-9-[(1-Trityloxyethyl)(3-di-tert-butylcarbonyloxymethylphosphonomethoxy)propyl]-$N^6$-trityladenine (68)

(±)-9-[(1-Hydroxyethyl)(3-di-tert-butylcarbonyloxymethylphosphonomethoxy)propyl]adenine (69)

(±)-9-[(1-Trityloxymethyl)(3-hydroxy)propyl]-6-diethylaminopurine (71a)

(±)-9-[(1-Trityloxymethyl)(3-hydroxy)propyl]-6-(N-methyl-N-ethyl)aminopurine (71b)

(±)-9-[(1-Trityloxymethyl)(3-hydroxy)propyl]-6-ethylaminopurine (71c)

(±)-9-[(1-Trityloxymethyl)(3-hydroxy)propyl]-6-allylaminopurine (71d)

(±)-9-[(1-Trityloxymethyl)(3-hydroxy)propyl]-6-N-thiazolidinopurine (71e)

(±)-9-[(1-Trityloxymethyl)(3-hydroxy)propyl]-6-N-azetidinopurine (71f)

(±)-9-[(1-Trityloxymethyl)(3-hydroxy)propyl]-6-N-piperidinopurine (71g)

(±)-9-[(1-Trityloxymethyl)(3-hydroxy)propyl]-6-N-morpholinopurine (71h)

(±)-9-[(1-Trityloxymethyl)(3-hydroxy)propyl]-6-N-pyrrolidinopurine (71i)

(±)-9-[(1-Trityloxymethyl)(3-hydroxy)propyl]-6-N-phenylaminopurine (71j)

(±)-9-[(1-Trityloxymethyl)(3-hydroxy)propyl]-6-cyclopentylaminopurine (71k)

(±)-9-[(1-Trityloxymethyl)(3-hydroxy)propyl]-6-cyclopropylaminopurine (71l)

(±)-9-[(1-Trityloxymethyl)(3-hydroxy)propyl]-6-cyclobutylaminopurine (71m)

(±)-9-[(1-Trityloxymethyl)(3-phosphonomethoxy)propyl]-6-diethylaminopurine (72a)

(±)-9-[(1-Trityloxymethyl)(3-phosphonomethoxy)propyl]-6-N-methyl-N-ethylaminopurine (72b)

(±)-9-[(1-Trityloxymethyl)(3-phosphonomethoxy)propyl]-6-ethylaminopurine (72c)

(±)-9-[(1-Trityloxymethyl)(3-phosphonomethoxy)propyl]-6-allylaminopurine (72d)

((±)-9-[(1-Trityloxymethyl)(3-phosphonomethoxy)propyl]-6-N-thiazolidinopurine (72e)

(±)-9-[(1-Trityloxymethyl)(3-phosphonomethoxy)propyl]-6-N-azetidinopurine (72f)

(±)-9-[(1-Trityloxymethyl)(3-phosphonomethoxy)propyl]-6-N-piperidinopurine (72g)

(±)-9-[(1-Trityloxymethyl)(3-phosphonomethoxy)propyl]-6-N-morpholinopurine (72h)

(±)-9-[(1-Trityloxymethyl)(3-phosphonomethoxy)propyl]-6-N-pyrrolidinopurine (72i)

(±)-9-[(1-Trityloxymethyl)(3-phosphonomethoxy)propyl]-6-N-phenylaminopurine (72j)

(±)-9-[(1-Trityloxymethyl)(3-phosphonomethoxy)propyl]-6-cyclopentylaminopurine (72k)

((±)-9-[(1-Trityloxymethyl)(3-phosphonomethoxy)propyl]-6-cyclopropylaminopurine (72l)

(±)-9-[(1-Trityloxymethyl)(3-phosphonomethoxy)propyl]-6-cyclobutylaminopurine (72m)

(±)-9-[(1-Hydroxymethyl)(3-(di-isopropyloxycarbonyloxymethylphosphono)methoxy)propyl]-6-diethylaminopurine (73a)

(±)-9-[(1-Hydroxymethyl)(3-(di-isopropyloxycarbonyloxymethylphosphono)methoxy)propyl]-6-N-methyl-N-ethylaminopurine (73b)

(±)-9-[(1-Hydroxymethyl)(3-(di-tert-butyloxycarbonylmethylphosphono)methoxy)propyl]-6-ethylaminopurine (73c)

(±)-9-[(1-Hydroxymethyl)(3-(di-tert-butyloxycarbonylmethylphosphono)methoxy)propyl]-6-allylaminopurine (73d)

(±)-9-[(1-Hydroxymethyl)(3-(di-isopropyloxycarbonyloxymethylphosphono)methoxy)propyl]-6-N-thiazolidinopurine (73e)

(±)-9-[(1-Hydroxymethyl)(3-(di-isopropyloxycarbonyloxymethylphosphono)methoxy)propyl]-6-N-azetidinopurine (73f)

(±)-9-[(1-Hydroxymethyl)(3-(di-isopropyloxycarbonyloxymethylphosphono)methoxy)propyl]-6-N-piperidinopurine (73g)

(±)-9-[(1-Hydroxymethyl)(3-(di-isopropyloxycarbonyloxymethylphosphono)methoxy)propyl]-6-N-morpholinopurine (73h)

(±)-9-[(1-Hydroxymethyl)(3-(di-isopropyloxycarbonyloxymethylphosphono)methoxy)propyl]-6-N-pyrrolidinopurine (73i)

(±)-9-[(1-Hydroxymethyl)(3-(di-isopropyloxycarbonyloxymethylphosphono)methoxy)propyl]-6-N-phenylaminopurine (73j)

(±)-9-[(1-Hydroxymethyl)(3-(di-tert-butyloxycarbonylmethylphosphono)methoxy)propyl]-6-cyclopentylaminopurine (73k)

(±)-9-[(1-Hydroxymethyl)(3-(di-isopropyloxycarbonyloxymethylphosphono)methoxy)propyl]-6-cyclopropylaminopurine (73l)

(±)-9-[(1-Hydroxymethyl)(3-(di-isopropyloxycarbonyloxymethylphosphono)methoxy)propyl]-6-cyclobutylaminopurine (73m)

(±)-9-[(1-Hydroxymethyl)(3-(di-tert-butyloxycarbonylmethylphosphono)methoxy)propyl]-6-phenylpurine (76a)

(±)-9-[(1-Hydroxymethyl)(3-(di-tert-butyloxycarbonylmethylphosphono)methoxy)propyl]-6-(3-thiophenyl)purine (76b)

(±)-9-[(1-Hydroxyethyl)(3-(di-tert-butyloxycarbonylmethylphosphono)methoxy)ethyl]-6-phenylpurine (79a)

(±)-9-[(1-Hydroxyethyl)(3-(di-tert-butyloxycarbonylmethylphosphono)methoxy)ethyl]-6-(3-thiophenyl)purine (79b)

The following non-limiting examples are presented to further illustrate the present disclosure.

All reagents and solvents are purchased from Aldrich and used as received. $^1$H NMR and $^{13}$C NMR are recorded on a Bruker 300 MHz instrument. Chemical shifts (δ) are reported in parts per million (ppm) referenced to TMS at 0.00 or respective deuterated solvent peak. Coupling constants (J) are reported in hertz. IR spectra were obtained from films on NaCl plates for oils or KBr pellets for solids with a scan range of 4000-500 cm$^{-1}$ on a FT-IR spectrometer (BioRad FTS-3500GX). Mass spectra data were acquired on a Waters ZMD mass spectrometer coupled with a Waters System 2695 for loading of the samples in ES positive or negative mode. HRMS data were recorded on Bruker Bioapex 4.7E. The elemental analysis (C, H and N) were performed by Atlantic Microlab in Norcross, Ga., USA. The TLC solvent systems, CMA-80 and CMA-50, refers to chloroform:methanol:conc. NH$_4$OH (80:18:2) and chloroform:methanol:conc. NH$_4$OH (50:40:10), respectively. Tetraethyl ammonium bicarbonate is abbreviated as TEAB. The non-UV active compounds were visualized by charring the TLC plate sprayed with ammonium molybdate/cesium sulfate spray prepared by dissolving conc. H$_2$SO$_4$ (22.4 mL), CeSO$_4$ (45 mg), (NH$_4$)$_6$Mo$_7$O$_{24}$.4 H$_2$O (7 g) in 100 mL water. The olefin compounds are visualized by using KMnO$_4$ spray. The following conditions are used for HPLC analysis.

Column: Spherisorb ODS 4.6×250 mm. Mobile phase: solvent A: water, solvent B: MeOH. Gradient: time: 0 min., A: 95%, B 5%; time: 20 min., A: 0%, B: 100%; then isocratic for 5 min. Time: 25.1 min., A: 95, B: 5% then isocratic for 5 min. Flow rate 1.0 mL/min. Run time 30 min. Detection UV at 259 nm.

The following abbreviations are used herein.
Tr: trityl
Bn: benzyl
TBDPS: tert-butyldiphenylsilyl
m-CPBA: 3-chloroperoxybenzoic acid
TFA: trifluoroacetic acid
TBDMSCl: tert-butyldimethylsilyl chloride
DMF: dimethylformamide
THF: tetrahydrofuran
LDA: lithium diisopropylamine
TEAB: triethylammonium bicarbonate
mMTrCl: monomethoxytrityl chloride
DMAP: dimethylaminopyridine
DEAE: diethylaminoethyl-sepharose
CMA-80: Chloroform 80:MeOH 18: NH$_4$OH :2
CMA-50: Chloroform 50:MeOH 40: NH$_4$OH :10
Bz: benzoyl
BnBr: benzyl bromide
LiHMDS: lithium hexamethyldisalazane
TBDPSCl: tert-butyldiphenylsilyl chloride
DMSO: dimethylsulfoxide
RMgBr: alkyl magnesium bromide
DIBAL: diisobutylaluminum hydride
DBN: 1,5-diazabicyclo[4.3.0]non-5-ene
DBU: 1,8-diazabicyclo[5.4.0]undec-7-ene
MeMgBr: methylmagnesium bromide

EXAMPLE 1

(±)-4-Pivaloylbutan-1,2,4-triol (1). Butan-1,2,4-triol (139.0 g, 1.3 mol) is stirred with acetone (5.0 L) and p-toluenesulphonic acid monohydrate (7.0 g, 0.037 mol) at room temperature for 4 h. The mixture is neutralized with triethylamine and concentrated under vacuum below 40° C. It is dissolved in 30% acetone in hexanes (0.5 L) and passed through a short plug of silica gel and further eluted with 30% acetone in hexanes. The fractions containing the product are pooled together and concentrated to give 186 g (98%) of 1,2-isopropylidenebutan-1,2,4-triol which is dissolved in pyridine (1.5 L) and pivaloyl chloride (161 g, 1.34 mol) added to it over a period of 1 h below 10° C. The mixture is further stirred at room temperature for 16 h and filtered to remove insoluble material and the pyridine removed under vacuum from the filtrate. The residue is partitioned between ethyl acetate and water. The organic layer is separated, washed with water and brine and dried over MgSO$_4$. After filtration, the filtrate is concentrated and the residue is taken in 80% acetic-acid (2.5 L) and heated at 55° C. for 4 h. Acetic acid is removed under vacuum and the residue is purified on a silica gel column using ethyl acetate:hexanes as eluent to give 182 g (75%) of the desired target as an oil: $^1$H NMR (CDCl$_3$): δ 4.25-4.42 (m, 1H), 4.08-4.22 (m, 1H), 3.60-3.81 (m, 3H), 3.42-3.52 (m, 1H), 2.02-2.12 (m, 1H), 1.65-1.80 (m, 2H), 1.17 (s, 9H).

EXAMPLE 2

(±)-1-tert-Butyldimethylsilyl-4-pivaloylbutan-1,2,4-triol (2). To a solution of 1 (70 g, 0.368 mol) in $CH_2Cl_2$ (2.0 L) is added imidazole (31.3 g, 0.46 mol) and tert-butyldimethylsilyl chloride (58.2 g, 0.386 mol) and stirred at room temperature for 3 h. The reaction mixture is diluted with water, the organic layer separated and washed with water and brine and then dried over $MgSO_4$. After filtration, the filtrate is concentrated and the residue is purified on a silica gel column using ethyl acetate:hexanes as eluent to give 91.2 g (81%) of product as an oil: $^1H$ NMR (DMSO-$d_6$): δ 4.66 (d, J=5.2 Hz, 1H), 4.14-3.90 (m, 2H), 3.54-3.25 (m, 3H), 1.84-1.72 (m, 1H), 1.51-1.39 (m, 1H), 1.10 (s, 9H), 0.83 (s, 9H), 0.01 (s, 6H).

EXAMPLE 3

(±)-9-[(1-tert-Butyldimethylsilyloxymethyl)(3-pivaloyloxy)propyl]adenine (3). To a mixture of 2 (80 g, 0.263 mol), triphenylphosphine (138 g, 0.525 mol) and adenine (71 g, 0.525 mol) in anhydrous dioxane (3.2 L) is added a solution of DIAD (104 mL, 0.525 mol) in dioxane (400 mL) over a period of 3.5 h at room temperature and the mixture is stirred further for 16 h. The reaction mixture is filtered through a short pad of Celite to remove insoluble materials and the residue purified on a column of silica gel eluting with chloroform:methanol (100:0 to 97:3) to provide the desired compound, which is crystallized from ethyl acetate:hexanes (1:3) to afford 77 g (69%) of 3 as a white solid, mp 175-177° C.: $^1H$ NMR (DMSO-$d_6$): 8.14 (s, 1 H), 8.08 (s, 1 H), 7.15 (bs, 2 H), 4.64 (m, 1 H), 3.78-4.03 (m, 4 H), 2.16-2.48 (m, 2 H), 1.02 (s, 9 H), 0.70 (s, 9 H), −0.12 (s, 3 H) and −0.18 (s, 3 H). IR (KBr, cm$^{-1}$) 3352, 3166, 2958, 2859, 1721, 1656, 1597 and 1477. MS (ES$^+$) 422.46 (M+H)$^+$. Anal. Calcd for $C_{20}H_{35}N_5O_3Si.0.25\ H_2O$: C, 56.37; H, 8.39; N, 16.43. Found: C, 56.16; H, 8.13; N, 16.36.

EXAMPLE 4

(±)-9-[(1-Hydroxymethyl)(3-tert-butylcarbonyloxy)propyl]adenine (4). Partially purified 3 (91.5 g, obtained from 60.5 g of 2) is dissolved in THF (1 L) and treated with tetrabutyl ammonium fluoride (1M in THF, 130 mL) and the reaction mixture stirred at room temperature for 2 h followed by concentration. The residue is purified on a silica gel column using chloroform:CMA-80 (1:0 to 1:1) as eluent to give 21.1 g (35%, 2 steps) of 4 as a white solid, mp 188° C.: $^1H$ NMR (DMSO-$d_6$): δ 8.20 (s, 1H), 8.13 (s, 1H), 7.22 (bs, 2H), 5.16 (t, J=5.4 Hz, 1H), 4.69-4.59 (m, 1H), 4.04-3.71 (m, 4H), 2.44-2.19 (m, 2H), 1.07 (s, 9H). IR (KBr, cm$^{-1}$) 3334, 3172, 2968, 1727, 1676, 1607 and 1164. Anal. Calcd for $C_{14}H_{21}N_5O_3$: C, 54.71; H, 6.89; N, 22.79. Found: C, 54.41; H, 6.90; N, 22.48.

EXAMPLE 5

(±)-9-[(1-Monomethoxytrityloxymethyl)(3-tert-butylcarbonyloxy)propyl]-N$^6$-monomethoxytrityladenine (5). A solution of 4 (21 g, 0.068 mol) in pyridine (370 mL) is treated with monomethoxytrityl chloride (86.2 g, 0.28 mol) and the reaction mixture heated at 70° C. with stirring for 20 h. It is diluted with ethyl acetate (1.5 L) and washed with water (2×) and brine and the organic layer dried over $MgSO_4$. After filtration, the filtrate is concentrated and the residue purified on a silica gel column using ethyl acetate: hexanes as eluent (0:1 to 1:1) to give 60.0 g (98%) of product as a yellow solid: $^1H$ NMR (DMSO-$d_6$): δ 8.33 (s, 1H), 7.72 (s, 1H), 7.29-6.81 (m, 25H), 6.75 (d, J=9.0 Hz, 2H), 6.67 (d, J=9.1 Hz, 2H), 4.77-4.65 (m, 1H), 3.93-3.73 (m, 2H), 3.62 (s, 6H), 3.40-3.29 (m, 1H), 3.16-3.05 (m, 1H), 2.58-2.43 (m, 1H), 2.10-1.97 (m, 1H), 1.90 (s, 9H). IR (KBr, cm$^{-1}$) 3419, 2959, 1730, 1605, 1508 and 1250. MS (ES$^+$) 874.27 (M+Na)$^+$.

EXAMPLE 6

(±)-9-[(1-Monomethoxytrityloxymethyl)(3-hydroxy)propyl]-N$^6$-monomethoxytrityladenine (6). A solution of 5 (59.5 g, 0.070 mol) in THF (375 mL) and methanol (150 mL) is treated with 2N NaOH (175 mL, 0.35 mol) at room temperature and stirred for 16 h. The reaction mixture is neutralized with acetic acid to pH 8.0 and diluted with ethyl acetate (1.0 L) and washed with water (2×) and brine and the organic layer dried over $MgSO_4$. After filtration, the filtrate is concentrated and the residue is purified on a silica gel column using ethyl acetate:hexanes:methanol (1:1:0 to 1:1:0.1) as eluent to give 49.8 g (92%) of product as a white solid: $^1H$ NMR (DMSO-$d_6$): δ 8.31 (s, 1H), 7.70 (s, 1H), 7.28-6.83 (m, 25H), 6.74 (d, J=8.8 Hz, 2H), 6.66 (d, J=9.1 Hz, 2H), 4.78-4.67 (m, 1H), 4.46 (t, J=5.3 Hz, 1H ), 3.61 (s, 6H), 3.34-2.98 (m, 4H), 2.30-2.14 (m, 1H), 1.96-1.80 (m, 1H). IR (KBr, cm$^{-1}$) 3412, 2932, 1734, 1608 and 1508. MS (ES$^+$) 790.26 (M+Na)$^+$.

EXAMPLE 7

(±)-9-[(1-Monomethoxytrityloxymethyl)(3-(diisopropylphosphono)methoxy)propyl]-N$^6$-monomethoxytrityladenine (7). A solution of 6 (32 g, 41.7 mmol) in DMF (360 mL) is treated with sodium hydride (60%, 6.7 g, 167.5 mmol) at room temperature and the mixture is stirred for 1 h. To this solution is then added a solution of p-toluenesulfonyloxymethylphosphonate (17.6 g, 50.2 mmol) in DMF (30 mL) and the mixture stirred at room temperature for 24 h. The reaction mixture is diluted with ethyl acetate (2 L), neutralized with acetic acid and washed with water (2×) and brine and the organic layer dried over $MgSO_4$. After filtration, the filtrate is concentrated and the residue purified on a silica gel column using ethyl acetate:hexanes:methanol (1:1:0 to 1:1:0.05) as eluent to give 13.2 g (33%) of product as a white solid: $^1H$ NMR (DMSO-$d_6$): δ 8.36 (s, 1H), 7.78 (s, 1H), 7.36-6.85 (m, 25H), 6.82 (d, J=9.1 Hz, 2H), 6.74 (d, J=8.8 Hz, 2H), 4.80-4.67 (m, 1H), 4.55-4.40 (m, 2H), 3.69 (s, 6H), 3.60 (d, J=7.7 Hz, 2H), 3.45-3.25 (m, 3H), 3.20-3.10 (m, 1H), 2.47-2.37 (m, 1H), 2.18-2.00 (m, 1H), 1.19-1.10 (m, 12H). IR (KBr, cm$^{-1}$) 3418, 2978, 1606, 1508 and 1250. Anal. Calcd for $C_{56}H_{60}N_5O_{11}P.0.5\ H_2O.0.25$ EtOAc: C, 70.06; H, 6.50; N, 7.17. Found: C, 69.85; H, 6.49; N, 7.29.

EXAMPLE 8

(±)-9-[(1-Hydroxymethyl)(3-(diisopropylphosphono) methoxy)propyl]-N$^6$-monomethoxytrityladenine (8). A solution of 7 (3.1 g, 3.3 mmol) in acetonitrile (125 mL) is treated with conc. HCl (0.25 mL) at room temperature and the mixture stirred for 1 h. The reaction is neutralized by adding triethylamine (1 mL) and diluted with ethyl acetate (300 mL). It is then washed with water (2×) and brine and the organic layer dried over $MgSO_4$. After filtration, the filtrate is concentrated and the residue purified on a silica gel column using ethyl acetate:hexanes:methanol (1:1:0 to 1:1:0.2) as eluent to give 1.21 g (55%) of 8 as a white solid: $^1$H NMR (DMSO-d$_6$): δ 8.13 (s, 1H), 7.82 (s, 1H), 7.28-7.10 (m,13H), 6.78 (d, J=8.9 Hz, 2H), 4.97 (t, J=5.3 Hz, 1H), 4.53-4.40 (m, 3H), 3.81-3.54 (m, 4H), 3.65 (s, 3H), 3.41-3.22 (m, 2H), 2.22-2.00 (m, 2H), 1.18-1.06 (m, 12H). IR (KBr, cm$^{-1}$) 3415, 2979, 1605, 1470 and 1250. Anal. Calcd for $C_{36}H_{44}N_5O_6P.0.3$ $H_2O.0.3$ EtOAc: C, 63.32; H, 6.71; N, 9.93. Found: C, 63.42; H, 6.80; N, 9.92.

EXAMPLE 9

(±)-9-[(1-Azidomethyl)(3-(diisopropylphosphono)methoxy)propyl]-N$^6$-monomethoxytrityladenine (11). A solution of 8 (0.5 g, 0.74 mmol) in pyridine (10 mL) was treated with methanesulphonyl chloride (0.132 g, 1.15 mmol) at 0° C. and the mixture stirred for 20 h at room temperature. The reaction mixture is diluted with ethyl acetate (100 mL), washed with water (2×) and brine and the organic layer dried over MgSO$_4$ followed by filtration and concentration. The residue (10) is dissolved in DMF (5 mL), treated with sodium azide (0.138 g, 2.1 mmol) and the mixture stirred for 4 h at 100° C. The reaction mixture is diluted with ethyl acetate (200 mL), washed with water (2×) and brine and the organic layer dried over MgSO$_4$. After filtration, the filtrate is concentrated to give 511 mg (99%, two steps) of product as a light yellow oil: $^1$H NMR (CDCl$_3$): δ 8.01 (s, 1H), 7.82 (s, 1H), 7.40-7.15 (m, 13H), 6.80 (d, J=9.0 Hz, 2H), 4.81-4.67 (m, 3H), 4.21-4.10 (m, 1H), 3.82-3.55 (m, 4H), 3.78 (s, 3H), 3.35-3.25 (m, 1H), 2.49-2.19 (m, 2H), 1.39-1.29 (m, 12H). IR (KBr, cm$^{-1}$) 3418, 2979, 2104, 1605, 1472 and 1250. Anal. Calcd for $C_{36}H_{43}N_8O_5P$: C, 61.88; H, 6.20; N, 16.04. Found: C, 61.80; H, 6.25; N, 15.38. HRMS Calcd for $C_{36}H_{43}N_8O_5P$ (M+H)$^+$ 699.3172. Found 699.3149.

EXAMPLE 10

(±)-9-[(1-Aminomethyl)(3-(diisopropylphosphono)methoxy)propyl]-N$^6$-monomethoxytrityladenine (12). A mixture of 11 (0.95 g, 1.36 mmol) in THF (9.5 mL) and water (1.9 mL) is treated with triphenylphosphine (0.76 g, 2.9 mmol) and stirred at room temperature for 15 h. The reaction mixture is concentrated and purified on a column using chloroform:CMA-80 (1:0 to 1:1) as eluent to give 0.687 g (75%) as a light yellow oil: $^1$H NMR (CDCl$_3$): δ 8.01(s, 1H), 7.86 (s, 1H), 7.38-7.18 (m, 13H), 6.80 (d, J=8.8 Hz, 2H), 4.80-4.66 (m, 2H), 4.65-4.55 (m, 1H), 3.78 (s, 3H), 3.64 (d, J=8.5 Hz, 2H), 3.62-3.53 (m, 1H), 3.43 (dd, J=13.5, 8.1 Hz, 1H), 3.43-3.23 (m, 1H), 3.14 (dd, J=13.5, 4.2 Hz, 1H), 2.41-2.17 (m, 2H), 2.10-1.70 (2H), 1.35-1.29 (m, 12H). HRMS Calcd for $C_{36}H_{45}N_6O_5P$ (M+H)$^+$ 673.3267. Found 673.3292.

EXAMPLE 11

(±)-9-[(1-N-Monomethoxytritylaminomethyl)(3-(diisopropylphosphono)methoxy)propyl]-N$^6$-monomethoxytrityladenine (13). It is prepared from 12 (652 mg) by following the same procedure as given for 5 except 2 equivalents of monomethoxytrityl chloride are used. The crude product is purified on a silica gel column using ethyl acetate:hexanes:methanol (1:1:0 to 1:1:0.1) as eluent to give 13 as a light yellow oil (yield: 69%): $^1$H NMR (DMSO-d$_6$): δ 8.21 (s, 1H), 7.79 (s, 1H), 7.37-6.85 (m, 25H), 6.81 (d, J=9.0 Hz, 2H), 6.67 (d, J=8.8 Hz, 2H), 4.62-4.39 (m, 3H), 3.66 (s, 3H), 3.65 (s, 3H), 3.55 (dd, J=7.9, 3.6 Hz, 2H), 3.37-3.21 (m, 2H), 2.80-2.65 (m, 1H), 2.57-2.37 (m, 1H), 2.19-2.05 (m, 1H), 2.00-1.85 (m, 1H), 1.17-1.07 (m, 12H). IR (KBr, cm$^{-1}$) 3419, 2978, 1605, 1508 and 1251. Anal. Calcd for $C_{56}H_{61}N_6O_6P.1.0$ $H_2O$: C, 70.50; H, 6.55; N, 8.81. Found: C, 70.34; H, 6.53; N, 8.57. HRMS Calcd for $C_{56}H_{61}N_6O_6P$ (M+H)$^+$ 945.4468. Found 945.4474.

EXAMPLE 12

(±)-9-[(1-tert-Butyldimethylsilyloxymethyl)(3-hydroxy)propyl]adenine (14). To a solution of 3 (45 g, 0.107 mol) in MeOH (1.0 L) is added NaOMe (5.4 M solution in MeOH, 39 mL, 0.213 mol) and the reaction mixture is stirred at room temperature for 5 h. The solution is neutralized with acetic acid and concentrated. The residue is purified on a silica gel column using ethyl acetate:hexanes:methanol (1:19:0 to 1:1:0.1) as eluent to provide 25 g (69%) of 14 as a white solid, mp 112-114° C.: $^1$H NMR (DMSO-d$_6$): 8.09 (s, 1 H), 8.08 (s, 1 H), 7.15 (bs, 2 H), 4.62-4.70 (m, 1 H), 4.58 (t, J=4.9 Hz, 1 H), 3.96-4.16 (m, 1 H), 3.81-3.90 (m, 1 H), 3.18-3.44 (m, 2 H), 1.96-2.26 (m, 2 H). 0.70 (s, 9 H), −0.14 (s, 3 H) and −0.22 (s, 3 H). IR (KBr, cm$^{-1}$) 3334, 3186, 2929, 2856, 1657, 1600, 1471 and 1414. MS (ES+) 338.49 (M+H). Anal. Calcd for $C_{15}H_{27}N_5O_2Si$: C, 53.38; H, 8.06; N, 20.75. Found: C, 53.43; H, 8.29; N, 20.65.

EXAMPLE 13

(±)-9-[(1-tert-Butyldimethylsilyloxymethyl)(3-monomethoxytrityloxy)propyl]-N$^6$-monomethoxytrityladenine (15). It is prepared from 14 (25.0 g) by the same method used for 5 and obtained in 91% yield as a white solid, mp 88-92° C.: $^1$H NMR (DMSO-d$_6$): 8.16 (s, 1 H), 7.88 (s, 1 H), 7.02-7.36 (m, 25 H), 6.83 (d, J=8.8 Hz, 2 H), 6.77 (d, J=8.8 Hz, 2 H), 4.84 (m, 1 H), 3.70-3.94 (m, 2 H), 3.71(s, 3 H), 3.69 (s, 3 H), 2.74-2.98 (m, 2 H), 2.08-2.48 (m, 2 H). 0.67 (s, 9 H), −0.157 (s, 3 H) and −0.24 (s, 3 H). IR (KBr, cm$^{-1}$) 3416, 3030, 2951, 1604, 1508, 1467 and 1296. MS (ES$^+$) 882.53 (M+H)$^+$. Anal. Calcd for $C_{55}H_{59}N_5O_4Si$: C, 74.48; H, 6.78; N, 7.78. Found: C, 74.79; H, 6.83; N, 7.43.

EXAMPLE 14

(±)-9-[(1-Hydroxymethyl)(3-monomethoxytrityloxy)propyl]-N$^6$-monomethoxytrityladenine (16). A solution of 15 (10.6 g, 12.02 mmol) in THF (120 mL) is treated with tetrabutyl ammonium fluoride (1M in THF, 12.1 mL) and the reaction mixture stirred at room temperature for 2 h followed by concentration. The residue is purified on a silica gel column using ethyl acetate:hexanes:methanol (1:1:0 to 1:1:0.1) to give 8.87 g (96%) of 16 as a white solid: $^1$H NMR (DMSO-d$_6$): δ 8.21 (s, 1H), 7.92 (s, 1H), 7.38-7.05 (m, 25H), 6.89 (d, J=9.1 Hz, 2H), 6.82 (d, J=9.0 Hz, 2H), 5.09 (t, J=5.4 Hz, 1H), 4.88-4.77 (m, 1H), 3.77-3.70 (m, 2H), 3.76 (s, 3H), 3.73 (s, 3H), 2.96-2.76 (m, 2H), 2.44-2.27 (m, 1H), 2.27-2.11 (m, 1H). IR (KBr, cm$^{-1}$) 3412, 2932, 1734, 1606, 1509, 1251 and 1033. Anal. Calcd for $C_{49}H_{45}N_5O_4.0.25$ $H_2O.0.4$ EtOAc: C, 75.25; H, 6.08; N, 8.67. Found: C, 75.35; H, 6.04; N, 8.50.

EXAMPLE 15

(±)-9-[(1-(2-Hydroxy)ethyl)(3-hydroxy)propyl]adenine (19). A solution of 16 (4.16 g, 5.42 mmol) in methylene chloride (300 mL) is treated with Dess-Martin reagent (4.74 g, 97%, 10.84 mmol) and stirred at room temperature for 4 h. The reaction mixture is concentrated and purified on a silica gel column using hexanes:ethyl acetate (1:0 to 1:2) as eluent to provide 17 (white solid, 1.35 g) and its derivative with loss of one MMTr group (white solid, 1.18 g). The combined products (2.5 g) are dissolved in THF (150 mL), treated with 3M methyl magnesium bromide (10.9 mL, 32.7 mmol) and the mixture stirred for 8 h at room temperature. The reaction mixture is diluted with chloroform (400 mL) and water (100 mL). After filtration through Celite and separation, the organic layer is dried over $MgSO_4$ followed by filtration and concentration. The residue (18 and its derivative with loss of one MMTr) was dissolved in acetonitrile (300 mL) and water (14 mL), treated with 2M HCl (1.5 mL) at room temperature and the mixture stirred for 14 h. The reaction mixture is diluted with water (100 mL) and neutralized by adding 0.5N NaOH followed by concentration to remove most of the organic solvent. The aqueous phase is extracted with ethyl acetate (2×100 mL) and concentrated to dryness. The residue is treated with MeOH (100 mL) and filtered. The filtrate is concentrated and purified on a silica gel column using chloroform:CMA-80 (1:0 to 0:1) as eluent to give 472 mg (37%, three steps) of 19 as a colorless oil: $^1$H NMR (a mixture of diastereomers, DMSO-$d_6$): δ 8.17, 8.167, 8.11 (3s, 2H), 7.26, 7.25 (2s, 2H), 5.24, 5.17 (2d, J=5.2 Hz each, 1H), 4.61-4.50 (m, 2H), 4.20-4.05 (m, 1H), 3.40-3.09 (m, 2H), 2.30-2.03 (m, 2H), 0.98, 0.96 (d, J=6.2 Hz each, 3H). HRMS Calcd for $C_{10}H_{15}N_5O_2$ (M+H)$^+$ 238.1304. Found 238.1307.

EXAMPLE 16

(±)-9-[(1-(2-Hydroxy)ethyl)(3-tert-butyldimethylsilyloxy)propyl]adenine (20). The same method is used as for compound 2. The residue is purified on a silica gel column using chloroform:CMA-80 (1:0 to 1:1) to give 415 mg (64%) of 20 as a white solid: $^1$H NMR (a mixture of diastereomers, DMSO-$d_6$): δ 8.24, 8.239, 8.18 (3s, 2H), 7.32, 7.30 (2s, 2H), 5.32, 5.24 (d, J=5.0 Hz each, 1H), 4.72-4.51 (m, 1H), 4.22-4.10 (m, 1H), 3.70-3.60 (m, 1H), 3.49-3.35 (m, 1H), 2.45-2.12 (m, 2H), 1.06, 1.04 (d, J=6.2 Hz each, 3H), 0.93, 0.91 (s, 9H), 0.00, −0.02 (2s, 6H). HRMS Calcd for $C_{16}H_{29}N_5O_2Si$ (M+H)$^+$ 352.2168. Found 352.2176.

EXAMPLE 17

(±)-9-[(1-(2-Monomethoxytrityloxy)ethyl)(3-tert-butyldimethylsilyloxy)propyl]-$N^6$-monomethoxytrityladenine (21). It is prepared from 20 (392 mg) by following the same procedure as given for 5. The crude product is purified on a silica gel column using ethyl acetate:hexanes (1:0 to 2:1) as eluent to give 66% of product as a colorless oil: $^1$H NMR (a mixture of diastereomers, DMSO-$d_6$): δ 8.39, 8.38, 7.99, 7.95 (4s, 2H), 7.57-7.23 (m, 25H), 7.08-6.89 (m, 4H), 4.91-4.76 (1H), 3.93, 3.92, 3.91, 3.88 (4s, 6H), 3.87-3.35 (m, 3H), 2.97-2.43 (m, 2H), 0.99, 0.92 (d, J=6.0 Hz each, 3H), 0.93 (s, 9H), 0.03, 0.01, 0.00, −0.04 (4s, 6H). HRMS Calcd for $C_{56}H_{61}N_5O_4Si$ (M+H)$^+$ 1089.4891. Found 1089.4859.

EXAMPLE 18

(±)-9-[(1-(2-monomethoxytrityloxy)ethyl)(3-hydroxy)propyl]-$N^6$-monomethoxytrityladenine (22). It is prepared from 21 (640 mg) by following the same procedure as given for 16. The crude product is purified on a silica gel column using a mixture of ethyl acetate:hexanes:methanol (1:1:0 to 1:1:0.1) as eluent to give 90% of product as a colorless film: $^1$H NMR (a mixture of diastereomers, DMSO-$d_6$): δ 8.26, 8.23 (2s, 1H), 7.79, 7.77 (2s, 1H), 7.45-6.71 (m, 29H), 4.73-4.50 (m, 2H), 3.76, 3.74, 3.72, 3.71 (4s, 6H), 3.54-3.40 (m, 1H), 3.27-3.12 (m, 1H), 3.09-2.93 (m, 1H), 2.59-2.12, 1.99-1.83 (2m, 2H), 0.84, 0.80 (d, J=6.1 Hz each, 3H). IR (KBr, cm$^{-1}$) 3414, 1737, 1606, 1508, 1250 and 1033.

EXAMPLE 19

(±)-9-[(1-Methyl)(3-hydroxy)propyl]-$N^6$-monomethoxytrityladenine (27). Compound 24 (1.93 g) is converted to 25 according to the procedure used for 3. A small amount of the product is chromatographed two times (eluting with $CHCl_3$:MeOH, 100:0 to 95:5) to get the pure 25 for characterization: $^1$H NMR (DMSO-$d_6$): δ 8.28 (s, 1H), 8.20 (s, 1H), 7.26 (s, 2H), 4.89-4.76 (m, 1H), 3.67-3.56 (m, 1H), 3.54-3.44 (m, 1H), 2.41-2.27 (m, 1H), 2.20-2.04 (m, 1H), 1.61 (d, J=7.1 Hz, 3H), 0.90 (s, 9H), 0.006 (s, 3H), 0.00 (s, 3H). HRMS Calcd for $C_{15}H_{27}N_5OSi$ (M+H)$^+$ 322.2063. Found 322.2066.

Impure compound 25 (chromatographed once) is converted to 26 with the method used for 5 (2 eq. of monomethoxytrityl chloride used) and the TBDMS group of 26 is removed by the procedure used for 16. The resultant crude product is purified on a silica gel column using ethyl acetate:hexanes:methanol (1:1:0 to 1:1:0.2) as eluent to give 1.97 g (43%, three steps) of 27 as a white solid: $^1$H NMR (DMSO-$d_6$): δ 8.33 (s, 1H), 7.94 (s, 1H), 7.38-7.22 (m, 13H), 6.89 (d, J=9.0 Hz, 2H), 4.82-4.73 (m, 1H), 4.59 (t, J=5.1 Hz, 1H), 3.76 (s, 3H), 3.39-3.21 (m, 2H), 2.26-1.94 (m, 2H), 1.55 (d, J=6.8 Hz, 3H). IR (KBr, cm$^{-1}$) 3410, 2933, 1605, 1470 and 1250. Anal. Calcd for $C_{29}H_{29}N_6O_2 \cdot 0.2 H_2O$: C, 72.09; H, 6.13; N, 14.49. Found: C, 71.99; H, 6.20; N, 14.33.

EXAMPLE 20

(±)-9-[(1-Fluoromethyl)(3-(diisopropylphosphono)methoxy)propyl]-$N^6$-monomethoxytrityladenine (29). A solution of 8 (1.0 g, 1.48 mmol) in methylene chloride (20 mL) is treated with triethylamine (1.6 mL, 11.5 mmol) followed by DAST (0.6 mL, 4.54 mmol) and the reaction mixture stirred for 18 h at room temperature. This is then treated with 1M TBAF (3.7 mL, 3.7 mmol) and stirred for 6 days and then concentrated. The residue is purified on a silica gel column using ethyl acetate:hexanes:methanol (1:1:0 to 1:1:0.3) as eluent to give 0.232 g (23%) of 29 as a colorless oil and 0.567 g (57%) of the starting material recovered: $^1$H NMR (DMSO-$d_6$): δ 8.20 (s, 1H), 7.79 (s, 1H), 7.29-7.05 (m, 13H), 6.73 (d, J=9.0 Hz, 2H), 4.92-4.51 (m, 3H), 4.48-4.37 (m, 2H), 3.60 (s, 3H), 3.55 (dd, J=7.9, 2.1 Hz, 2H), 3.40-3.20 (m, 2H), 2.20-2.00 (m, 2H), 1.12-1.00 (m, 12H). IR (KBr, cm$^{-1}$) 3418, 2979, 1606, 1511 and 1472. Anal. Calcd for $C_{36}H_{43}FN_5O_5P \cdot 1.0 H_2O$: C, 62.33; H, 6.54; N, 10.10. Found: C, 62.56; H, 6.38; N, 10.29.

EXAMPLE 21

(±)-9-[(1-Tosyloxymethyl)(3-(diisopropylphosphono)methoxy)propyl]-$N^6$-monomethoxytrityladenine (30). A solution of 8 (1.18 g, 1.75 mmol) in pyridine (25 mL) is treated with 4-toluenesulphonyl chloride (0.681 g, 3.5 mmol) at 5° C. and the mixture is stirred for 15 h at room temperature. The reaction is not complete so more 4-toluenesulphonyl chloride (0.34 g, 0.18 mmol) is added and again stirred at room temperature for 8 h. The reaction mixture is diluted with EtOAc (300 mL), washed with water (2×) and brine, and dried over $MgSO_4$. After filtration and concentration, the residue is purified on a silica gel column using ethyl acetate:hexanes:methanol (1:1:0 to 1:1:0.2) as eluent to give 1.11 g (76%) of product as a white solid: $^1$H NMR (DMSO-$d_6$): δ 8.03 (s, 1H), 7.55 (s, 1H), 7.26-6.97 (m, 17H), 6.72 (d, J=9.0 Hz, 2H), 4.71-4.59 (m, 1H), 4.45-4.20 (m, 4H), 3.56 (s, 3H), 3.50-3.42 (m, 2H), 3.30-3.08 (m, 2H), 2.14 (s, 3H), 2.07-1.93 (m, 2H), 1.10-0.95 (m, 12H). IR (KBr, cm$^{-1}$) 3419, 2980, 1606, 1472 and 1250. Anal. Calcd for $C_{43}H_{50}N_5O_8SP \cdot 0.25\ H_2O \cdot 0.01$ EtOAc: C, 61.96; H, 6.15; N, 8.33. Found: C, 61.87; H, 6.04; N, 8.17.

EXAMPLE 22

(±)-9-[(1-Methylene)(3-(diisopropylphosphono)methoxy)propyl]-$N^6$-monomethoxytrityladenine (31). A solution of 30 (1.06 g, 1.28 mmol) in DMF (3.0 mL) is treated with sodium iodide (0.485 g, 3.20 mmol) and heated at 50° C. for 6 h. The solution is cooled to room temperature and DBU (0.294 g, 1.93 mmol) in DMF (0.5 mL) added and heated at 80° C. for 3 h. The solution on cooling is diluted with ethyl acetate (100 mL), washed with water and brine and dried over MgSO$_4$. After filtration, the filtrate is concentrated and the residue purified on a silica gel column using ethyl acetate:methanol (19:0 to 19:1) as eluent to give 0.694 g (82%) of product as a pale yellow oil: $^1$H NMR (CDCl$_3$): δ 8.06 (s, 1H), 7.86 (s, 1H), 7.45-7.15 (m, 13H), 6.80 (d, J=8.9 Hz, 2H), 5.47 (s, 1H), 5.27 (s, 1H), 4.80-4.66 (m, 2H), 3.78 (s, 3H), 3.80-3.64 (m, 4H), 3.07 (t, J=5.84 Hz, 2H), 1.35-1.26 (m, 12H). IR (neat, cm$^{-1}$) 3020, 1604, 1471, 1216 and 766. Anal. Calcd for $C_{36}H_{42}N_5O_5P \cdot 0.25\ H_2O \cdot 0.25$ EtOAc: C, 65.14; H, 6.57; N, 10.27. Found: C, 65.26; H, 6.52; N, 10.15.

EXAMPLE 23

(±)-9-[(1-Monomethoxytrityloxymethyl)(3-phosphonomethoxy)propyl]-$N^6$-monomethoxytrityladenine (32a). A suspension of 7 (16.7 g, 17.7 mmol) in DMF (170 mL) is treated with triethylamine (15 mL) followed by trimethylsilyliodide (25 mL, 174.9 mmol) and the reaction mixture flask covered with aluminum foil to protect from light and stirred for 14 h at room temperature. It is then diluted with TEAB buffer (500 mL), water (750 mL) and chloroform (1.5 L) and stirred for 1 h. The organic phase is collected and the aqueous phase extracted with chloroform (3×). The combined organic extracts are dried over MgSO$_4$. After filtration, the filtrate is concentrated and the residue purified on a silica gel column using chloroform:methanol (1:0 to 85:15), then CMA-80:CMA-50 (1:0 to 0:1) as eluent to give 7.0 g (46%) of 32a as a yellow solid: $^1$H NMR (DMSO-$d_6$): δ 8.29 (s, 1H), 7.67 (s, 1H), 7.30-6.81 (m, 25H), 6.75 (d, J=9.1 Hz, 2H), 6.65 (d, J=9.1 Hz, 2H), 4.78-4.65 (m, 1H), 3.61 (s, 3H), 3.60 (s, 3H), 3.40-2.99 (m, 6H), 2.36-2.20 (m, 1H), 2.04-1.87 (m, 1H). HRMS Calcd for $C_{50}H_{48}N_5O_7P$ (M+H)$^+$ 862.3369. Found 862.3409.

EXAMPLE 24

(±)-9-[(1-Methoxymethyl)(3-phosphonomethoxy)propyl]-$N^6$-monomethoxytrityladenine (32b). A solution of 8 (0.5 g, 0.74 mmol) in DMF (6.0 mL) is treated with sodium hydride (60%, 0.12 g, 3.0 mmol) at room temperature and the mixture stirred for 0.5 h. To this mixture is then added a solution of methyliodide (0.125 g, 0.88 mmol) in DMF (1 mL) and the mixture stirred at room temperature for 12 h. The reaction mixture is diluted with ethyl acetate (15 mL), neutralized with acetic acid and chloroform (200 mL) added. The mixture is washed with water (2×) and brine and the organic layer dried over MgSO$_4$ followed by filtration and concentration. The residue containing 9 is converted to 32b with the same procedure used for 32a. The product is purified on a silica gel column using chloroform:methanol (1:0 to 85:15), then CMA-80:CMA-50 (1:0 to 0:1) as eluent to give 222 mg (50%, two steps) of 32b as an off-white film: $^1$H NMR (DMSO-$d_6$): δ 8.31 (s, 1H), 7.87 (s, 1H), 7.38-7.16 (m, 13H), 6.84 (d, J=8.9 Hz, 2H), 4.86-4.75 (m, 1H), 4.02-3.93 (m, 1H), 3.73-3.13 (m, 5H), 3.71 (s, 3H), 3.16 (s, 3H), 2.15-2.03 (m, 2H). HRMS Calcd for $C_{31}H_{34}N_5O_6P$ (M+H)$^+$ 604.2325. Found 604.2345.

EXAMPLE 25

(±)-9-[(1-Azidomethyl)(3-phosphonomethoxy)propyl]-$N^6$-monomethoxytrityladenine (32c). It is prepared from 11 (345 mg) with the same procedure as given for 32a. The product is purified on a silica gel column using chloroform:methanol (1:0 to 85:15), then CMA-80:CMA-50 (1:0 to 0:1) as eluent to give 32c as a colorless film (yield, 63%): H NMR (DMSO-$d_6$): δ 8.39 (s, 1H), 7.89 (s, 1H), 7.37-7.11 (m, 13H), 6.84 (d, J=9.0 Hz, 2H), 4.85-4.74 (m, 1H), 4.11 (dd, J=11.7, 9.7 Hz, 1H), 3.87 (dd, J=14.2, 4.1 Hz, 1H), 3.71 (s, 3H), 3.49-3.37 (m, 1H), 3.32-3.12 (m, 3H), 2.23-2.06 (m, 2H). HRMS Calcd for $C_{30}H_{31}N_8O_5P$ (M+H)$^+$ 615.2233. Found 615.2226.

EXAMPLE 26

(±)-9-[(1-N-Monomethoxytritylaminomethyl)(3-phosphonomethoxy)propyl]-$N^6$-monomethoxytrityladenine (32d). It is prepared from 13 (540 mg) with the same procedure as given for 32a. The crude product is purified on a silica gel column using chloroform:methanol (1:0 to 85:15), then CMA-80:CMA-50 (1:0 to 0:1) as eluent to give 32d as a colorless film (yield, 52%): $^1$H NMR (DMSO-$d_6$): δ 8.33 (s, 1H), 7.80 (s, 1H), 7.41-6.92 (m, 25H), 6.84 (d, J=9.0 Hz, 2H), 6.69 (d, J=8.8 Hz, 2H), 4.74-4.61 (m, 1H), 3.69 (s, 3H), 3.67 (s, 3H), 3.34-2.32 (m, 7H), 2.16-2.04 (m, 1H), 1.96-1.84 (m, 1H). HRMS Calcd for $C_{50}H_{49}N_6O_6P$ (M+H)$^+$ 861.3529. Found 861.3568.

EXAMPLE 27

(±)-9-[(1-Methyl)(3-phosphonomethoxy)propyl]-$N^6$-monomethoxytrityladenine (32f). Compound 27 (1.87 g) is converted to 28 with the same method used for compound 7 and the resultant 28 is converted to 32f following the same procedure used for 32a. The residue is purified on a silica gel column using chloroform:methanol (1:0 to 85:15), then CMA-80:CMA-50 (1:0 to 0:1) as eluent to give 760 mg (34%, two steps) of 32f as a colorless film: $^1$H NMR (DMSO-$d_6$): δ 8.33 (s, 1H), 7.88 (s, 1H), 7.35-7.13 (m, 13H), 6.83 (d, J=9.0 Hz, 2H), 4.79-4.66 (m, 1H), 3.70 (s, 3H), 3.45-3.31 (m, 1H), 3.31-3.12 (m,3H), 2.23-2.10 (m, 1H), 2.10-1.97 (m, 1H), 1.51 (d, J=6.8 Hz, 3H). HRMS Calcd for $C_{30}H_{32}N_5O_5P$ (M+H)$^+$ 574.2219. Found 574.2243.

EXAMPLE 28

(±)-9-[(1-Methylene)(3-phosphonomethoxy)propyl]-$N^6$-monomethoxytrityladenine (32h). It is prepared from 31 (597 mg) with the same procedure as given for 32a. The crude product is purified on a silica gel column using chloroform:methanol (1:0 to 85:15), then CMA-80:CMA-50

(1:0 to 0:1) as eluent to give 32h as an off-white solid (yield, 57%): $^1$H NMR (DMSO-d$_6$): δ 8.41 (s, 1H), 7.92 (s, 1H), 7.40-7.15 (m, 13H), 6.84 (d, J=8.9 Hz, 2H), 5.61 (s, 1H), 5.25 (s, 1H), 3.70 (s, 3H), 3.57 (t, J=6.3 Hz, 2H), 3.31 (d, J=8.3 Hz, 2H), 2.96 (t, J=6.3 Hz, 2H). HRMS Calcd for C$_{30}$H$_{30}$N$_5$O$_5$P (M+H)$^+$ 572.2062. Found 572.2084.

EXAMPLE 29

Butyloxycarbonylmethylphosphono)methoxy)propyl]-N$^6$-monomethoxytrityladenine (33a). A solution of 32a (500 mg, 0.58 mmol) in DMF (31 mL) is treated with triethylamine (31 mL) followed by chloromethyl pivalate (11.2 mL, 76.93 mmol) and stirred for 3 days at room temperature. It is then diluted with chloroform (300 mL) and washed with water (2×). The organic layer is dried over MgSO$_4$. After filtration, the filtrate is concentrated and the residue purified on a silica gel column using ethyl acetate:hexanes:methanol (1:1:0 to 1:1:0.1) as eluent to give 174 mg (28%) of 33a as a colorless film: $^1$H NMR (DMSO-d$_6$): δ 8.13 (s, 1H), 7.54 (s, 1H), 7.14-6.65 (m, 25H), 6.60 (d, J=9.1 Hz, 2H), 6.51 (d, J=9.1 Hz, 2H), 5.38-5.26 (m, 4H), 4.57-4.43 (m, 1H), 3.59-3.40 (m, 2H), 3.46 (s, 6H), 3.25-2.85 (m, 44H), 2.29-2.17 (m, 1H), 1.91-1.76 (m, 1H), 0.88 (s, 18H). HRMS Calcd for C$_{62}$H$_{68}$N$_5$O$_{11}$P (M+H)$^+$ 1090.4731. Found 1090.4761.

EXAMPLE 30

(±)-9-[(1-Methoxymethyl)(3-(di-tert-butyloxycarbonylmethylphosphono)methoxy)propyl]-N$^6$-monomethoxytrityladenine (33b). It is prepared from 32b (160 mg) with the same procedure as given for 33a. The crude product is purified on a silica gel column using ethyl acetate:hexanes:methanol (1:1:0 to 1:1:0.1) as eluent to give 33b as a colorless film (yield, 63%): $^1$H NMR (DMSO-d$_6$): δ 8.16 (s, 1H), 7.82 (s, 1H), 7.30-7.10 (m, 13H), 6.78 (d, J=8.8 Hz, 2H), 5.58-5.48 (m, 4H), 4.73-4.62 (m, 1H), 3.86-3.73 (m, 1H), 3.76 (d, J=7.5 Hz, 2H), 3.65 (s, 3H), 3.60-3.53 (m, 1H), 3.43-3.23 (m, 2H), 3.13 (s, 3H), 2.23-1.97 (m, 2H), 1.07 (s, 18H). HRMS Calcd for C$_{43}$H$_{54}$N$_5$O$_{10}$P (M+H)$^+$ 832.3686. Found 832.3707.

EXAMPLE 31

(±)-9-[(1-Azidomethyl)(3-(di-tert-butyloxycarbonylmethylphosphono)methoxy)propyl]-N$^6$-monomethoxytrityladenine (33c). It is prepared from 32c (174 mg) with the same procedure as given for 33a. The crude product is purified on a silica gel column using ethyl acetate:hexanes:methanol (1:1:0 to 1:1:0.1) as eluent to give 33c as a colorless film (yield, 56%): $^1$H NMR (CDCl$_3$): δ 8.00 (s, 1H), 7.87 (s, 1H), 7.38-7.20 (m, 13H), 6.79 (d, J=9.0 Hz, 2H), 5.75-5.62 (m, 4H), 4.78-4.65 (m, 1H), 4.13 (dd, J=12.7, 8.2 Hz, 1H), 3.81-3.57 (m, 4H), 3.78 (s, 3H), 3.34-3.20 (m, 1H), 2.50-2.35 (m, 1H), 2.30-2.16 (m, 1H), 1.23 (s, 9H), 1.226 (s, 9H). HRMS Calcd for C$_{42}$H$_{51}$N$_8$O$_9$P (M+H)$^+$ 843.3594. Found 843.3558.

EXAMPLE 32

(±)-9-[(1-N-Monomethoxytritylaminomethyl)(3-(di-tert-butyloxycarbonylmethylphosphono)methoxy)propyl]-N$^6$-monomethoxytrityladenine (33d). It is prepared from 32d (150 mg) with the same procedure as given for 33a. The crude product is purified on a silica gel column using ethyl acetate:hexanes:methanol (1:1:0 to 1:1:0.1) as eluent to give 33d as a colorless film (yield, 48%): $^1$H NMR (CDCl$_3$): δ 7.964 (s, 1H), 7.958 (s, 1H), 7.47-6.95 (m, 25H), 6.78 (d, J=8.9 Hz, 2H), 6.68 (d, J=8.8 Hz, 2H), 5.76-5.60 (m, 4H), 4.66-4.52 (m, 1H), 4.20-4.02 (m, 1H), 3.79-3.65 (m, 2H), 3.72 (s, 6H), 3.58-3.44 (m, 1H), 3.31-3.16 (m, 1H), 2.88 (t, J=10.8 Hz,1H), 2.60-2.44 (m, 1H), 2.44-2.32 (m, 1H), 2.12-2.00 (m, 1H), 1.20 (m, 18H). HRMS Calcd for C$_{62}$H$_{69}$N$_6$O$_{10}$P (M+H)$^+$ 1089.4891. Found 1089.4859.

EXAMPLE 33

(±)-9-[(1-(2-Monomethoxytrityloxy)ethyl)(3-(di-tert-butyloxycarbonylmethylphosphono)methoxy)propyl]-N$^6$-monomethoxytrityladenine (33e). The conversions of 22 (427 mg) to 23, 23 to 32e and 32e to 33e are done by the methods used for 7, 32a and 33a, respectively. The residue is purified on a silica gel column using ethyl acetate: hexanes:methanol (1:1:0 to 1:1:0.1) as eluent to give 21 mg (3.5%, three steps) of 33e as a colorless film: $^1$H NMR (a mixture of diastereomers, CDCl$_3$): δ 8.06, 7.89, 7.82 (3s, 2H), 7.43-7.05 (m, 25H), 6.92-6.66 (m, 4H), 5.73-5.60 (m, 4H), 5.00-4.02, 3.86-3.02 (2m, 6H), 3.78 (s, 3H), 3.72 (s, 3H), 2.69-2.24 (m, 2H), 1.22, 1.21 (2s, 18H), 0.99, 0.94 (2d, J=6.6 Hz each, 3H). HRMS Calcd for C$_{63}$H$_{70}$N$_5$O$_{11}$P (M+H)$^+$ 1104.4887. Found 1104.4925.

EXAMPLE 34

(±)-9-[(1-Methyl)(3-(di-tert-butyloxycarbonylmethylphosphono)methoxy)propyl]-N$^6$-monomethoxytrityladenine (33f). It is prepared from 32f (240 mg) with the same procedure as given for 33a. The crude product is purified on a silica gel column using ethyl acetate:hexanes:methanol (1:1:0 to 1:1:0.1) as eluent to give 33f as a colorless oil (yield, 47%): $^1$H NMR (DMSO-d$_6$): δ 8.10 (s, 1H), 7.72 (s, 1H), 7.17-7.00 (m, 13H), 6.68 (d, J=9.1 Hz, 2H), 5.46-5.38 (m, 4H), 4.54-4.45 (m, 1H), 3.65 (d, J=7.7 Hz, 2H), 3.55 (s, 3H), 3.32-3.10 (m, 2H), 2.14-1.84 (m, 2H), 1.35 (d, J=6.8 Hz, 3H), 0.97 (s, 18H). IR (KBr, cm$^{-1}$) 3410, 2976, 1755, 1605, 1473and 1252. Anal. Calcd for C$_{42}$H$_{52}$N$_5$O$_9$P: C, 62.91; H, 6.54; N, 8.73. Found: C, 62.65; H, 6.76; N, 8.74.

EXAMPLE 35

(±)-9-[(1-Fluoromethyl)(3-(di-isopropyloxycarbonyloxymethylphosphono)methoxy)propyl]-N$^6$-monomethoxytrityladenine (33g). Compound 29 (210 mg) is converted to 32g and 32g to 33g with the methods used for 32a and 33a, respectively. In this case (32g to 33g), chloromethyl-2-propylcarbonate is used in place of chloromethyl pivalate. The time of the reaction also increased to 7 days. The purification gives the desired 33g in 29% yield: $^1$H NMR (CDCl$_3$): δ 7.94 (s, 1H), 7.82 (s, 1H), 7.31-7.12 (m, 13H), 6.73 (d, J=9.0 Hz, 2H), 5.69-5.55 (m 4H), 5.05-4.51 (m, 5H), 3.75 (d, J=7.9 Hz, 2H), 3.71 (s, 3H), 3.64-3.54 (m, 1H), 3.35-3.24 (m, 1H), 2.41-2.26 (m, 1H), 2.26-2.11 (m, 1H), 1.24 (d, J=6.2 Hz, 6H), 1.23 (d, J=6.2 Hz, 6H). HRMS Calcd for C$_{40}$H$_{47}$FN$_5$O$_{11}$P (M+H)$^+$ 824.3072 Found 824.3096.

EXAMPLE 36

(±)-9-[(1-Methylene)(3-(di-tert-butyloxycarbonylmethylphosphono)methoxy)propyl]-N$^6$-monomethoxytrityladenine (33h). It is prepared from 32h (193 mg) with the same procedure as given for 33a. The crude product is purified on a silica gel column using ethyl acetate:hexanes:methanol (1:1:0 to 1:1:0.1) as eluent to give 33h as a colorless oil (yield, 55%): $^1$H NMR (DMSO-d$_6$): δ 8.58 (s, 1H), 8.16 (s, 1H), 7.62-7.41 (m, 13H), 7.08 (d, J=8.9 Hz, 2H), 5.86 (s, 1H), 5.84 (d, J=1.5 Hz, 2H), 5.79 (d, J=1.1 Hz, 2H), 5.46 (s, 1H), 4.12 (d, J=7.8 Hz, 2H), 3.95 (s, 3H), 3.85 (t, J=6.4 Hz, 2H), 3.26 (d, J=6.4 Hz, 2H), 1.37 (s, 18H). IR (neat, cm$^{-1}$) 3020, 1753, 1604 and 1216. Anal. Calcd for C$_{42}$H$_{50}$N$_5$O$_9$P.0.25 H$_2$O: C, 62.71; H, 6.33; N, 8.71. Found: C, 62.92; H, 6.70; N, 8.62.

EXAMPLE 37

(±)-9-[(1-Monomethoxytrityloxymethyl)(3-(di-isopropyloxycarbonyloxymethyl-phosphono)methoxy)propyl]-N$^6$-monomethoxytrityladenine (33i). It is prepared from 32a (216 mg) with the same procedure as given for 33a but using chloromethyl-2-propylcarbonate in place of chloromethyl pivalate. The time of the reaction is also increased to 7 days. The crude product is purified on a silica gel column using ethyl acetate:hexanes:methanol (1:1:0 to 1:1:0.1) as eluent to give 33i as a colorless film (yield, 50%): $^1$H NMR (CDCl$_3$): δ 7.99 (s, 1H), 7.90 (s, 1H), 7.41-7.00 (m, 25H), 6.79 (d, J=8.9 Hz, 2H), 6.70 (d, J=8.7 Hz, 2H), 5.73-5.58 (m, 4H), 4.96-4.86 (m, 2H), 4.81-4.71 (m, 1H), 3.79-3.66 (m, 3H), 3.76 (s, 3H), 3.75 (s, 3H), 3.56-3.48 (m, 1H), 3.34-3.24 (m, 2H), 2.58-2.45 (m, 1H), 2.18-2.06 (m, 1H), 1.32-1.24 (m, 12H). HRMS Calcd for C$_{60}$H$_{64}$N$_5$O$_{13}$P (M+H)$^+$ 1094.4316. Found 1094.4316.

EXAMPLE 38

(±)-9-[(1-Methoxymethyl)(3-(di-isopropyloxycarbonyloxymethylphosphono)methoxy)-propyl]-N$^6$-monomethoxytrityladenine (33j). It is prepared from 32b (115 mg) with the same procedure as given for 33i. The crude product is purified on a silica gel column using ethyl acetate:hexanes:methanol (1:1:0 to 1:1:0.1) as eluent to give 33j as a colorless film (yield, 42%): $^1$H NMR (CDCl$_3$): δ 8.01 (s, 1H), 7.90 (s, 1H), 7.39-7.19 (m, 13H), 6.80 (d, J=9.0 Hz, 2H), 5.75-5.64 (m, 4H), 4.99-4.87 (m, 2H), 4.87-4.77 (m, 1H), 3.94 (dd, J=10.3, 6.7 Hz, 1H), 3.81 (d, J=7.9 Hz, 2H), 3.78 (s, 3H), 3.66 (dd, J=9.8, 3.8 Hz, 1H), 3.63-3.56 (m, 1H), 3.41-3.32 (m, 1H), 3.32 (s, 3H), 2.43-2.12 (m, 2H), 1.31 (d, J=6.3 Hz, 6H), 1.30 (d, J=6.2 Hz, 6H). HRMS Calcd for C$_{41}$H$_{50}$N$_5$O$_{12}$P (M+H)$^+$ 836.3271. Found 836.3235.

EXAMPLE 39

(±)-9-[(1-Hydroxymethyl)(3-(di-tert-butyloxycarbonylmethylphosphono)methoxy)propyl]-adenine (34a). A solution of 33a (272 mg, 0.25 mmol) in acetonitrile (54 mL) is treated with 0.2 M HCl (2.7 mL) and stirred for 14 h at room temperature. It is then carefully neutralized with 0.5 N NaOH to pH 6.0 and diluted with water (20 mL) and concentrated to remove acetonitrile. The residual material is again diluted with water (20 mL) and extracted with chloroform:methanol (4:1, 2×). The organic layer is dried over MgSO$_4$. After filtration, the filtrate is concentrated and the residue purified on a silica gel column using chloroform:methanol (1:0 to 9:1) as eluent to give 102 mg (75%) of 34a as a colorless oil. HPLC: R$_t$=22.240 min., 97.06%.

Procedure for the fumarate salt of 34a: A solution of 34a (50.0 mg, 0.092 mmol) in 2-propanol (0.25 mL) is treated with a solution of fumaric acid in propanol (20.3 mg/mL, 1.62 mL, 0.092 mmol) followed by concentration. The fumaric salt is obtained as a white solid: $^1$H NMR (DMSO-d$_6$): δ 13.21 (bs, 2H), 8.16 (s, 1H), 8.15 (s, 2H), 7.25 (s, 2H), 6.69 (s, 2H), 5.70-5.60 (m, 4H), 5.11 (bs, 1H), 4.68-4.52 (m, 1H), 4.00-3.70 (m, 2H), 3.87 (d, J=7.7 Hz, 2H), 3.53-3.30 (m, 2H), 2.35-2.13 (m, 2H), 1.20 (s, 18H). Anal. Calcd for C$_{22}$H$_{36}$N$_5$O$_9$P.1.0 C$_4$H$_4$O$_4$: C, 47.18; H, 6.10; N, 10.59. Found: C, 47.30; H, 6.11; N, 10.31.

EXAMPLE 40

(±)-9-[(1-Methoxymethyl)(3-(di-tert-butyloxycarbonylmethylphosphono)methoxy)propyl]-adenine (34b). It is prepared from 33b (110 mg) with the same procedure as given for 34a. The crude product was purified on a silica gel column using chloroform:methanol (1:0 to 9:1) as eluent to give 34b as a colorless oil (yield, 49%): $^1$H NMR (CDCl$_3$): δ 8.30 (s, 1H), 7.96 (s, 1H), 5.84 (s, 2H), 5.75-5.63 (m, 4H), 4.92-4.80 (m, 1H), 3.93 (dd, J=10.0, 6.2 Hz, 1H), 3.75 (dd, J=7.9, 1.3 Hz, 1H), 3.67 (dd, J=10.2, 3.8 Hz, 1H), 3.64-3.56 (m, 1H), 3.37-3.30 (m, 1H), 3.38-3.28 (m, 1H), 3.32 (s, 3H), 2.44-2.30 (m, 1H), 2.30-2.16 (m, 1H), 1.23 (s, 9H), 1.22 (s, 9H). IR (neat, cm$^{-1}$) 3020, 2982, 1751, 1631, 1478 and 1216. HRMS Calcd for C$_{23}$H$_{38}$N$_5$O$_9$P (M+H)$^+$ 560.2485. Found 560.2468.

EXAMPLE 41

(±)-9-[(1-Azidomethyl)(3-(di-tert-butyloxycarbonylmethylphosphono)methoxy)propyl]-adenine (34c). It is prepared from 33c (117 mg) with the same procedure as given for 34a. The crude product is purified on a silica gel column using chloroform:methanol (1:0 to 9:1) as eluent to give 34c as a colorless oil (yield, 83%): $^1$H NMR (CDCl$_3$): δ 8.30 (s, 1H), 7.91 (s, 1H), 5.80-5.62 (m, 6H), 4.84-4.70 (m, 1H), 4.23-4.12 (m, 1H), 3.83-3.69 (m, 3H), 3.67-3.56 (m, 1H), 3.34-3.21 (m, 1H), 2.56-2.40 (m, 1H), 2.32-2.16 (m, 1H), 1.24 (s, 9H), 1.23 (s, 9H). IR (neat, cm$^{-1}$) 3019, 2980, 2106, 1751 and 1633. HRMS Calcd for C$_{22}$H$_{35}$N$_8$O$_8$P (M+H)$^+$ 571.2393. Found 571.2386. HPLC: R$_t$=23.019 min., 95.64%.

EXAMPLE 42

(±)-9-[(1-Aminomethyl)(3-(di-tert-butyloxycarbonylmethylphosphono)methoxy)propyl]-adenine (34d). A solution of 33d (67 mg, 0.062 mmol) in acetonitrile (10 mL) is treated with 0.2 M HCl (0.5 mL) and stirred for 16 h at room temperature. It is diluted with water (150 mL) and extracted with ethyl acetate (2×). The aqueous layer is concentrated to dryness to give 34d as a gum. The product is dissolved in 3.5 mL of water and its concentration measured to be 13.07 mM (74%) by UV at 259 nm: $^1$H NMR (D$_2$O): δ 8.32 (s, 1H), 8.31 (s, 1H), 5.57-5.43 (m, 4H), 5.03-4.91 (m, 1H), 3.78-3.45 (m, 5H), 3.30-3.20 (m, 1H), 2.43-2.29 (m, 1H), 2.25-2.12 (m, 1H), 1.08 (s, 9H), 1.07 (s, 9H). HRMS Calcd for C$_{22}$H$_{37}$N$_6$O$_8$P (M+H)$^+$ 545.2488. Found 545.2476. HPLC: R$_t$=18.720 min., 95.61%.

EXAMPLE 43

(±)-9-[(1-(2-Hydroxy)ethyl)(3-(di-tert-butyloxycarbonylmethylphosphono)methoxy)propyl]-adenine (34e). It is prepared from 33e (21 mg) with the same procedure as given for 34a. The crude product is purified on a silica gel column using chloroform:methanol (1:0 to 9:1) as eluent to give 34e as a colorless oil (yield, 72%): $^1$H NMR (a mixture of diastereomers, CDCl$_3$): δ 8.29, 8.28, 7.96, 7.94 (4s, 2H), 6.06-5.65 (m, 7H), 4.64-4.14 (m, 2H), 3.89-3.50 (m, 3H), 3.14-3.00 (m, 1H), 2.37-2.17 (m, 2H), 1.33, 1.05 (d, J=6.7 Hz each, 3H), 1.234, 1.231 (2s, 18H). IR (neat, cm$^{-1}$) 3321, 3019, 1753, 1635 and 1216. HRMS Calcd for $C_{23}H_{38}N_5O_9P$ (M+H)$^+$ 560.2485. Found 560.2484. HPLC: $R_t$=21.865 min., 97.66%.

EXAMPLE 44

(±)-9-[(1-Methyl)(3-(di-tert-butyloxycarbonylmethylphosphono)methoxy)propyl]adenine (34f). It is prepared from 33f (127 mg) with the same procedure as given for 34a. The crude product is purified on a silica gel column using chloroform:methanol (1:0 to 9:1) as eluent to give 34f as a colorless oil (yield, 97%): $^1$H NMR (CDCl$_3$): δ 8.32 (s, 1H), 7.88 (s, 1H), 5.75-5.64 (m, 6H), 4.85-4.75 (m, 1H), 3.75 (d, J=7.9 Hz, 2H), 3.60-3.52 (m, 1H), 3.35-3.24 (m, 1H), 2.46-2.32 (m, 1H), 2.24-2.10 (m, 1H), 1.67 (d, J=6.8 Hz, 3H), 1.23 (s, 9H), 1.22 (s, 9H). IR (neat, cm$^{-1}$) 3020, 2981, 1751, 1630, 1478 and 1216. HRMS Calcd for $C_{22}H_{36}N_5O_8P$ (M+H)$^+$ 530.2379. Found 530.2356. HPLC: $R_t$=23.477 min., 99.03%.

EXAMPLE 45

(±)-9-[(1-Fluoromethyl)(3-(di-isopropyloxycarbonyloxymethylphosphono)methoxy)propyl]-adenine (34g). It is prepared from 33g (40 mg) with the same procedure as given for 34a. The crude product is purified on a silica gel column using chloroform:methanol (1:0 to 9:1) as eluent to give 34g as a light yellow oil (yield, 96%): $^1$H NMR (CDCl$_3$): δ 8.32 (s, 1H), 7.96 (s, 1H), 5.79 (s, 2H), 5.76-5.64 (m, 4H), 5.13-4.60 (m, 5H), 3.81 (d, J=7.8 Hz, 2H), 3.72-3.63 (m, 1H), 3.38-3.30 (m, 1H), 2.50-2.36 (m, 1H), 2.35-2.20 (m, 1H), 1.32 (d, J=6.3 Hz, 6H), 1.31 (d, J=6.4 Hz, 6H). IR (neat, cm$^{-1}$) 3334, 2987, 1759, 1646, 1599 and 1268. HRMS Calcd for $C_{20}H_{31}FN_5O_{10}P$ (M+H)$^+$ 552.1870. Found 552.1847. HPLC: $R_t$=21.739 min., 98.59%.

EXAMPLE 46

(±)-9-[(1-Methylene)(3-(di-tert-butyloxycarbonylmethylphosphono)methoxy)propyl]-adenine (34h). It is prepared from 33h (135 mg) with the same procedure as given for 34a. The crude product is purified on a silica gel column using chloroform:methanol (1:0 to 9:1) as eluent to give 34h as a colorless oil (yield, 95%): $^1$H NMR (CDCl$_3$): δ 8.35 (s, 1H), 7.94 (s, 1H), 5.79 (s, 2H), 5.73-5.63 (m, 4H), 5.48 (s, 1H), 5.29 (s, 1H), 3.80 (d, J=7.9 Hz, 2H), 3.67 (t, J=6.2 Hz, 2H), 3.11 (t, J=6.2 Hz, 2H), 1.22 (s, 18H). IR (neat, cm$^{-1}$) 3019, 2981, 1751, 1633 and 1216. HRMS Calcd for $C_{22}H_{34}N_5O_8P$ (M+H)$^+$ 528.2223. Found 528.2207. HPLC: $R_t$=23.029 min., 95.79%.

EXAMPLE 47

(±)-9-[(1-Hydroxymethyl)(3-(di-isopropyloxycarbonyloxymethylphosphono)methoxy)-propyl]adenine (34i). It is prepared from 33i (122 mg) with the same procedure as given for 34a. The crude product is purified on a silica gel column using chloroform:methanol (1:0 to 9:1) as eluent to give 34i as a colorless film (yield, 69%): $^1$H NMR (CDCl$_3$): δ 8.22 (s, 1H), 7.90 (s, 1H), 5.73-5.58 (m, 6H), 4.87 (hept, J=6.2 Hz, 2H), 4.72-4.62 (m, 1H), 4.03 (bs, 2H), 3.88-3.69 (m, 2H), 3.65-3.57 (m, 1H), 3.23-3.14 (m, 1H), 2.26-2.17 (m, 2H), 1.25, 1.24 (2d, J=6.3 each, 12H). IR (neat, cm$^{-1}$) 3330, 2984, 1759, 1645, 1601 and 1472. HRMS Calcd for $C_{20}H_{32}N_5O_{11}P$ (M+H)$^+$ 550.1914. Found 550.1930. HPLC: $R_t$=20.352 min., 97.44%.

EXAMPLE 48

(±)-9-[(1-Methoxymethyl)(3-(di-isopropyloxycarbonyloxymethylphosphono)methoxy)-propyl]adenine (34j). It is prepared from 33j (60 mg) with the same procedure as given for 34a. The crude product is purified on a silica gel column using chloroform:methanol (1:0 to 9:1) as eluent to give 34j as a colorless oil (yield, 99%): $^1$H NMR (CDCl$_3$): δ 8.30 (s, 1H), 7.96 (s, 1H), 6.09 (s, 2H), 5.81-5.62 (m, 4H), 5.03-4.81 (m, 3H), 3.95 (dd, J=10.0, 6.4 Hz, 1H), 3.80 (d, J=7.7 Hz, 2H), 3.72-3.58 (m, 2H), 3.40-3.30 (m, 1H), 3.32 (s, 3H), 2.46-2.32 (m, 1H), 2.32-2.20 (m, 1H), 1.32 (d, J=6.2 Hz, 12H). IR (neat, cm$^{-1}$) 3020, 1761, 1631 and 1216. HRMS Calcd for $C_{21}H_{34}N_5O_{11}P$ (M+H)$^+$ 564.2070. Found 564.2060. HPLC: $R_t$=22.123 min., 96.91%.

EXAMPLE 49

(±)-9-[1-[(Diisopropylphosphono)methoxy]methyl][(1-monomethoxytrityloxy)-propyl]-N$^6$-monomethoxytrityladenine (35). A solution of 16 (72.45 g, 94.35 mmol) in DMF (810 mL) is treated with sodium hydride (60%, 15.1 g, 377.5 mmol) at room temperature and the mixture is stirred for 1 h. To this solution is added a solution of (di-isopropoxyphosphono)methyl tosylate (39.65 g, 113.17 mmol) in DMF (70 mL) and the mixture is stirred at room temperature for 15 h. The reaction mixture is diluted with ethyl acetate (3 L), neutralized with acetic acid and washed with water (2×) and brine and the organic layer is dried over MgSO$_4$. After filtration, the filtrate is concentrated and the residue is purified on a silica gel column using ethyl acetate:hexanes: methanol (1:1:0 to 1:1:0.1) as eluent to give 61.2 g (69%) of product as a white solid: $^1$H NMR (DMSO-d$_6$): δ 8.20 (s, 1H), 7.87 (s, 1H), 7.32-7.03 (m, 25H), 6.84 (d, J=8.9 Hz, 2H), 6.78 (d, J=8.9 Hz, 2H), 5.01-4.90 (m, 1H), 4.45-4.32 (m, 2H), 4.03-3.94 (m, 1H), 3.82-3.63 (m, 3H), 3.71 (s, 3H), 3.69 (s, 3H), 2.93-2.81 (m, 1H), 2.81-2.70 (m, 1H), 2.40-2.20 (m, 1H), 2.20-2.03 (m, 1H), 1.11 (d, J=6.2 Hz, 3H), 1.10 (d, J=6.2 Hz, 3H), 1.02 (d, J=6.3 Hz, 3H), 1.01 (d, J=6.2 Hz, 3H). IR (KBr, cm$^{-1}$) 3420, 2978, 1605, 1508 and 1250. Anal. Calcd for $C_{56}H_{60}N_5O_7P·0.5$ H$_2$O·0.25 EtOAc: C, 70.06; H, 6.50; N, 7.17. Found: C, 69.92; H, 6.55; N, 7.21.

EXAMPLE 50

(±)-9-[1-[(Diisopropylphosphono)methoxy]methyl][(3-hydroxy)propyl]-N$^6$-monomethoxytrityladenine (36). A solution of 35 (52.2 g, 55.18 mmol) in acetonitrile (2 L) is treated with conc. HCl (4 mL) at room temperature and the mixture is stirred for 24 h. The reaction is neutralized with 2N NaOH and diluted with water (250 mL). It is then concentrated to remove most of acetonitrile and treated with ethyl acetate (500 mL) and water (200 mL). The organic layer is separated and dried over MgSO$_4$. After filtration, the filtrate is concentrated and the residue is purified on a silica gel column using ethyl acetate:hexanes:methanol (1:1:0 to 1:1:0.2) as eluent to give 6.18 g (17%) of 36 as a white solid: $^1$H NMR (DMSO-d$_6$): δ 8.27 (s, 1H), 7.93 (s, 1H), 7.38-7.20 (m, 13H), 6.89 (d, J=9.0 Hz, 2H), 4.92-4.80 (m, 1H), 4.64 (t, J=5.1 Hz, 1H), 4.50-4.36 (m, 2H), 4.14 (t, J=9.8 Hz, 1H), 3.89-3.65 (m, 3H), 3.76 (s, 3H), 3.42-3.18 (m, 2H), 2.22-1.95 (m, 2H), 1.18-1.11 (m, 6H), 1.06 (d, J=6.2 Hz, 6H). IR (KBr, cm$^{-1}$) 3418, 2978, 1605, 1503 and 1250. Anal. Calcd for $C_{36}H_{44}N_5O_6P·0.5$ H$_2$O: C, 63.33; H, 6.64; N, 10.26. Found: C, 63.31; H, 6.47; N, 10.19.

EXAMPLE 51

(±)-9-[1-[(Diisopropylphosphono)methoxy]methyl][(3-azido)propyl]-N$^6$-monomethoxytrityladenine (38). A solution of 36 (1.00 g, 1.48 mmol) in pyridine (20 mL) is treated with methanesulphonyl chloride (539 mg, 97%, 3.00 mmol) and the mixture is stirred for 20 h at room temperature. The reaction mixture is diluted with ethyl acetate (200 mL), washed with water (2×) and brine and the organic layer dried over MgSO$_4$ followed by filtration and concentration. The residue containing 37 is dissolved in DMF (9 mL), treated with sodium azide (260 mg, 3.96 mmol) and the mixture stirred for 4 h at 100° C. The reaction mixture is diluted with ethyl acetate (300 mL), washed with water (2×) and brine and the organic layer dried over MgSO$_4$. After filtration, the filtrate is concentrated and the residue was purified on a silica gel column using ethyl acetate:hexanes:methanol (1:1:0 to 1:1:0.2) as eluent to give 458 mg (44%, two steps) of product as a colorless film: $^1$H NMR (CDCl$_3$): δ 8.04 (s, 1H), 7.89 (s, 1H), 7.40-7.18 (m, 13H), 6.79 (d, J=8.8 Hz, 2H), 4.87-4.76 (m, 1H), 4.73-4.60 (m, 2H), 4.19-3.68 (m, 4H), 3.77 (s, 3H), 3.41-3.32 (m, 1H), 3.22-3.10 (m, 1H), 2.47-2.32 (m, 1H), 2.24-2.12 (m, 1H), 1.29 (d, J=6.0 Hz, 6H), 1.24 (d, J=6.7 Hz, 6H). IR (neat, cm$^{-1}$) 3017, 2103, 1605 and 1216. HRMS Calcd for C$_{36}$H$_{43}$N$_8$O$_5$P (M+H)$^+$ 699.3172. Found: 699.3152.

EXAMPLE 52

(±)-9-[1-[(Diisopropylphosphono)methoxy]methyl][(3-amino)propyl]-N$^6$-monomethoxytrityladenine (39). A mixture of 38 (805 mg, 1.15 mmol) in THF (8 mL) and water (1.6 mL) is treated with triphenylphosphine (640 mg, 2.44 mmol) and stirred at room temperature for 14 h. The reaction mixture is concentrated and purified on silica gel column using chloroform:CMA-80 (1:0 to 1:1) as eluent to give 660 mg (85%) as a white solid: $^1$H NMR (DMSO-d$_6$): δ 8.09 (s, 1H), 7.72 (s, 1H), 7.17-7.00 (m, 13H), 6.67 (d, J=9.0 Hz, 2H), 4.70-4.59 (m, 1H), 4.28-4.16 (m, 2H), 3.95 (t, J=9.2 Hz, 1H), 3.68-3.45 (m, 3H), 3.54 (s, 3H), 2.29-2.05 (m, 2H), 1.93-1.60 (m, 4H), 0.96-0.91 (m, 6H), 0.84 (d, J=6.1 Hz, 6H). IR (neat, cm$^{-1}$) 3414, 3020, 1605, 1511 and 1216. Anal. Calcd for C$_{36}$H$_{45}$N$_6$O$_5$P.1.5 H$_2$O: C, 61.79; H, 6.91; N, 12.01. Found: C, 61.70; H, 6.63; N, 12.07.

EXAMPLE 53

(±)-9-[1-[(Diisopropylphosphono)methoxy]methyl][(3-monomethoxytritylamino)propyl]-N$^6$-monomethoxytrityladenine (40). A solution of compound 39 (600 mg, 0.89 mmol) in pyridine (5 mL) is treated with monomethoxytrityl chloride (561 mg, 1.78 mol) and the reaction mixture is heated at 70° C. with stirring for 16 h. It is diluted with ethyl acetate (150 mL) and washed with water (2×) and brine and the organic layer dried over MgSO$_4$. After filtration, the filtrate is concentrated and the residue is purified on a silica gel column using ethyl acetate:hexanes:methanol (1:1:0 to 1:1:0.1) as eluent (1:0 to 1:1) to give 645 mg (87%) of product as a light yellow film: $^1$H NMR (DMSO-d$_6$): δ 7.99 (s, 1H), 7.66 (s, 1H), 7.12-6.79 (m, 25H), 6.61 (d, J=9.0 Hz, 2H), 6.50 (d, J=9.1 Hz, 2H), 4.88-4.75 (m, 1H), 4.22-4.09 (m, 2H), 3.80-3.68 (m, 1H), 3.63-3.40 (m, 3H), 3.48 (s, 3H), 3.45 (s, 3H), 2.37-1.93 (m, 2H), 1.83-1.49 (m, 3H), 0.89-0.84 (m, 6H), 0.80-0.75 (m, 6H). IR (KBr, cm$^{-1}$) 3418, 2978, 1605, 1503, 1250 and 989. Anal. Calcd for C$_{56}$H$_{61}$N$_6$O$_6$P.0.5 H$_2$O: C, 70.50; H, 6.55; N, 8.81. Found: C, 70.38; H, 6.52; N, 8.72.

EXAMPLE 54

(±)-9-[1-(tert-Butyldiphenylsilyloxy)methyl]propyladenine (43). To a mixture of 42 (19 g, 55.5 mol), triphenylphosphine (29 g, 0.11 mol) and adenine (15 g, 0.11 mol) in anhydrous dioxane (300 mL) is added a solution of DIAD (21.8 mL) in dioxane (30 mL) over a period of 2 h at room temperature and the mixture stirred further for 16 h. The reaction mixture is evaporated to dryness and the residue is purified on a column of silica gel eluting with chloroform:methanol (100:0 to 95:5) to provide 20 g (81%) of 43 as a white foam: $^1$H NMR (DMSO-d$_6$): 7.99 (s, 1 H), 7.85 (s, 1 H), 7.4-7.00 (m, 12 H), 4.34 (m, 1 H), 3.82 (m, 1 H), 3.68 (m, 1 H), 1.87 (m, 1 H), 1.70 (m, 1 H), 0.58 (m, 12 H). IR (KBr, cm$^{-1}$) 3147, 2962, 2931, 2857, 1674, 1601, 1472 and 1303.

EXAMPLE 55

(±)-9-[1-(tert-Butyldiphenylsilyloxy)methyl]propyl-N$^6$-monomethoxytrityladenine (44). A solution of 43 (20 g, 0.044 mol) in pyridine (500 mL) is treated with MMTr-chloride (27.75 g, 0.088 mol) and the reaction mixture is heated at 70° C. with stirring for 20 h. It is evaporated to dryness, diluted with ethyl acetate (1.5 L) and washed with water (2×500 mL) and brine and the organic layer dried over MgSO$_4$. After filtration, the filtrate is concentrated and the residue was purified on a silica gel column using ethyl acetate:hexanes as eluent (1:0 to 1:1) to give 22 g (69%) of product as a yellow solid: $^1$H NMR (DMSO-d$_6$): δ 8.32 (s, 1 H), 7.84 (s, 1 H), 7.4-6.8 (m, 24 H), 4.55 (m, 1 H), 4.00 (m, 1 H), 3.88 (m, 1 H), 3.70 (s, 3 H), 2.09 (m, 1 H), 1.92 (m, 1 H), 0.77 (m, 12 H). IR (KBr, cm$^{-1}$) 2931, 2856, 2361, 1734, 1604, 1467, 1249 and 1111.

EXAMPLE 56

(±)-9-[1-Hydroxymethyl]propyl-N$^6$-monomethoxytrityladenine (45). Compound 44 (22 g, 30.0 mmol) is dissolved in THF (200 L) and treated with TBAF (1M in THF, 30.68 mL) and the reaction mixture is stirred at room temperature for 2 h followed by concentration. The residue is purified on a silica gel column using chloroform:methanol (100:0 to 90:10) as an eluent to give 10g (70%) of 45 as a white foam, mp 188° C.: $^1$H NMR (DMSO-d$_6$): δ: 8.23 (s, 1 H), 7.89 (s, 1 H), 7.4-6.9 (m, 14 H), 5.01 (bs, 1 H), 4.36 (m, 1 H), 3.84 (m, 1 H), 3.71 (s, 3 H), 3.67 (m, 1 H, partially masked by CH$_3$ peak), 1.90 (m, 2 H), 0.73 (t, J=7.3 Hz, 3H). IR (KBr, cm$^{-1}$) 3408, 3313, 2966, 1715, 1605, 1469 and 1249.

EXAMPLE 57

(±)-9-[1-[(Monomethoxytrityloxy)methyl][3-oxopropyl]-N$^6$-monomethoxytrityladenine (47). A solution of 6 (4.16 g, 5.42 mmol) in methylene chloride (300 mL) is treated with Dess-Martin reagent (4.74 g, 97%, 10.84 mmol) and stirred at room temperature for 4 h. The reaction mixture is concentrated and purified on a silica gel column using ethyl acetate:hexanes (1:0 to 1:2) as eluent to provide 2.9 g (70%) of 47 as a white solid: $^1$H NMR (DMSO-d$_6$): δ 9.58 (s, 1H), 8.44 (s, 1H), 7.80 (s, 1H), 7.43-6.67 (m, 29H), 5.24-5.12 (m, 1H), 4.08-3.89 (m, 1H), 3.70 (s, 6H), 3.65-3.48 (m, 1H), 3.18 (d, J=10.3 Hz, 2H). MS (ES$^+$) 766.58 (M+H)$^+$.

EXAMPLE 58

(±)-9-[1-[(tert-Butyldimethylsilyloxy)methyl][(3-hydroxy)butyl]adenine (50). A solution of 47 (2.8 g, 3.66 mmol) in THF (150 mL) is treated with 3M methyl magnesium bromide (6.1 mL, 18.3 mmol) and the mixture is stirred for 6 h at room temperature. The reaction mixture is diluted with ethyl acetate (400 mL) and washed with water (2×) and brine and the organic layer dried over $MgSO_4$. After filtration and concentration, a white solid (48) is obtained (2.65 g).

A solution of 48 (2.55 g, 3.26 mmol) in acetonitrile (300 mL) and water (14 mL) is treated with 2M HCl (1.5 mL) at room temperature and the mixture is stirred for 14 h. The reaction mixture is neutralized by adding 0.5N NaOH followed by dilution with water (100 mL) and concentration to remove most of the organic solvent. The aqueous phase is extracted with ethyl acetate (2×100 mL) and concentrated to give 830 mg of 49 as light yellow film.

To a solution of 49 in DMF (8 mL) is added imidazole (375 mg, 5.45 mmol) and TBDMS-chloride (332 mg, 2.18 mmol) and stirred at room temperature for 31 h. The reaction mixture is diluted with chloroform (300 mL), washed with water (2×) and dried over $MgSO_4$. After filtration, the filtrate is concentrated and the residue is purified on a silica gel column using chloroform:CMA-80 (1:0 to 1:1) to give 338 mg (49%) of 50 as a colorless film: $^1H$ NMR (a mixture of diastereomers, $CDCl_3$): δ 8.28, 8.275, 8.12, 7.93 (4s, 2H), 5.79, 5.76 (2s, 2H), 4.85-4.75 (m, 1H), 4.01 (d, J=3.8 Hz, 2H), 3.88-3.76, 3.28-3.18 (2m, 2H), 2.18-1.98, 1.73-1.62 (2m, 2H), 1.19, 1.10 (2d, J=6.2 Hz each, 3H), 0.83, 0.78 (2s, 9H), 0.00, −0.11, −0.12 (3s, 6H). HRMS Calcd for $C_{16}H_{29}N_5O_2Si$ $(M+H)^+$ 352.2168. Found: 352.2177.

EXAMPLE 59

(±)-9-[1-(Hydroxymethyl)[(3-monomethoxytriyloxy)butyl]-$N^6$-monomethoxytritladenine (52). A solution of 50 (320 mg, 0.91 mmol) in pyridine (5 mL) is treated with monomethoxytrityl chloride (1.15 g, 98%, 3.65 mmol) and the reaction mixture heated at 70° C. with stirring for 14 h. It is diluted with ethyl acetate (150 mL) and washed with water (2×) and brine and the organic layer dried over $MgSO_4$. After filtration, the filtrate is concentrated and the residue purified on a silica gel column using ethyl acetate: hexanes as eluent (1:0 to 3:1) to give 1.07 g of 51 as a colorless syrup.

A solution of 51 in THF (9 mL) is treated with TBAF (1M in THF, 0.91 mL) and the reaction mixture is stirred at room temperature for 2 h followed by concentration. The residue is purified on a silica gel column using ethyl acetate: hexanes:methanol (1:1:0 to 1:1:0.1) to give 507 mg (71%, two steps) of 52 as a white solid: $^1$HNMR (a mixture of diastereomers, DMSO-$d_6$): δ 8.11, 7.94, 7.91, 7.85 (4s, 2H), 7.39-7.13 (m, 25H), 6.93-6.75 (m, 4H), 5.02 (t, J=5.8 Hz, 1H), 4.72-4.64, 4.52-4.44 (2m, 1H), 3.77, 3.76, 3.75, 3.73 (4s, 6H), 3.71-3.51, 3.31-3.11 (2m, 3H), 2.27-2.14, 1.99-1.72 (2m, 2H), 0.81, 0.70, (2d, J=6.0 Hz each, 3H). IR (KBr, $cm^{-1}$) 3414, 2931, 1606, 1508 and 1250. Anal. Calcd for $C_{50}H_{47}N_5O_4 \cdot 0.3$ EtOAc: C, 76.07; H, 6.16; N, 8.66. Found: C, 75.92; H, 6.29; N. 8.59.

EXAMPLE 60

(±)-9-[1-[(Diisopropylphosphonomethoxy)methyl][(3-monomethoxytriyloxy)butyl]-$N^6$-monomethoxytritladenine (53). It is prepared from 52 with the same procedure as given for 35. The crude product is purified on a silica gel column using ethyl acetate:hexanes:methanol (1:1:0 to 1:1: 0.1) as eluent to give 53 in 57% yield as a colorless oil: $^1H$ NMR (a mixture of diastereomers, $CDCl_3$): δ 8.08, 8.02, 8.01, 7.89 (4s, 2H), 7.39-7.13 (m, 25H), 6.83 (d, J=8.8 Hz, 2H), 6.79 (d, J=8.8 Hz, 2H), 4.98-4.89 (m, 1H), 4.78-4.63 (m, 2H), 4.19-3.15 (m, 5H), 3.79, 3.78 (2s, 6H), 2.29-1.70 (m, 2H), 1.35-1.22 (m, 12H), 1.20, 1.14 (2d, J=6.2 Hz each, 3H). HRMS Calcd for $C_{57}H_{62}N_5O_7P$ $(M+H)^+$ 960.4465. Found: 960.4417.

EXAMPLE 61

(±)-9-[1-[(Phosphonomethoxy)methyl][(3-monomethoxytriyloxy)propyl]-$N^6$-monomethoxytritladenine (54a). A solution of 35 (17.7 g, 18.71 mmol) in DMF (170 mL) is treated with triethylamine (15 mL) followed by trimethylsilyliodide (25 mL, 174.9 mmol) and the reaction mixture flask is covered with aluminum foil to protect from light and stirred for 16 h at room temperature. It was then diluted with TEAB buffer (0.5 L), water (0.75 L) and chloroform (1.5 L) and stirred for 1 h. The organic phase was collected and the aqueous phase was re-extracted with chloroform (3×). The combined organic extracts were dried over $MgSO_4$. After filtration, the filtrate was concentrated and the residue was purified on a silica gel column using chloroform:methanol (1:0 to 85:15), then CMA-80:CMA-50 (1:0 to 0:1) as eluent to give 7.5 g (47%) of 54a as a yellow solid: $^1H$ NMR (DMSO-$d_6$): δ 8.29 (s, 1H), 7.86 (s, 1H), 7.34-7.01 (m, 25H), 6.85 (d, J=9.1 Hz, 2H), 6.78 (d, J=8.9 Hz, 2H), 4.97-4.86 (m, 1H), 3.94-3.85 (m, 1H), 3.80-3.72 (m, 1H), 3.72 (s, 3H), 3.68 (s, 3H), 3.37 (d, J=7.6 Hz, 2H), 2.89-2.72 (m, 2H), 2.42-2.26 (m, 1H), 2.23-2.07 (m, 1H). HRMS Calcd for $C_{50}H_{48}N_5O_7P$ $(M+H)^+$ 862.3369. Found: 862.3387.

EXAMPLE 62

(±)-9-[1-[(Phosphonomethoxy)methyl][(3-monomethoxytritlyamino)propyl]-$N^6$-monomethoxytritladenine (54c).). It is prepared from 40 with the same procedure as given for 54a. The crude product is purified on a silica gel column using chloroform:methanol (1:0 to 85:15), then CMA-80: CMA-50 (1:0 to 0:1) as eluent to give 45% yield of 54c as a white solid: $^1H$ NMR (DMSO-$d_6$): δ 8.26 (s, 1H), 7.83 (s, 1H), 7.32-6.99 (m, 25H), 6.82 (d, J=9.1 Hz, 2H), 6.70 (d, J=9.1 Hz, 2H), 5.00-4.83 (m, 1H), 3.92-3.79 (m, 1H), 3.76-3.66 (m, 1H), 3.68 (s, 3H), 3.63 (s, 3H), 3.37 (d, J=7.5 Hz, 2H), 2.28-2.14 (m, 1H), 2.06-1.90 (m, 1H), 1.84-1.62 (m, 2H). HRMS Calcd for $C_{50}H_{49}N_6O_6P$ $(M+H)^+$ 861.3529. Found: 861.3562.

EXAMPLE 63

(±)-9-[1-[(Phosphonomethoxy)methyl][(3-methoxy)propyl]-$N^6$-monomethoxytritladenine (54d). A solution of 36 (1.0 g, 1.48 mmol) in DMF (12 mL) is treated with sodium hydride (60%, 0.24 g, 6.0 mmol) at room temperature and the mixture is stirred for 1 h. To this solution is then added a solution of methyliodide (0.11 mL, 1.77 mmol) in DMF (2 mL) and the mixture stirred at room temperature for 12 h. The reaction mixture is diluted with ethyl acetate (30 mL), neutralized with acetic acid and chloroform (400 mL) added. The mixture is washed with water (2×) and brine and the organic layer dried over $MgSO_4$ followed by filtration and concentration to give 41 which is converted to 54d following the same procedure as used for 54a. The product is purified on a silica gel column using chloroform:methanol (1:0 to 85:15), then CMA-80:CMA-50 (1:0 to 0:1), as eluent to give 296 mg (33%, two steps) of 54d as an off-white film: $^1$H NMR (DMSO-d$_6$): δ 8.34(s, 1H), 7.89 (s, 1H), 7.36-7.16 (m, 13H), 6.84 (d, J=9.1 Hz, 2H), 4.80-4.67 (m, 1H), 4.02-3.90 (m, 1H), 3.87-3.77 (m, 1H), 3.71 (s, 3H), 3.36-3.26 (m, 2H), 3.27-3.18 (m, 1H), 3.14-3.03 (m, 1H), 3.10 (s, 3H), 2.24-2.04 (m, 2H). HRMS Calcd for C$_{31}$H$_{34}$N$_5$O$_6$P (M+H)$^+$ 604.2325. Found: 604.2335.

EXAMPLE 64

(±)-9-[1-[(Phosphonomethoxy)methyl]propyl]-N$^6$-monomethoxytrityladenine (54e). Compound 45 is converted to 46 in 30% yield with the same procedure as used for 35 and 46 is converted to 54e with the same method used for 54a. The crude product is purified on a silica gel column using chloroform:methanol (1:0 to 85:15), then CMA-80:CMA-50 (1:0 to 0:1) as eluent to give 47% of 54e as a yellow solid: $^1$H NMR (DMSO-d$_6$): δ 8.36 (s, 1 H), 7.87 (s, 1 H), 7.4-6.8 (m, 14 H), 6.50 (bs, 2 H), 4.56 (m, 1 H), 3.95 (m, 1 H), 3.82 (m, 1 H), 3.69 (s, 3 H), 3.32 (m, 2 H), 1.86 (m, 2 H), 0.67 (t, J=7.1 Hz, 3 H). IR (KBr, cm$^{-1}$) 3408, 3159, 1604, 1469, 1401 and 1249.

EXAMPLE 65

(±)-9-[1-[(Di-tert-butylcarbonyloxymethylphosphonomethoxy)methyl][(3-monomethoxytrityloxy)propyl]-N$^6$-monomethoxytrityladenine (55a). A solution of 54a (400 mg, 0.46 mmol) in DMF (24 mL) is treated with triethylamine (24 mL) followed by tert-butylcarbonyloxymethyl chloride (8.9 mL, 97%, 59.9 mmol) and stirred for 3 days at room temperature. It is then diluted with chloroform (250 mL) and washed with water (2×). The organic layer is dried over MgSO$_4$. After filtration, the filtrate is concentrated and the residue purified on a silica gel column using ethyl acetate:hexanes:methanol (1:1:0 to 1:1:0.1) as eluent to give 83 mg (17%) of 55a as a colorless film: $^1$H NMR (DMSO-d$_6$): δ 8.41 (s, 1H), 8.10 (s, 1H), 7.57-7.25 (m, 25H), 7.08 (d, J=8.8 Hz, 2H), 7.01 (d, J=8.9 Hz, 2H), 5.78 (s, 2H), 5.74 (s, 2H), 5.24-5.12 (m, 1H), 4.22-4.10 (m, 3H), 4.10-4.00 (m, 1H), 3.95 (s, 3H), 3.92 (s, 3H), 3.15-3.05 (m, 1H), 3.05-2.92 (m, 1H), 2.68-2.50 (m, 1H), 2.43-2.28 (m 1H), 2.23 (s, 18H). IR (KBr, cm$^{-1}$) 3420, 2972, 1753, 1605, 1511, 1471 and 1251. Anal. Calcd for C$_{62}$H$_{68}$N$_5$O$_{11}$P.0.75 H$_2$O.0.25 EtOAc: C, 67.22; H, 6.40; N, 6.22. Found: C, 67.09; H, 6.37; N. 6.01.

EXAMPLE 66

(±)-9-[1-[(Di-isopropyloxycarbonyloxymethylphosphonomethoxy)methyl][(3-monomethoxytritylamino)propyl]-N$^6$-monomethoxytrityladenine (55c). It is prepared from 54c with the same procedure as given for 54a but using isopropyloxycarbonyloxymethyl chloride in place of tert-butylcarbonyloxymethyl chloride. The time of the reaction also increased to 7 days. The crude product is purified on a silica gel column using ethyl acetate:hexanes:methanol (1:1:0 to 1:1:0.1) as eluent to give 27% yield of product as a colorless oil: $^1$H NMR (CDCl$_3$): δ 7.98 (s, 1H), 7.87 (s, 1H), 7.38-7.07 (m, 25H), 6.80 (d, J=8.8 Hz, 2H), 6.72 (d, J=8.9 Hz, 2H), 5.68-5.56 (m, 4H), 5.08-4.95 (m, 1H), 4.95-4.84 (m, 2H), 4.05-3.80 (m, 2H), 3.86 (d, J=7.4 Hz, 2H), 3.77 (s, 3H), 3.73 (s, 3H), 2.37-2.20 (m, 1H), 2.12-1.78 (m, 4H), 1.28 (d, J=6.2 Hz, 6H), 1.27 (d, J=6.2 Hz, 6H). HRMS Calcd for C$_{60}$H$_{65}$N$_6$O$_{12}$P (M+H)$^+$ 1093.4476. Found: 1093.4483.

EXAMPLE 67

(±)-9-[1-[(Di-isopropyloxycarbonyloxymethylphosphonomethoxy)methyl][(3-methoxy)propyl]-N$^6$-monomethoxytrityladenine (55d). It is prepared from 54d with the same procedure as given for 55c. The crude product is purified on a silica gel column using ethyl acetate:hexanes:methanol (1:1:0 to 1:1:0.1) as eluent to give 35% yield of product as a colorless oil: $^1$H NMR (CDCl$_3$): δ 8.03 (s, 1H), 7.87 (s, 1H), 7.38-7.19 (m, 13H), 6.80 (d, J=9.0 Hz, 2H), 5.68-5.58 (m, 4H), 4.96-4.81 (m, 3H), 4.20-4.12 (m, 1H), 3.95-3.82 (m,3H), 3.78 (s, 3H), 3.41-3.32 (m, 1H), 3.24 (s, 3H), 3.18-3.08 (m, 1H), 2.38-2.15 (m, 2H), 1.31 (d, J=6.2 Hz, 12H). IR (neat, cm$^{-1}$) 3020, 1605 and 1216. Anal. Calcd for C$_{41}$H$_{50}$N$_5$O$_{12}$P: C, 58.92; H, 6.03; N, 8.38. Found: C, 58.89; H, 6.17; N. 8.23.

EXAMPLE 68

(±)-9-[1-[(Di-tert-butylcarbonyloxymethylphosphonomethoxy)methyl][(3-monomethoxytrityloxy)butyl]-N$^6$-monomethoxytrityladenine (55f). Compound 53 is converted to 54f with the same method used for 54a and 54f is converted to 55f with the method used for 55a. The product 55f is obtained in 17% yield (two steps) as a colorless oil: $^1$H NMR (a mixture of diastereomers, CDCl$_3$): δ 8.00, 7.93, 7.62 (3s, 2H), 7.46-7.10 (m, 25H), 6.90-6.68 (m, 4H), 5.64-5.52 (m, 4H), 4.94-4.64 (m, 1H), 3.95-3.85, 3.79-3.44, 3.35-3.25 (3m, 5H), 3.77 (m, 3H), 3.73 (s, 3H), 2.20-1.81, 1.76-1.56 (2m, 2H), 1.20, 1.19, 1.18 (3s, 18H), 0.92, 0.86 (2d, J=6.2 Hz each, 3H). HRMS Calcd for C$_{63}$H$_{70}$N$_5$O$_{11}$P (M+H)$^+$ 1104.4887. Found: 1104.4882.

EXAMPLE 69

(±)-9-[1-[(Di-tert-butylcarbonyloxymethylphosphonomethoxy)methyl][(3-hydroxy)propyl]adenine (56a). A solution of 55a (138 mg, 0.13 mmol) in acetonitrile (28 mL) is treated with 0.2 M HCl (1.4 mL) and stirred for 14 h at room temperature. It is then carefully neutralized with 0.5 N NaOH to pH 6.0 and diluted with water (15 mL) and concentrated to remove acetonitrile. The residual material is again diluted with water (20 mL) and extracted with chloroform:methanol (4:1, 2×). The organic layer is dried over MgSO$_4$. After filtration, the filtrate is concentrated and the residue is purified on a silica gel column using chloroform:methanol (1:0 to 9:1) as eluent to give 42 mg (59%) of 56a as a colorless oil.

Procedure for the fumarate salt of 56a: A solution of 56a (14.1 mg, 0.026 mmol) in 2-propanol (1.2 mL) is treated with a solution of fumaric acid in propanol (20.3 mg/mL, 0.45 mL, 0.026 mmol) followed by slow concentration under vacuum. The fumaric salt is obtained as a white solid: $^1$H NMR (DMSO-d$_6$): δ 12.95 (bs, 2H), 7.89 (s, 1H), 7.87 (s, 1H), 6.97 (s, 2H), 6.40 (s, 2H), 5.31 (d, J=3.4 Hz, 2H), 5.27 (d, J=3.5 Hz, 2H), 4.64-4.48 (bs, 1H), 4.44-4.24 (bs, 1H), 3.85 (t, J=9.1 Hz, 1H), 3.73-3.60 (m, 3H), 3.16-2.91 (m, 2H), 1.97-1.84 (m, 1H), 1.84-1.68 (m, 1H), 0.90 (s, 18H). HRMS Calcd for C$_{22}$H$_{36}$N$_5$O$_9$P (M+H)$^+$ 546.2329. Found: 546.2325.

EXAMPLE 70

(±)-9-[1-[(Di-tert-butylcarbonyloxymethylphosphonomethoxy)methyl][(3-azido)propyl]adenine (56b). Compound 38 is converted to 54b in 44% yield with the same method as used for 54a and 54b is converted to 55b in 64% yield by the method used for 55a. The resultant 55b is deprotected by the same method used for 56a to give 56b. The compound 56b is obtained in 82% yield as a colorless oil: $^1$H NMR (DMSO-d$_6$): 8.16 (s, 1H), 8.10 (s, 1H), 7.22 (bs, 2H), 5.52 (dd, J=12.6, 3.5 Hz, 4H) 4.77 (m, 1H), 4.03 (m, 1H), 3.92 (m, 3H), 3.29 (m, 1H), 3.16 (m, 1H), 2.27 (m, 1H), 2.09 (m, 1H), 1.13 (m, 18H). MS (ES$^+$) 571.24 (M+H)$^+$. Anal. Calcd for C$_{22}$H$_{35}$N$_8$O$_8$P: C, 46.31; H, 6.18; N, 19.6. Found: C, 46.67; H, 6.22; N, 18.56.

EXAMPLE 71

(±)-9-[1-[(Di-isopropyloxycarbonyloxymethylphosphonomethoxy)methyl][(3-amino)propyl]adenine (56c). A solution of 55c (45 mg, 0.041 mmol) in acetonitrile (6.6 mL) is treated with 0.2 M HCl (0.99 mL) and stirred for 16 h at room temperature. It is diluted with water (100 mL) and extracted with ethyl acetate (2×) and chloroform (2×). The aqueous layer is concentrated to dryness to give 56c as a gum. The product is dissolved in 2.0 mL of water and its concentration was measured to be 11.9 mM (58%) by UV at 259 nm: $^1$H NMR (D$_2$O): δ 8.32 (s, 1H), 8.29 (s, 1H), 5.47-5.36 (m, 4H), 4.90-4.72 (m, 3H), 4.05-3.86 (m, 4H), 3.04-2.90 (m, 1H), 2.84-2.70 (m, 1H), 2.49-2.35 (m, 1H), 2.35-2.20 (m, 1H), 1.17 (d, J=6.5 Hz, 6H), 1.16 (d, J=6.3 Hz, 6H). HRMS Calcd for C$_{20}$H$_{33}$N$_6$O$_{10}$P (M+H)$^+$ 549.2074. Found: 549.2070.

EXAMPLE 72

(±)-9-[1-[(Di-isopropyloxycarbonyloxymethylphosphonomethoxy)methyl][(3-methoxy)propyl]adenine (56d). It is prepared from 55d with the same procedure as given for 56a. The crude product is purified on a silica gel column using chloroform:methanol (1:0 to 9:1) as eluent to give 83% yield of product as a colorless oil: $^1$H NMR (CDCl$_3$): δ 8.32 (s, 1H), 7.94 (s, 1H), 5.73 (s, 2H), 5.68-5.60 (m, 4H), 4.96-4.84 (m, 3H), 4.18 (dd, J=10.0, 6.6 Hz, 1H), 3.92 (dd, J=9.9, 3.8 Hz, 1H), 3.86 (dd, J=7.6, 1.1 Hz, 2H), 3.42-3.32 (m, 1H), 3.23 (s, 3H), 3.15-3.02 (m, 1H), 2.41-2.16 (m, 2H), 1.32 (d, J=6.2 Hz, 6H), 1.31 (d, J=6.3 Hz, 6H). IR (neat, cm$^{-1}$) 3328, 2928, 1761, 1646, 1598 and 1267. HRMS Calcd for C$_{21}$H$_{34}$N$_5$O$_{11}$P (M+H)$^+$ 564.2070. Found: 564.2071.

EXAMPLE 73

(±)-9-[1-[(Di-tert-butylcarbonyloxymethylphosphonomethoxy)methyl]propyl]adenine (56e). Compound 54e is converted to 55e in 78% yield with the method used for 55a and the resultant 55e is converted to 56e with the same method as used for 56a. Compound 56e is obtained in 32% yield as a colorless oil: $^1$H NMR (DMSO-d$_6$): δ 8.4 (s, 1H), 8.35 (s, 1H), 7.45 (bs, 2H), 5.80 (m, 2H), 5.74 (m, 2H), 5.83 (m, 1H), 4.30 (m, 1H), 4.15 (m, 2H), 4.10 (m, 1H), 2.20 (m, 2H), 1.32 (s, 18H), 0.95 (t, J=7.1 Hz, 3H). MS (ES$^+$) 552.29 (M+Na)$^+$. Anal. Calcd for C$_{22}$H$_{36}$N$_5$O$_8$P: C, 49.90; H, 6.85; N, 13.22. Found: C, 49.97; H, 6.73; N, 13.21.

EXAMPLE 74

(±)-9-[1-[(Di-tert-butylcarbonyloxymethylphosphonomethoxy)methyl][(3-hydroxy)butyl]adenine (56f). It is prepared from 55f with the same procedure as given for 56a. The crude product is purified on a silica gel column using chloroform:methanol (1:0 to 9:1) as eluent to give 89% yield of product as a colorless oil: $^1$H NMR (a mixture of diastereomers, CDCl$_3$): δ 8.31, 8.12, 7.97 (3s, 2H), 6.11, 6.01 (2s, 2H), 5.74-5.58 (m, 4H), 5.04-4.91 (m, 1H), 4.25-3.78, 3.34-3.24 (2m, 4H), 3.92, 3.85 (2d, J=7.2 Hz each, 2H), 2.28-2.01, 1.86-1.74 (2m, 2H), 1.24, 1.15 (2d, J=6.2 Hz each, 3H), 1.21 (s, 18H). IR (neat, cm$^{-1}$) 3020, 1754, 1632, 1216 and 764. HRMS Calcd for C$_{23}$H$_{38}$N$_5$O$_9$P (M+H)$^+$ 560.2485. Found: 560.2469.

EXAMPLE 75

3,5-Isopropylidenepentan-1,3,5-triol (57). It is prepared according to literature procedure (Mori et al., Tetrahedron 1987, 43, 45-58).

EXAMPLE 76

(±)-1-Pivaloyl-3,5-isopropylidenepentan-1,3,5-triol (58). To a solution of 3,5-isopropylidenepentan-1,3,5-triol 57 (6.2 g, 38.69 mmol) in pyridine (125 mL) is added pivaloyl chloride (5.7 mL, 46.43 mmol) and the resulting reaction mixture is stirred at room temperature for 17 h. After evaporation of most of the solvent, water (200 mL) is added and then extracted with EtOAc (2×100 mL). The combined organic extracts are washed with water, dried over MgSO$_4$, filtered and concentrated to dryness to give 9.35 g of 58 (98%) as an oil: $^1$HNMR (CDCl$_3$): 4.13-4.17 (m, 2 H), 3.92-4.04 (m, 2 H), 3.80-3.89 (m, 1 H), 1.74-1.81 (m, 2 H), 1.54-1.72 (m, 2 H), 1.43 (s, 3 H), 1.37 (s, 3 H) and 1.19 (s, 9 H). IR (CHCl$_3$, cm$^{-1}$): 2959, 2918, 2872, 1726, 1458 and 1369.

EXAMPLE 77

(±)-5-Pivaloylpentan-1,3,5-triol (59). A mixture of 58 (10 g, 40.92 mmol) and 80% aqueous acetic acid (125 mL) is heated at 50-55° C. for 15 h. The reaction mixture is evaporated to dryness under vacuum and then co-evaporated-with toluene (3×35 mL) to give 8.0 g (96%) of 59 as an oil: $^1$HNMR (DMSO-d$_6$): 4.48 (d, J=5.65 Hz, 1 H), 4.34 (t, J=5.08 Hz, 1 H), 4.0-4.12 (m, 2 H), 3.60-3.71 (m, 1 H), 3.45-3.51 (m, 2 H), 1.43-1.72 (m, 4 H) and 1.12 (s, 9 H). IR (KBr, cm$^{-1}$): 3405, 2963, 1722, 1477, 1288, 1166 and 1057.

EXAMPLE 78

(±)-1-tert-Butyldiphenylsilyl-5-pivaloylpentan-1,3,5-triol (60). To a solution of 59 (8.0 g, 39.16) and imidazole (3.0 g, 43.07 mmol) in CH$_2$Cl$_2$ (170 mL) is added TBDPS-chloride (11.20 mL, 39.16 mmol) over a period of 1 h at room temperature. After stirring for 1 more h, the solvent is removed and the residue is purified on a silica gel column using ethyl acetate:hexanes as eluent to provide 13 g (75%) of 60, as a colorless oil: $^1$HNMR (DMSO-d$_6$): 7.57-7.67 (m, 4 H), 7.36-7.47 (m, 6 H), 4.55 (d, J=5.8 Hz, 1 H), 4.06-4.11 (m, 2 H), 3.66-3.85 (m, 3 H), 1.53-1.73 (m, 4 H), 1.11 (s, 9 H) and 0.97 (s, 9 H). IR (KBr, cm$^{-1}$): 3514, 2959, 2858, 1726, 1473 and 1428. HRMS Calcd for C$_{26}$H$_{38}$O$_4$Si (M+H)$^+$ 443.2617. Found 443.2598.

EXAMPLE 79

(±)-9-[(1-tert-Butyldiphenylsilyloxyethyl)(3-pivaloyloxy)propyl]adenine (61). To a stirring mixture of 60 (10.0 g, 22.59 mmol), triphenylphosphine (11.85 g, 45.18 mmol) and adenine (6.1 g, 45.18 mmol) in anhydrous dioxane (250 mL) is added a solution of DEAD (7.15 mL, 45.18 mmol) in dioxane (50 mL) over a period of 3 h at room temperature.

The reaction mixture is further stirred for 19 h, then filtered through a short pad of Celite and the filtrate concentrated. The residue is purified on a silica gel column using chloroform:methanol (100:0 to 99:2) as eluent to give the desired product 61, but it is contaminated with tri-phenylphosphine oxide and the DEAD derivative. Two more purifications on silica gel give 8.8 g of pure 61 (70%), as a white solid, mp 137-139° C.: $^1$HNMR (DMSO-d$_6$): 8.13 (s, 1 H), 8.09 (s, 1 H), 7.22-7.66 (m, 10 H), 7.21 (br, 2 H, exchangeable with D$_2$O), 4.92 (m, 1 H), 3.64-3.98 (m, 2 H), 3.24-3.58 (m, 2 H), 2.06-2.46 (m, 4 H), 1.05 (s, 9 H), 0.9 (s, 9 H). IR (KBr, cm$^{-1}$): 3313, 3153, 2962, 1711, 1667, 1601 and 1472. MS (ES$^+$) 560.31 (M+H). Anal. Calcd for C$_{31}$H$_{41}$N$_5$O$_3$Si: C, 66.51; H, 7.38; N, 12.51. Found: C, 66.26; H, 7.37; N, 12.70.

EXAMPLE 80

(±)-9-[(1-tert-Butyldiphenylsilyloxyethyl)(3-hydroxy)propyl]adenine (62). To a solution of 61 (7.6 g, 13.57 mmol) in anhydrous MeOH (300 mL) is added NaOMe (5.4 M solution in MeOH, 5.0 mL, 27.15 mmol), and then the reaction mixture is stirred at room temperature for 17 h. The mixture is neutralized to pH 7.0 with acetic acid and concentrated. The residue is purified on a silica gel column eluting with chloroform:methanol (100:0 to 95:5) to provide 4.2 g (65%) of 62 as a white solid, mp 144-147° C.: $^1$HNMR (DMSO-d$_6$): 8.09 (s, 1 H), 8.07 (s, 1 H), 7.24-7.56 (m, 10 H), 7.19 (br, 2 H, exchangeable with D$_2$O), 4.85 (m, 1 H), 4.55 (t, J=4.7 Hz, 1 H exchangeable with D$_2$O), 3.42-3.56 (m, 1 H), 3.1-3.42 (m, 3 H), 2.30-2.46 (m, 1 H), 1.92-2.44 (m, 3H), 0.89 (s, 9 H). IR (KBr, cm$^{-1}$): 3341, 3185, 2929, 2854, 1668, 1607, 1412 and 1317. MS (ES+) 476.33 (M+H). Anal. Calcd for C$_{26}$H$_{33}$N$_5$O$_2$Si.0.5 H$_2$O: C, 64.43; H, 7.07; N, 14.44. Found: C, 64.52; H, 7.14; N, 14.16.

EXAMPLE 81

(±)-9-[(1-tert-Butyldiphenylsilyloxyethyl)(3-trityloxy)propyl]-N$^6$-trityladenine (63). To a solution of 62 (1.9 g, 3.99 mmol) and DMAP (180 mg) in anhydrous pyridine (100 mL) is added tritylchloride (4.4 g, 15.97 mmol), and then the reaction mixture is heated at 65° C. for 16 h. More tritylchloride (4.4 g) is added and heated another 8 h at 65° C. Another 4.4 g of trityl chloride and triethyl amine (1.0 mL) is added and heated for 17 h. The solvent is removed and the residue is purified on a silica gel column eluting with hexanes:ethanol (100:0 to 70:30) to provide 2.1 g (54%) of 63 as a white solid, mp 202-204° C.: $^1$HNMR (CDCl$_3$): 7.90 (s, 1 H), 7.14-7.62 (m, 41 H), 6.88 (s, 1 H), 4.95-5.12 (m, 1 H), 3.55-3.66 (m, 1 H), 3.26-3.37 (m, 1 H), 3.04-3.14 (m, 1 H), 2.63-2.74 (m, 1 H), 2.29-2.51 (m, 2 H), 2.0-2.24 (m, 2 H) and 1.63 (s, 9 H). IR (KBr, cm$^{-1}$): 3417, 3055, 2855, 1602, 1469 and 1442. MS (ES+) 960.27 (M+H). Anal. Calcd for C$_{64}$H$_{61}$N$_5$O$_2$Si.0.5 H$_2$O: C, 79.30; H, 6.44; N, 7.23. Found: C, 79.33; H, 6.39; N, 7.25.

EXAMPLE 82

(±)-9-[(1-Trityloxyethyl)(3-hydroxy)propyl]-N$^6$-trityladenine (64). To a solution of 63 (2 g, 2.08 mmol) in THF (80 mL) is added 1M solution of TBAF in THF (2.2 mL, 2.2 mmol) and then the reaction mixture is stirred at room temperature for 2 h. The reaction mixture is concentrated and the residue is purified on a silica gel column eluting with chloroform:methanol (100:0 to 98:2) to provide 1.2 g (80%) of 64 as a white solid, mp 160-170° C.: $^1$HNMR (DMSO-d$_6$): 8.18 (s, 1 H), 7.83 (s, 1 H), 7.1-7.4 (m, 31 H), 4.84 (m, 1 H), 4.54 (t, J=5.0 Hz, 1H) 3.1-3.4 (m, 2 H), 2.62-2.88 (m, 2 H), 1.88-2.44 (m, 4 H). IR (KBr, cm$^{-1}$): 3054, 2926, 1605, 1470, 1444 and 1216. HRMS Calcd for C$_{48}$H$_{43}$N$_5$O$_2$ (M+H)$^+$ 722.3495. Found 722.3528. Anal. Calcd for C$_{48}$H$_{43}$N$_5$O$_2$.0.2 CHCl$_3$: C, 77.62; H, 5.83; N, 9.39. Found: C, 77.32; H, 5.82; N, 9.34.

EXAMPLE 83

(±)-9-[(1-Trityloxyethyl)(3-diisopropylphosphonomethoxy)propyl]-N$^6$-trityladenine (65) and (±)-9-[(1-Trityloxyethyl)(3-mono-isopropylphosphonomethoxy)propyl]-N$^6$-trityladenine (66). To a solution of 64 (0.54 g, 0.748 mmol) in DMF (6 mL) is added NaH (120 mg, 60% dispersion in oil, 2.99 mmol) under N$_2$ atmosphere. After stirring the mixture for 0.5 h at room temperature, a solution of p-toluenesulfonyloxymethyl phosphonate in DMF (1.0 mL) is added over a period of 5 min. The reaction mixture is stirred at room temperature for 18 h and then neutralized slowly with acetic acid at 0-5° C. After removing most of the solvent, the mixture is extracted with chloroform (60 mL), the organic layer washed with water (2×30 mL), dried over MgSO$_4$, filtered and concentrated. The residue is purified on a silica gel column using ethyl acetate: hexanes:methanol (100:0:0 to 70:25:5) as eluent to provide 0.204 g (30%) of 65 as a gum: $^1$HNMR (DMSO-d$_6$): 8.18 (s, 1 H), 7.8 (s, 1 H), 7.13-7.33 (m, 31 H), 4.84 (m, 1 H), 4.46-4.59 (m, 2 H), 3.62(d, J=7.9 Hz, 2 H), 3.20-3.46 (m, 4 H), 1.98-2.8 (nm 4 H), 1.14-1.20 (m, 12 H). IR (KBr, cm$^{-1}$): 3417, 3057, 2976, 1605, 1471 and 1220. HRMS Calcd for C$_{55}$H$_{58}$N$_5$O$_5$P (M+H)$^+$ 900.4254. Found 900.4269. Anal. Calcd for C$_{55}$H$_{58}$N$_5$O$_2$P.0.5 H$_2$O: C, 72.66; H, 6.54; N, 7.70. Found: C, 72.55; H, 6.37; N, 7.72.

Further elution of the column with CMA-80 afforded 0.200 g (31%) of 66 as a light yellow gum: MS (ES−) 856.04 (M−H).

EXAMPLE 84

(±)-9-[(1-Trityloxyethyl)(3-phosphonomethoxy)propyl]-N$^6$-trityladenine (67). To a solution of 65 (0.13 g, 0.144 mmol) and 66 (0.2 g, 0.233 mmol) in DMF (6.0 mL) are added Et$_3$N (0.4 mL) and TMSI (1.07 mL, 7.54 mmol) and stirred at room temperature for 13 h (in the dark). To this reaction mixture is added TEAB (35 mL), water (60 mL) and chloroform (100 mL) and stirred at room temperature for 1.5 h. The chloroform layer is separated and the water layer is re-extracted with chloroform (3×30 mL). Combined chloroform extracts are dried over MgSO$_4$, filtered and the filtrate concentrated. The residue is purified on a silica gel column eluting with chloroform:methanol:NH$_4$OH (100:0:0 to 50:40:10) to provide 0.15 g (48%) of 67: $^1$HNMR (DMSO-d$_6$): 8.22 (s, 1 H), 7.8 (s, 1 H), 7.06-7.35 (m, 31 H), 4.74-4.84 (m, 1 H), 3.0-3.6 (m, 6 H), 2.56-2.84 (m, 2 H), 1.95-2.2 (m, 2 H). IR (KBr, cm$^{-1}$): 3415, 3028, 2876, 1605, 1472, 1446 and 1219. HRMS Calcd for C$_{49}$H$_{46}$N$_5$O$_5$P (M+H)$^+$ 816.3315. Found 816.3331.

EXAMPLE 85

(±)-9-[(1-Trityloxyethyl)(3-di-tert-butylcarbonyloxymethylphosphonomethoxy)propyl]-N$^6$-trityladenine (68). To a solution of 67 (0.14 g, 0.17 mmol) in DMF (6 mL) are added Et$_3$N (6.2 mL, 42.89 mmol) and chloromethyl pivalate (3.1 mL, 21.45 mmol) under N$_2$ atmosphere and the reaction mixture stirred at room temperature for 4 days. The mixture is diluted with water (40 mL) and then extracted with chloroform (3×30 mL). Combined chloroform extracts are dried over $MgSO_4$, filtered, and the filtrate concentrated. The residue is purified on a silica gel column using ethyl acetate:hexanes:methanol (90:10:0 to 50:49:1) to provide 0.093 g (52%) of 68 as a light yellow solid, mp 73-75° C.: $^1$HNMR (DMSO-$d_6$): 8.16 (s, 1 H), 7.82 (s, 1 H), 7.12-7.33 (m, 31 H), 5.60 (s, 2 H), 5.56 (s, 2 H), 4.72-4.87 (m, 1 H), 3.79 (d, J=7.9 Hz, 2 H), 3.15-3.48 (m, 4 H), 1.95-3.0 (m, 4 H) and 1.11 (bs, 18 H). IR (KBr, cm$^{-1}$): 3419, 3028, 2973, 1753, 1605, 1473, 1448 and 1280. HRMS Calcd for $C_{61}H_{66}N_5O_9P$ (M+H)$^+$ 1044.4676. Found 1044.4629. Anal. Calcd for $C_{61}H_{66}N_5O_9P.0.25$ EtOAc: C, 69.84; H, 6.42; N, 6.56. Found: C, 69.61; H, 6.32; N, 6.47.

EXAMPLE 86

(±)-9-[(1-Hydroxyethyl)(3-di-tert-butylcarbonyloxymethylphosphonomethoxy)propyl]adenine (69). A mixture of 68 (0.16 g, 0.15 mmol), HCl (2.0 N, 15 mL) and MeCN (15 mL) is stirred at room temperature for 15 h. The reaction mixture is neutralized with $Et_3N$, and then diluted with water (40 mL). After evaporating the organic volatiles, the residue is extracted with chloroform (3×70 mL), dried ($MgSO_4$), filtered and the filtrate evaporated to dryness. The residue is purified over a silica gel column eluting with chloroform:methanol (100:0 to 96:4). First, a compound (60 mg) (49%) with one trityl group still attached is obtained. Further elution of the column gave 24 mg (28%) of the desired 69 as a gum: $^1$HNMR (CDCl$_3$): 8.27 (s, 1 H), 7.89 (s, 1 H), 6.17 (brs, 2 H), 5.58-5.79 (m, 4 H), 4.92 (m, 1 H), 3.75 (d, J=7.9 Hz, 2 H), 3.52-3.64 (m, 2 H), 3.1-3.42 (m, 2 H), 2.11-2.56 (m, 4 H), 1.22 (s, 18 H). IR (KBr, cm$^{-1}$): 3341, 2974, 2876, 1752, 1646, 1611, 1479. MS (ES+) 582.43 (M+Na). Anal. Calcd for $C_{23}H_{38}N_5O_9P.0.75$ $H_2O$: C, 48.20; H, 6.94; N, 12.22. Found: C, 48.26; H, 7.04; N, 11.94.

EXAMPLE 87

(±)-9-[(1-tert-Butyldimethylsilyloxymethyl)(3-pivaloyloxy)propyl]-6-chloropurine (70). To a mixture of 2 (92 g, 0.302 mol), triphenylphosphine (158 g, 0.60 mol) and 6-chloropurine (95 g, 0.60 mol) in anhydrous dioxane (1.5 L) is added a solution of DIAD (0.6 mol) in dioxane (60 mL) over a period of 3.5 h at room temperature and the mixture stirred further for 16 h. The reaction mixture is filtered through a short pad of Celite to remove insoluble materials and the residue purified on a column of silica gel eluting with CHCl$_3$:MeOH (100:0 to 95:5) to provide 95 g (72%) of 2 as a gum. $^1$H NMR (CDCl$_3$): δ 8.87 (s, 1H), 8.27 (s, 1H), 4.85 (m, 1H), 4.18-4.02 (m, 2H), 3.95-3.82 (m, 2H), 2.42-2.28 (m, 2H), 1.15 (s, 9H), 0.82 (s, 9H)., 0.0 (m, 6 H). IR (KBr, cm$^{-1}$) 3019, 2400, 1724, 1592, 1215, 765. MS (ES+) 463.38 (M+Na)+. Anal. Calcd for $C_{20}H_{33}ClN_4O_3Si$: C, 55.04; H, 7.66; N, 12.46. Found: C, 54.72; H, 7.53; N, 12.19.

General Procedure for the Conversion of 70 to 71a-m.

To a solution of 70 in EtOH (15 mL/mmol) is added 10 eq. of $Et_3N$ and 6 eq. of the corresponding amine. The resulting solution is stirred at 60° C. for 16 h, evaporated to dryness and partitioned between chloroform and water. The organic layer is collected, washed 3 times with water, dried over $MgSO_4$ and evaporated to dryness to give an oil. The resulting oil is dissolved in THF (10 mL/mmol) and a solution of 1 M TBAF in THF added (1.1 eq.). The reaction is stirred at room temperature for 30 min, evaporated to dryness, then adsorbed on silica gel and chromatographed using chloroform:methanol as eluent to give the desilylated derivative.

To the latter are added pyridine (10 mL/mmol) and trityl chloride (2 eq.) and the reaction mixture stirred at 70° C. for 16 h. The reaction mixture is then evaporated to dryness, the residue is dissolved in ethyl acetate and washed with water 3 times. The organic layer on concentration and purification on a silica gel column using hexanes:ethyl acetate (100:0 to 90:10) as eluent gives tritylated product, which is dissolved in MeOH (10 mL/mmol) and treated with 5.4 N NaOMe in MeOH (2 eq.). The reaction mixture is stirred at room temperature for 16 h and neutralized with acetic acid. The resulting mixture is then evaporated to dryness, the residue is dissolved in CHCl$_3$ and washed with water. The organic layer is dried over $MgSO_4$, filtered and the filtrate is concentrated and the residue is purified on a silica gel column eluting with CHCl$_3$:MeOH (100:0 to 95:5) to provide the desired compounds 71a-m.

EXAMPLE 88

(±)-9-[(1-Trityloxymethyl)(3-hydroxy)propyl]-6-diethylaminopurine (71a). Using the general procedure, 70 gives 71a (80%). $^1$H NMR (DMSO-$d_6$): δ 8.30 (s, 1H), 8.12 (s, 1H), 7.30-7.00 (m, 15H), 4.85 (m, 1H), 4.56 (t, 1H, J=4.9 Hz), 3.99 (m, 4H), 3.39 (m, 1H), 3.30 (m, 1H partially masked by water peak in DMSO-$d_6$), 3.19 (m, 2H), 2.33 (m, 1H), 2.02 (m, 1H), 1.22 (t, 6H, J=6.7 Hz). IR (KBr, cm$^{-1}$) 2927, 1583, 1442, 1282, 1031. HRMS Calcd for $C_{32}H_{35}N_5O_2$ (M+H)$^+$ 522.2868. Found 522.2854.

EXAMPLE 89

(±)-9-[(1-Trityloxymethyl)(3-hydroxy)propyl]-6-(N-methyl-N-ethyl)aminopurine (71b). Using the general procedure, 70 gives 71b (73%). $^1$H NMR (DMSO-$d_6$): δ 8.30 (s, 1H), 8.13 (s, 1H), 7.30-7.00 (m, 15H), 4.87 (m, 1H), 4.56 (t, 1H, J=4.9 Hz), 4.10 (m, 2H), 3.49-3.25 (m, 5H), 3.20 (m, 2H), 2.32 (m, 1H), 2.01 (m, 1H), 1.19 (t, 3H, J=6.9 Hz). IR (KBr, cm$^{-1}$) 2870, 1586, 1284, 1025, 898. HRMS Calcd for $C_{31}H_{33}N_5O_2$ (M+H)$^+$ 508.2712. Found 508.2689.

EXAMPLE 90

(±)-9-[(1-Trityloxymethyl)(3-hydroxy)propyl]-6-ethylaminopurine (71c). Using the general procedure, 70 gives 71c (90%). $^1$H NMR (DMSO-$d_6$): δ 8.88 (br s, 1H), 8.26 (s, 1H), 8.11 (s, 1H), 7.30-7.00 (m, 15H), 4.84 (m, 1H), 4.55 (t, 1H, J=5.0 Hz), 3.53 (m, 2H), 3.40 (m, 1H), 3.29 (m, 1H, partially masked by water peak in DMSO-$d_6$), 3.19 (m, 2H), 2.32 (m, 1H), 1.99 (m, 1H), 1.22 (m, 3H). IR (KBr, cm$^{-1}$) 2978, 2878, 1710, 1615, 1446, 1221, 1105, 1043. HRMS Calcd for $C_{30}H_{31}N_5O_2$ (M+H)$^+$ 494.2555. Found 494.2552.

EXAMPLE 91

(±)-9-[(1-Trityloxymethyl)(3-hydroxy)propyl]-6-allylaminopurine (71d). Using the general procedure, 70 gives 71d (90%). $^1$H NMR (DMSO-$d_6$): δ 8.88 (br s, 1H), 8.29 (s, 1H), 8.12 (s, 1H), 7.30-7.00 (m, 15H), 5.99 (m, 1H), 5.18 (dd, 1H, J=1.6 and 15.4 Hz), 5.05 (dd, 1H, J=1.6 and 11.8 Hz), 4.85 (m, 1H), 4.56 (t, 1H, J=5.0 Hz), 4.13 (m, 2H), 3.40 (m, 1H), 3.29 (m, 1H, partially masked by water peak in DMSO-$d_6$), 3.19 (m, 2H), 2.32 (m, 1H), 2.00 (m, 1H). IR (KBr, cm$^{-1}$) 3284, 2980, 1710, 1615, 1448, 1221, 1105, 1041. HRMS Calcd for $C_{31}H_{31}N_5O_2$ (M+H)$^+$ 506.2555. Found 506.2547.

EXAMPLE 92

(±)-9-[(1-Trityloxymethyl)(3-hydroxy)propyl]-6-N-thiazolidinopurine (71e). Using the general procedure, 70 gives 71e (40%). $^1$H NMR (DMSO-$d_6$): δ 8.39 (s, 1H), 8.22 (s, 1H), 7.30-7.00 (m, 15H), 5.12 (m, 1H), 4.91 (m, 1H), 4.31 (m, 2H), 3.50-3.10 (m, 8H), 2.34 (m, 1H), 2.02 (m, 1H). IR (KBr, cm$^{-1}$) 2931, 2877, 1691, 1582, 1456, 1218, 1032. HRMS Calcd for $C_{31}H_{31}N_5O_2S$ (M+H)$^+$ 538.2276. Found 538.2262.

EXAMPLE 93

(±)-9-[(1-Trityloxymethyl)(3-hydroxy)propyl]-6-N-azetidinopurine (71f). Using the general procedure, 70 gives 71f (88%). $^1$H NMR (DMSO-$d_6$): δ 8.26 (s, 1H), 8.12 (s, 1H), 7.30-7.00 (m, 15H), 4.85 (m, 1H), 4.54 (t, 1H, J=4.9 Hz), 4.36 (m, 4H), 3.41 (m, 1H), 3.28 (m, 1H), 3.19 (m, 2H), 2.44 (m, 2H, partially masked by DMSO), 2.30 (m, 1H), 2.00 (m, 1H). IR (KBr, cm$^{-1}$) 2934, 1589, 1465, 1296, 1221, 1072, 1049, 896. HRMS Calcd for $C_{31}H_{31}N_5O_2$ (M+H)$^+$ 506.2555. Found 506.2531.

EXAMPLE 94

(±)-9-[(1-Trityloxymethyl)(3-hydroxy)propyl]-6-N-piperidinopurine (71g). Using the general procedure, 70 gives 71g (22%). $^1$H NMR (DMSO-$d_6$): δ 8.32 (s, 1H), 8.13 (s, 1H), 7.30-7.00 (m, 15H), 4.87 (m, 1H), 4.55 (t, 1H, J=5.0 Hz), 4.22 (m, 4H), 3.39 (m, 1H), 3.29 (m, 1H), 3.20 (m, 2H), 2.32 (m, 1H), 2.01 (m, 1H), 1.63 (m, 6H). IR (KBr, cm$^{-1}$) 2849, 1584, 1444, 1338, 1248, 1048, 982. HRMS Calcd for $C_{33}H_{35}N_5O_2$ (M+H)$^+$ 534.2868. Found 534.2842.

EXAMPLE 95

(±)-9-[(1-Trityloxymethyl)(3-hydroxy)propyl]-6-N-morpholinopurine (71h). Using the general procedure, 70 gives 71h (22%). $^1$H NMR (DMSO-$d_6$): δ 8.34 (s, 1H), 8.19 (s, 1H), 7.30-7.00 (m, 15H), 4.90 (m, 1H), 4.55 (t, 1H, J=4.9 Hz), 4.23 (m, 4H), 3.73 (m, 4H), 3.41 (m, 1H), 3.30 (m, 1H), 3.20 (m, 2H), 2.31 (m, 1H), 2.00 (m, 1H). IR (KBr, cm$^{-1}$) 2853, 1580, 1444, 1251, 1111, 1066, 995. HRMS Calcd for $C_{32}H_{33}N_5O_3$ (M+H)$^+$ 536.2661. Found 536.2639.

EXAMPLE 96

(±)-9-[(1-Trityloxymethyl)(3-hydroxy)propyl]-6-N-pyrrolidinopurine (71i). Using the general procedure, 70 gives 71i (20%). $^1$H NMR (DMSO-$d_6$): δ 8.32 (s, 1H), 8.14 (s, 1H), 7.30-7.00 (m, 15H), 4.86 (m, 1H), 4.55 (t, 1H, J=5.0 Hz), 4.09 (m, 2H), 3.66 (m, 2H), 3.43 (m, 1H), 3.28 (m, 1H), 3.18 (m, 2H), 2.30 (m, 1H), 1.95 (m, 5H). IR (KBr, cm$^{-1}$) 2925, 1588, 1467, 1323, 1220, 972. HRMS Calcd for $C_{32}H_{33}N_5O_2$ (M+H)$^+$ 520.2712. Found 520.2689.

EXAMPLE 97

(±)-9-[(1-Trityloxymethyl)(3-hydroxy)propyl]-6-N-phenylaminopurine (71j). Using the general procedure, 70 gives 71j (22%). $^1$H NMR (DMSO-$d_6$): δ 9.90 (s, 1H), 8.40 (s, 1H), 8.00 (s, 1H), 7.40-7.00 (m, 20H), 4.90 (m, 1H), 4.60 (t, 1H, J=4.8 Hz), 3.46 (m, 1H), 3.36 (m, 1H), 3.25 (m, 2H), 2.37 (m, 1H), 2.02 (m, 1H). IR (KBr, cm$^{-1}$) 2926, 1615, 1576, 1468, 1437, 1364, 1218, 1050, 898. HRMS Calcd for $C_{34}H_{31}N_5O_2$ (M+H)$^+$ 542.2555. Found 542.2543.

EXAMPLE 98

(±)-9-[(1-Trityloxymethyl)(3-hydroxy)propyl]-6-cyclopentylaminopurine (71k). Using the general procedure, 70 gives 71k (80%). $^1$H NMR (DMSO-$d_6$): δ 8.27 (s, 1H), 8.10 (s, 1H), 7.30-7.00 (m, 15H), 4.83 (m, 1H), 4.55 (t, 1H, J=4.9 Hz), 3.40 (m, 1H), 3.29 (m, 1H, partially masked by D$_2$O), 3.19 (m, 2H), 3.00 (m, 1H), 2.43 (m, 1H partially masked by DMSO), 2.32 (m, 1H), 2.00-41.97 (m, 2H), 1.63 (m, 6H). IR (KBr, cm$^{-1}$) 2938, 1710, 1614, 1476, 1222, 1105, 1039. HRMS Calcd for $C_{33}H_{35}N_5O_2$ (M+H)$^+$ 534.2868. Found 534.2851.

EXAMPLE 99

(±)-9-[(1-Trityloxymethyl)(3-hydroxy)propyl]-6-cyclopropylaminopurine (71l). Using the general procedure, 70 gives 71l (88%). $^1$H NMR (DMSO-$d_6$): δ 8.28 (s, 1H), 8.16 (s, 1H), 7.88 (br s, 1H), 7.30-7.00 (m, 15H), 4.86 (m, 1H), 4.56 (t, 1H, J=4.9 Hz), 3.41 (m, 1H), 3.30 (m, 1H, partially masked water peak in DMSO-$d_6$), 3.17 (m, 3H), 2.32 (m, 1H), 2.00 (m, 1H), 0.95 (m, 2H), 0.80 (m, 2H). IR (KBr, cm$^{-1}$) 1615, 1575, 1473, 1353, 1214, 1050. HRMS Calcd for $C_{31}H_{31}N_5O_2$ (M+H)$^+$ 506.2555. Found 506.2539.

EXAMPLE 100

(±)-9-[(1-Trityloxymethyl)(3-hydroxy)propyl]-6-cyclobutylaminopurine (71 m). Using the general procedure, 70 gives 71m (78%). $^1$H NMR (DMSO-$d_6$): δ 8.27 (s, 1H), 8.10 (s, 1H), 7.94 (m, 1H), 7.30-7.00 (m, 15H), 4.80 (m, 2H), 4.54 (t, 1H, J=5.0 Hz), 3.40 (m, 1H), 3.30 (m, 1H, partially masked by water peak in DMSO-$d_6$), 3.20 (m, 2H), 2.16 (m, 6H), 1.66 (m, 2H). IR (KBr pellets, cm$^{-1}$) 2929, 1612, 1575, 1471, 1219, 1048, 896. HRMS Calcd for $C_{32}H_{33}N_5O_2$ (M+H)$^+$ 520.2712. Found 520.2690.

General Procedure for the Conversion of 71a-m to 72a-m:

A solution of 71a-m in DMF (7.5 mL/mmol) is treated with sodium hydride (4 eq.) at room temperature and the mixture stirred for 1 h. To this solution is then added a solution of p-toluenesulfonyloxymethylphosphonate (1.2 eq.) in DMF (5 mL) and the mixture stirred at room temperature for 24 h. The reaction mixture is diluted with ethyl acetate, neutralized with acetic acid and washed with water and brine and the organic layer is dried over MgSO$_4$. After filtration, the filtrate is concentrated and the residue is purified on a silica gel column using ethyl acetate:hexanes:methanol (1:1:0 to 1:1:0.05) as an eluent to give the desired phosphonomethoxy derivatives.

The phosphonomethoxy derivative is taken in DMF (10 mL/mmol) and treated with triethylamine (1 mL/mmol) followed by trimethylsilyliodide (1.5 mL/mmol) and the reaction mixture flask covered with aluminum foil to protect from light and stirred for 14 h at room temperature. It is then diluted with 1 N tetraethylammonium bicarbonate buffer (10 mL/mmol), water (30 mL/mmol) and chloroform (40 mL/mmol) and is stirred for 1 h. The organic phase is collected and the aqueous phase is re-extracted with chloroform and the combined organic phases are dried over MgSO$_4$. After filtration, the filtrate is concentrated and the residue is purified on a silica gel column using chloroform:methanol (1:0 to 85:15), then CMA-80:CMA-50 (1:0 to 0:1), as eluent to give the free phosphonates 72a-m.

EXAMPLE 101

(±)-9-[(1-Trityloxymethyl)(3-phosphonomethoxy)propyl]-6-diethylaminopurine (72a). Using the general procedure, 71a gives 72a (6%). $^1$H NMR (DMSO-$d_6$): δ 8.29 (s, 1H), 8.08 (s, 1H), 7.30-7.00 (m, 15H), 4.80 (m, 1H), 3.95 (m, 4H), 3.50-3.10 (m, 6H), 2.33 (m, 1H), 2.04 (m, 1H), 1.22 (t, 6H, J=6.7 Hz). $^{31}$P NMR: 13.20. HRMS Calcd for $C_{33}H_{38}N_5O_5P$ (M+H)$^+$ 616.2688. Found 616.2690.

EXAMPLE 102

(±)-9-[(1-Trityloxymethyl)(3-phosphonomethoxy)propyl]-6-N-methyl-N-ethylaminopurine (72b). Using the general procedure, 71b gives 72b (6.5%). $^1$H NMR (DMSO-$d_6$): δ 8.30 (s, 1H), 8.11 (s, 1H), 7.30-7.00 (m, 15H), 6.10 (br s, 2H), 4.82 (m, 1H), 4.07 (m, 2H), 3.50-3.10 (m, 9H), 2.35 (m, 1H, partially masked by DMSO-$d_6$), 2.07 (m, 1H), 1.19 (t, 3H, J=6.8 Hz). $^{31}$P NMR: 13.20. HRMS Calcd for $C_{32}H_{36}N_5O_5P$ (M+H)$^+$ 602.2532. Found 602.2518.

EXAMPLE 103

(±)-9-[(1-Trityloxymethyl)(3-phosphonomethoxy)propyl]-6-ethylaminopurine (72c). Using the general procedure, 71c gives 72c (11%). $^1$H NMR (DMSO-$d_6$): δ 8.29 (s, 1H), 8.08 (s, 1H), 7.87 (br s, 1H), 7.3-7.00 (m, 15H), 5.99 (m, 1H), 5.16 (dd, 1H, J=1.7 and 17.1 Hz), 5.07 (dd, 1H, J=1.7 and 17.0 Hz), 4.80 (m, 1H), 4.17 (m, 2H), 3.77 (m, 2H), 3.50-3.00 (m, 6H), 2.35 (m, 1H), 2.04 (m, 1H). $^{31}$P NMR: 13.19. HRMS Calcd for $C_{32}H_{34}N_5O_5P$ (M+H)$^+$ 600.2375. Found 600.2370.

EXAMPLE 104

(±)-9-[(1-Trityloxymethyl)(3-phosphonomethoxy)propyl]-6-allylaminopurine (72d). Using the general procedure, 71d gives 72d (5.5%). $^1$H NMR (DMSO-d6): δ 8.26 (s, 1H), 8.10 (s, 1H), 7.30-7.00 (m, 15H), 4.83 (m, 1H), 4.60 (br s, 2H), 4.08 (m, 2H), 3.65 (m, 2H), 3.48 (m, 1H), 3.30-3.00 (m, 5H), 2.30 (m, 1H), 1.93 (m, 5H). $^{31}$P NMR: 13.38. HRMS Calcd for $C_{33}H_{36}N_5O_5P$ (M+H)$^+$ 614.2532. Found 614.2551.

EXAMPLE 105

((±)-9-[(1-Trityloxymethyl)(3-phosphonomethoxy)propyl]-6-N-thiazolidinopurine (72e). Using the general procedure, 71e gives 72e (6%). $^1$H NMR (DMSO-$d_6$): δ 8.39 (s, 1H), 8.18 (s, 1H), 7.30-7.00 (m, 15H), 5.12 (m, 2H), 4.88 (m, 1H), 4.60 (br s, 2H), 4.30 (m, 2H), 3.50 (m, 1H), 3.18 (m, 7H), 2.35 (m, 1H, partially masked by DMSO-$d_6$), 2.07 (m, 1H). $^{31}$P NMR: 13.03. HRMS Calcd for $C_{32}H_{34}N_5O_5SP$ (M+H)$^+$ 632.2096. Found 632.2094.

EXAMPLE 106

(±)-9-[(1-Trityloxymethyl)(3-phosphonomethoxy)propyl]-6-N-azetidinopurine (72f). Using the general procedure, 71f gives 72f (6.5%). $^1$H NMR (DMSO-$d_6$): δ 8.35 (s, 1H), 8.15 (s, 1H), 7.30-7.00 (m, 15H), 5.30 (br s, 2H), 4.86 (m, 1H), 4.23 (m, 4H), 3.72 (m, 4H), 3.48 (m, 1H), 3.40-3.10 (m, 5H), 2.35 (m, 1H), 2.05 (m, 1H). $^{31}$P NMR: 13.19. HRMS Calcd for $C_{33}H_{36}N_5O_6P$ (M+H)$^+$ 630.2481. Found 630.2507.

EXAMPLE 107

(±)-9-[(1-Trityloxymethyl)(3-phosphonomethoxy)propyl]-6-N-piperidinopurine (72g). Using the general procedure, 71g gives 72g (9%). $^1$H NMR (DMSO-$d_6$): δ 8.30 (s, 1H), 8.10 (s, 1H), 7.30-7.00 (m, 15H), 4.83 (m, 1H), 4.60 (br s, 2H), 4.21 (m, 4H), 3.46 (m, 1H), 3.40-3.00 (m, 5H), 2.35 (m, 1H), 2.06 (m, 1H), 1.64 (m, 6H). $^{31}$P NMR: 13.15 HRMS Calcd for $C_{34}H_{38}N_5O_5P$ (M+H)$^+$ 628.2688. Found 628.2685.

EXAMPLE 108

(±)-9-[(1-Trityloxymethyl)(3-phosphonomethoxy)propyl]-6-N-morpholinopurine (72h). Using the general procedure, 71h gives 72h (6%). $^1$H NMR (DMSO-$d_6$): δ 8.28 (s, 1H), 8.09 (s, 1H), 7.30-7.00 (m, 15H), 4.82 (m, 1H), 4.60 (br s, 2H), 4.37 (m, 2H), 3.48 (m, 1H), 3.28 (m, 1H), 3.14 (m, 4H), 2.46 (m, 2H, partially masked by DMSO-$d_6$), 2.30 (m, 1H), 2.04 (m, 1H). $^{31}$P NMR: 13.05. HRMS Calcd for $C_{32}H_{34}N_5O_5P$ (M+H)$^+$ 600.2375. Found 600.2369.

EXAMPLE 109

(±)-9-[(1-Trityloxymethyl)(3-phosphonomethoxy)propyl]-6-N-pyrrolidinopurine (72i). Using the general procedure, 71i gives 72i (10%). $^1$H NMR (DMSO-$d_6$): δ 8.27 (s, 1H), 8.15 (s, 1H), 7.3-7.00 (m, 15H), 4.83 (m, 1H), 4.51 (br s, 2H), 4.10 (m, 2H), 3.65 (m, 2H), 3.52 (m, 1H), 3.3-3.0 (m, 5 H), 2.38 (m, 1H), 2.0 (m, 5H). $^{31}$P NMR: 13.64. HRMS Calcd for $C_{33}H_{36}N_5O_5P$ (M+H)+614.2532. Found 614.2551.

EXAMPLE 110

(±)-9-[(1-Trityloxymethyl)(3-phosphonomethoxy)propyl]-6-N-phenylaminopurine (72j). Using the general procedure, 71j gives 72j (5.5%). $^1$H NMR (DMSO-$d_6$): δ 9.86 (br s, 1H), 8.48 (s, 1H), 8.28 (s, 1H), 7.40-7.00 (m, 20H), 5.20 (br s, 2H), 4.91 (m, 1H), 3.51 (m, 1H), 3.21 (m, 5H), 2.36 (m, 1H), 2.08 (m, 1H). 31P NMR: 13.27. HRMS Calcd for $C_{35}H_{34}N_5O_5P$ (M+H)$^+$ 636.2375. Found 636.2364.

EXAMPLE 111

(±)-9-[(1-Trityloxymethyl)(3-phosphonomethoxy)propyl]-6-cyclopentylaminopurine (72k). Using the general procedure, 71k gives 72k (10%) δ in ppm (DMSO-$d_6$): 8.26 (s, 1H), 8.05 (s, 1H), 7.58 (br s, 1H), 7.30-7.00 (m, 15H), 4.81 (m, 1H), 4.53 (m, 2H), 3.50-3.00 (m, 6H), 2.35 (m, 2H), 1.95 (m, 2H), 1.63 (m, 6H). $^{31}$P NMR: 13.91.

EXAMPLE 112

((±)-9-[(1-Trityloxymethyl)(3-phosphonomethoxy)propyl]-6-cyclopropylaminopurine (72l). Using the general procedure, 71l gives 72l (6.5%). $^1$H NMR (DMSO-$d_6$): δ 8.29 (s, 1H), 8.13 (1H), 7.80 (br s, 1H), 7.30-7.00 (m, 15H), 4.82 (m, 1H), 4.50 (br s, 2H), 3.46 (m, 3H), 3.30-3.10 (m, 4H), 2.35 (m, 1H, partially masked by DMSO-$d_6$), 2.05 (m, 1H), 0.70 (m, 4H). $^{31}$P NMR: 12.75. HRMS Calcd for $C_{32}H_{34}N_5O_5P$ (M+H)$^+$ 600.2373. Found 600.2378.

EXAMPLE 113

(±)-9-[(1-Trityloxymethyl)(3-phosphonomethoxy)propyl]-6-cyclobutylaminopurine (72m). Using the general procedure, 71m gives 72m (6.5%). $^1$H NMR (DMSO-d$_6$): δ 8.29 (s, 1H), 8.07 (s, 1H), 7.96 (br s, 1H), 7.30-7.00 (m, 15H), 5.00 (br s, 2H), 4.79 (m, 2H), 3.45 (m, 1H), 3.30 (m, 1H), 3.15 (m, 4H), 2.36-2.00 (m, 6H), 1.66 (m, 2H), $^{31}$P NMR: 12.94. HRMS Calcd for C$_{33}$H$_{36}$N$_5$O$_5$P (M+H)$^+$ 614.2532. Found 614.2538.

General Procedure for the Conversion of 72a-m to 73a-m:

A solution of 72a-m in DMF (10 mL/mmol) is treated with triethylamine (12 mL/mmol) followed by chloromethyl pivalate or chloromethyl-2-propylcarbonate (25 eq.) and stirred for 2 days at room temperature. The mixture is then diluted with ethyl acetate and washed with water and the organic layer is dried over MgSO$_4$. After filtration, the filtrate is concentrated and the residue purified on a silica gel column using chloroform:methanol (100:0 to 95:5) as eluent to give diprotected prodrugs of phosphonic acids. The resultant prodrugs are taken in acetonitrile:0.2 M HCl (1:1, 10 mL/mmol) and stirred for 14 h at room temperature. The solution is then very carefully neutralized with Et$_3$N to pH 6.0, diluted with water, and is concentrated to remove most of the organic solvent. The residual material is again diluted with water and extracted with chloroform and the organic layer is dried over MgSO$_4$. After filtration, the filtrate is concentrated and the residue purified on a silica gel column using chloroform:methanol (1:0 to 9:1) as eluent to give the desired targets 73a-m as colorless oil.

EXAMPLE 114

(±)-9-[(1-Hydroxymethyl)(3-(di-isopropyloxycarbonyloxymethylphosphono)methoxy)propyl]-6-diethylaminopurine (73a). Using the general procedure, 72a gives 73a (46%). $^1$H NMR (DMSO-d$_6$): δ 8.16 (s, 1H), 8.10 (s, 1H), 5.56 (m, 4H), 5.04 (t, 1H, J=5.3 Hz), 4.80 (m, 2H), 4.58 (m, 1H), 4.10 (m, 4H), 3.83 (m, 3H), 3.66 (m, 1H), 3.45 (m, 1H), 3.30 (m, 1H partially masked by water in DMSO-d$_6$), 2.17 (m, 2H), 1.21 (m, 18H). $^{31}$P NMR: 22.83. MS (ES$^+$) 606.66 (M+H)$^+$. Anal. Calcd for C$_{24}$H$_{40}$N$_5$O$_{11}$P.0.25 H$_2$O: C, 47.25; H, 6.69; N, 11.47. Found: C, 47.10; H, 6.85; N, 11.28.

EXAMPLE 115

(±)-9-[(1-Hydroxymethyl)(3-(di-isopropyloxycarbonyloxymethylphosphono)methoxy)propyl]-6-N-methyl-N-ethylaminopurine (73b). Using the general procedure, 72b gives 73b (20%). $^1$H NMR (DMSO-d$_6$): δ 8.17 (s, 1H), 8.11 (s, 1H), 5.59 (m, 4H), 5.05 (t, 1H, J=5.4 Hz), 4.80 (m, 2H), 4.59 (m, 1H), 4.05 (m, 2H), 3.82 (m, 3H), 3.66 (m, 1H), 3.40 (m, 2H), 2.49 (s, 3H), partially masked by DMSO-d$_6$), 2.17 (m, 2H), 1.24 (m, 15H). $^{31}$P NMR: 22.80. MS (ES$^+$) 592.08 (M+H)$^+$. Anal. Calcd for C$_{23}$H$_{38}$N$_5$O$_{11}$P.0.5 H$_2$O: C, 45.99; H, 6.54; N, 11.66. Found: C, 46.22; H, 6.57; N, 11.36.

EXAMPLE 116

(±)-9-[(1-Hydroxymethyl)(3-(di-tert-butyloxycarbonylmethylphosphono)methoxy)propyl]-6-ethylaminopurine (73c). Using the general procedure, 72c gives 73c (31%). $^1$H NMR (DMSO-d$_6$): δ 8.14 (s, 1H), 8.08 (s, 1H), 7.71 (br s, 1H), 5.60 (m, 4H), 5.04 (t, 1H, J=5.4 Hz), 4.55 (m, 1H), 3.82 (, 3H), 3.70 (m, 1H), 3.48 (m, 3H), 3.29 (m, 1H partially masked by water peak in DMSO-d$_6$), 2.18 (m, 2H), 1.13 (m, 21H).$^{31}$P NMR: 22.87. MS (ES$^+$) 596.31 (M+Na)$^+$.

EXAMPLE 117

(±)-9-[(1-Hydroxymethyl)(3-(di-tert-butyloxycarbonylmethylphosphono)methoxy)propyl]-6-allylaminopurine (73d). Using the general procedure, 72d gives 73d (32%). $^1$H NMR (DMSO-d$_6$): δ 8.15 (s, 1H), 8.10 (s, 1H), 7.89 (br s, 1H), 5.93 (m, 1H), 5.59 (m, 4H), 5.14 (m, 1H), 5.05 (m, 2H), 4.56 (m, 1H), 4.10 (m, 2H), 3.82 (m, 3H), 3.69 (m, 1H), 3.45 (m, 1H), 3.29 (m, 1H), partially masked by water peak in DMSO-d$_6$), 2.19 (m, 2H), 1.17 (m, 18H). $^{31}$P NMR: 22.87. MS (ES$^+$) 608.33 (M+Na)$^+$. Anal. Calcd for C$_{25}$H$_{40}$N$_5$O$_9$P: C, 50.45; H, 6.76; N, 11.72. Found: C, 50.45; H, 7.14; N, 11.03.

EXAMPLE 118

(±)-9-[(1-Hydroxymethyl)(3-(di-isopropyloxycarbonyloxymethylphosphono)methoxy)propyl]-6-N-thiazolidinopurine (73e). Using the general procedure, 72e gives 73e (27%). $^1$H NMR (DMSO-d$_6$): δ 8.26 (s, 1H), 8.21 (s, 1H), 5.57 (m, 4H), 5.05 (m, 2H), 4.81 (m, 2H), 4.61 (m, 1H), 4.28 (m, 2H), 3.83 (m, 3H), 3.70 (m, 1H), 3.45 (m, 1H), 3.29 (m, 2H partially masked by water peak in DMSO-d$_6$), 3.12 (m, 2H), 2.20 (m, 2H), 1.22 (m, 12H). $^{31}$P NMR: 22.80. MS (ES$^+$) 622.08 (M+H)$^+$. Anal. Calcd for C$_{23}$H$_{36}$N$_5$O$_{11}$PS.0.5 H$_2$O: C, 43.80; H, 5.91; N, 11.10. Found: C, 44.58; H, 6.10; N, 10.67.

EXAMPLE 119

(±)-9-[(1-Hydroxymethyl)(3-(di-isopropyloxycarbonyloxymethylphosphono)methoxy)propyl]-6-N-azetidinopurine (73f). Using the general procedure, 72f gives 73f (24%). $^1$H NMR (DMSO-d$_6$): δ 8.15 (s, 1H), 8.09 (s, 1H), 5.58 (m, 4H), 5.04 (t, 1H, J=5.4 Hz), 4.81 (m, 2H), 4.56 (m, 1H), 4.33 (m, 4H), 3.83 (m, 3H), 3.70 (m, 1H), 3.43 (m, 1H), 3.27 (m, 1H partially masked by water in DMSO-d$_6$), 2.42 (m, 2H), 2.16 (m, 2H), 1.23 (m, 12H). $^{31}$P NMR: 22.79. MS (ES$^+$) 590.04 (M+H)$^+$. Anal. Calcd for C$_{23}$H$_{36}$N$_5$O$_{11}$P.0.75 H$_2$O: C, 45.80; H, 6.26; N, 11.61. Found: C, 45.96; H, 6.44; N, 11.25.

EXAMPLE 120

(±)-9-[(1-Hydroxymethyl)(3-(di-isopropyloxycarbonyloxymethylphosphono)methoxy)propyl]-6-N-piperidinopurine (73g). Using the general procedure, 72g gives 73g (43%). $^1$H NMR (DMSO-d$_6$): δ 8.16 (s, 1H), 8.11 (s, 1H), 5.57 (m, 4H), 5.04 (t, 1H, J=5.4 Hz), 4.81 (m, 2H), 4.59 (m, 1H), 4.19 (m, 4H), 3.83 (m, 3H), 3.68 (m, 1H), 3.43 (m, 1H), 3.29 (m, 1H partially masked by water in DMSO-d$_6$), 2.19 (m, 2H), 1.70-1.30 (m, 6H), 1.23 (m, 12H). $^{31}$P NMR: 22.81. MS (ES$^+$) 618.34 (M+H)$^+$. Anal. Calcd for C$_{25}$H$_{40}$N$_5$O$_{11}$P.0.75 H$_2$O: C, 47.57; H, 6.62; N, 11.09. Found: C, 47.86; H, 6.56; N, 10.62.

EXAMPLE 121

(±)-9-[(1-Hydroxymethyl)(3-(di-isopropyloxycarbonyloxymethylphosphono)methoxy)propyl]-6-N-morpholinopurine (73h). Using the general procedure, 72h gives 73h (18%). $^1$H NMR (DMSO-d$_6$): δ 8.22 (s, 1H), 8.17 (s, 1H), 5.57 (m, 4H), 5.04 (t, 1H, J=5.3 Hz), 4.81 (m, 2H), 4.60 (m, 1H), 4.19 (m, 4H), 3.83 (m, 3H), 3.71 (m, 5H), 3.43 (m, 1H), 3.29 (m, 1H partially masked by water in DMSO-d$_6$), 2.18 (m, 2H), 1.23 (m, 12H). $^{31}$P NMR: 22.79. MS (ES$^+$) 620.29

(M+H)⁺. Anal. Calcd for $C_{24}H_{38}N_5O_{12}P \cdot 0.5\ H_2O$: C, 45.85; H, 6.25; N, 11.14. Found: C, 46.05; H, 6.21; N, 10.42.

EXAMPLE 122

(±)-9-[(1-Hydroxymethyl)(3-(di-isopropyloxycarbonyloxymethylphosphono)methoxy)propyl]-6-N-pyrrolidinopurine (73i). Using the general procedure, 72i gives 73i (28%). ¹H NMR (DMSO-d₆): δ 8.16 (s, 1H), 8.08 (s, 1H), 5.58 (m, 4H), 5.05 (t, 1H, J=5.4 Hz), 4.81 (m, 2H), 4.58 (m, 1H), 4.05 (m, 2H), 3.83 (m, 3H), 3.67 (m, 3H), 3.43 (1H), 3.28 (m, 1H partially masked by water peak in DMSO-d₆), 2.19 (m, 2H), 1.94 (m, 4H), 1.22 (m, 12H). ³¹P NMR: 22.78. MS (ES⁺) 604.29 (M+H)⁺. Anal. Calcd for $C_{24}H_{38}N_5O_{11}P \cdot 0.5\ CHCl_3$: C, 44.99; H, 5.94; N, 10.75. Found: C, 45.09; H, 6.03; N, 10.16.

EXAMPLE 123

(±)-9-[(1-Hydroxymethyl)(3-(di-isopropyloxycarbonyloxymethylphosphono)methoxy)propyl]-6-N-phenylaminopurine (73j). Using the general procedure, 72j gives 73j (31%). ¹H NMR (DMSO-d₆): δ 9.84 (br s, 1H), 8.32 (s, 1H), 8.30 (s, 1H), 7.94 (m, 2H), 7.31 (m, 2H), 7.02 (m, 1H), 5.58 (m, 4H), 5.07 (t, 1H, J=5.3 Hz), 4.80 (m, 2H), 4.63 (m, 1H), 3.84 (m, 3H), 3.73 (m, 1H), 3.46 (m, 1H), 3.29 (m, 1H partially masked by water peak in DMSO-d₆), 2.21 (m, 2H), 1.21 (m, 12H). ³¹P NMR: 22.81. MS (ES⁺) 626.23 (M+H)⁺. Anal. Calcd for $C_{26}H_{36}N_5O_{11}P \cdot H_2O$: C, 48.52; H, 5.95; N, 10.88. Found: C, 48.66; H, 5.89; N, 10.39.

EXAMPLE 124

(±)-9-[(1-Hydroxymethyl)(3-(di-tert-butyloxycarbonylmethylphosphono)methoxy)propyl]-6-cyclopentylaminopurine (73k). Using the general procedure, 72k gives 73k (45%). ¹H NMR (DMSO-d₆): δ 8.14 (s, 1H), 8.08 (s, 1H), 7.60 (br s, 1H), 5.58 (m, 4H), 5.04 (t, 1H, J=5.4 Hz), 4.54 (m, 2H), 3.78 (m, 3H), 3.68 (m, 1H), 3.42 (m, 1H), 3.29 (m, 1H partially masked by water in DMSO-d₆), 2.17 (m, 2H), 1.90 (m, 2H), 1.80-1.50 (m, 6H), 1.12 (m, 18H). ³¹P NMR: 22.88. MS (ES⁺) 614.44 (M+H)⁺. Anal. Calcd for $C_{27}H_{44}N_5O_9P$: C, 50.53; H, 7.04; N, 10.83. Found: C, 50.64; H, 7.12; N, 10.44.

EXAMPLE 125

(±)-9-[(1-Hydroxymethyl)(3-(di-isopropyloxycarbonyloxymethylphosphono)methoxy)propyl]-6-cyclopropylaminopurine (73l). Using the general procedure, 72l gives 73l (7%). ¹H NMR (CDCl₃): δ 8.38 (s, 1H), 7.89 (s, 1H), 6.20 (br s, 1H), 5.71 (m, 5H), 4.92 (m, 2H), 4.71 (m, 1H), 4.08 (m, 2H), 3.84 (m, 2H), 3.65 (m, 1H), 3.23 (m, 1H), 3.02 (br s, 1H), 2.27 (m, 2H), 1.29 (m, 12H), 0.94 (m, 2H), 0.66 (m, 2H). ³¹P NMR: 22.69. MS (ES⁺) 590.19 (M+H)⁺.

EXAMPLE 126

(±)-9-[(1-Hydroxymethyl)(3-(di-isopropyloxycarbonyloxymethylphosphono)methoxy)propyl]-6-cyclobutylaminopurine (73m). Using the general procedure, 72m gives 73m (29%). ¹H NMR (DMSO-d₆): δ 8.14 (s, 1H), 8.10 (s, 1H), 7.95 (br s, 1H), 5.58 (m, 4H), 5.04 (t, 1H, J=5.3 Hz), 4.80 (m, 2H), 4.60 (m, 2H), 3.84 (m, 3H), 3.68 (m, 1H), 3.44 (m, 1H), 3.27 (m, 1H partially masked by water peak in DMSO-d₆), 2.15 (m, 6H), 1.64 (m, 2H), 1.24 (m, 12H). ³¹P NMR: 22.81. MS (ES⁺) 604.13 (M+H)⁺. Anal. Calcd for $C_{24}H_{38}N_5O_{11}P \cdot 0.75\ H_2O$: C, 46.71; H, 6.45; N, 11.34. Found: C, 47.14; H, 6.65; N, 11.04.

EXAMPLE 127

(±)-9-[(1-Hydroxymethyl)(3-(di-tert-butyloxycarbonylmethylphosphono)methoxy)propyl]-6-phenylpurine (76a). A solution of compound 70 (10.0 mmol), phenylboronic acid (15.0 mmol), sodium bicarbonate (30.0 mmol) and bis(triphenylphosphine)palladium(II)dichloride (1.5 mmol) in DME:water (9:1, 100 mL) is heated at 80° C. for 48 h. After adding water (100 mL), the reaction mixture is extracted with ethyl acetate (2×100 mL). The combined organic extracts are washed with water (100 mL), brine (100 mL) and dried (MgSO₄). After filtration, the filtrate is concentrated and the residue is purified on a column of silica gel using ethyl acetate and hexanes mixture as eluent. The fractions containing the product are pooled together and concentrated to give the desired product in 67% yield.

The product obtained above is further processed to remove tert-butyldimethylsilyl group; protect hydroxyl with trityl; remove pivaloyl; generate phosphonic acid derivative; deprotect phoshonate; make appropriate prodrug of phosphonic acid; and deprotect trityl according to the procedures already described in afore mentioned examples. ¹H NMR (DMSO-d₆): δ 8.90 (s, 1H), 8.83-8.77 (m, 2H), 8.63 (s, 1H), 7.60-7.50 (m, 3H), 5.58-5.47 (m, 4H), 5.05 (t, J=5.6 Hz, 1H), 4.80-4.66 (m, 1H), 3.94-3.83 (m, 1H), 3.76 (d, J=7.7 Hz, 2H), 3.77-3.67 (m, 1H), 3.51-3.41 (m, 1H), 3.38-3.28 (m, 1H), 2.35-2.10 (m, 2H), 1.072 (s, 9H), 1.067 (s, 9H); ³¹P NMR (DMSO-d₆): 22.87 (s, 1P); Anal. Calcd. for $C_{28}H_{39}N_4O_9P \cdot 0.2\ H_2O$: C, 55.11; H, 6.50; N, 9.18; Found: C, 55.07; H, 6.64; N, 9.04; MS (ES⁺): 607.35 (M+H)⁺.

EXAMPLE 128

(±)-9-[(1-Hydroxymethyl)(3-(di-tert-butyloxycarbonylmethylphosphono)methoxy)propyl]-6-(3-thiophenyl)purine (76b).

A solution of compound 70 (10.0 mmol), 3-thiopheneboronic acid (15.0 mmol), sodium bicarbonate (30.0 mmol) and bis(triphenylphosphine)palladium(II)dichloride (1.5 mmol) in DME:water (9:1, 100 mL) is heated at 80° C. for 48 h. After adding water (100 mL), the reaction mixture is extracted with ethyl acetate (2×100 mL). The combined organic extracts are washed with water (100 mL), brine (100 mL) and dried (MgSO₄). After filtration, the filtrate is concentrated and the residue is purified on a column of silica gel using ethyl acetate and hexanes mixture as eluent. The fractions containing the product are pooled together and concentrated to give the desired product in 84% yield.

The product obtained above is further processed to remove tert-butyldimethylsilyl group; protect hydroxyl with trityl; remove pivaloyl; generate phosphonic acid derivative; deprotect phoshonate; make appropriate prodrug of phosphonic acid; and deprotect trityl according to the procedures already described in afore mentioned examples. ¹H NMR (DMSO-d₆): δ 8.92 (dd, J=3.1, 1.1 Hz, 1H), 8.83 (s, 1H), 8.61 (s, 1H), 8.21 (dd, J=5.3, 1.1 Hz, 1H), 7.71 (dd, J=5.3, 3.1 Hz, 1H), 5.58-5.50 (m, 4H), 5.06 (t, J=5.6 Hz, 1H), 4.79-4.65 (m, 1H), 3.94-3.82 (m, 1H), 3.77 (d, J=7.7 Hz, 2H), 3.78-3.66 (m, 1H), 3.52-3.26 (m, 2H), 2.56-2.10 (m, 2H), 1.09 (s, 9H), 1.08 (s, 9H); ³¹P NMR (DMSO-d₆): 22.86 (s, 1P); Anal. Calcd. for $C_{26}H_{37}N_4O_9PS$: C, 50.97; H, 6.09; N, 9.15; Found: C, 50.42; H, 6.19; N, 8.87; MS (ES⁺): 613.34 (M+H)⁺.

EXAMPLE 129

(±)-9-[(1-Hydroxyethyl)(3-(di-tert-butyloxycarbonylmethylphosphono)methoxy)ethyl]-6-phenylpurine (79a). A solution of compound 70 (10.0 mmol), phenylboronic acid (15.0 mmol), sodium bicarbonate (30.0 mmol) and bis(triphenylphosphine)palladium(II) dichloride (1.5 mmol) in DME:water (9:1, 100 mL) is heated at 80° C. for 48 h. After adding water (100 mL), the reaction mixture is extracted with ethyl acetate (2×100 mL). The combined organic extracts are washed with water (100 mL), brine (100 mL) and dried (MgSO$_4$). After filtration, the filtrate is concentrated and the residue is purified on a column of silica gel using ethyl acetate and hexanes mixture as eluent. The fractions containing the product are pooled together and concentrated to give the desired product in 67% yield.

The product obtained above is further processed to deprotect pivaloyl; protect hydroxyl with trityl; remove tert-butoxydimethylsilyl; generate phosphonic acid derivative; deprotect phoshonate; make appropriate prodrug of phosphonic acid; and deprotect trityl according to the procedures already described in afore mentioned examples. $^1$H NMR (DMSO-d$_6$): δ 8.91 (s, 1H), 8.81-8.76 (m, 2H), 8.64 (s, 1H), 7.59-7.50 (m, 3H), 5.45-5.37 (m, 4H), 5.08-4.92 (m, 1H), 4.57 (t, J=4.9 Hz, 1H), 4.15-4.06 (m, 1H), 3.97-3.81 (m, 3H), 3.40-3.15 (m, 2H), 2.26-2.12 (m, 1H), 2.10-1.95 (m, 1H), 1.029 (s, 9H), 1.026 (s, 9H); $^{31}$P NMR (DMSO-d$_6$): 22.07 (s, 1P); Anal. Calcd. for C$_{28}$H$_{39}$N$_4$O$_9$P.0.75 H$_2$O: C, 54.23; H, 6.58; N, 9.03; Found: C, 54.09; H, 6.53; N, 8.82; MS (ES$^+$): 607.37 (M+H)$^+$.

EXAMPLE 130

(±)-9-[(1-Hydroxyethyl)(3-(di-tert-butyloxycarbonylmethylphosphono)methoxy)ethyl]-6-(3-thiophenyl)purine (79b). A solution of compound 70 (10.0 mmol), 3-thipheneboronic acid (15.0 mmol), sodium bicarbonate (30.0 mmol) and bis(triphenylphosphine)palladium(II) dichloride (1.5 mmol) in DME:water (9:1, 100 mL) is heated at 80° C. for 48 h. After adding water (100 mL), the reaction mixture is extracted with ethyl acetate (2×100 mL). The combined organic extracts are washed with water (100 mL), brine (100 mL) and dried (MgSO$_4$). After filtration, the filtrate is concentrated and the residue is purified on a column of silica gel using ethyl acetate and hexanes mixture as eluent. The fractions containing the product are pooled together and concentrated to give the desired product in 67% yield.

The product obtained above is further processed to deprotect pivaloyl; protect hydroxyl with trityl; remove tert-butoxydimethylsilyl; generate phosphonic acid derivative; deprotect phoshonate; make appropriate prodrug of phosphonic acid; and deprotect trityl according to the procedures already described in afore mentioned examples. $^1$H NMR (DMSO-d$_6$): δ 8.95 (dd, J=3.0, 1.1 Hz, 1H), 8.88 (s, 1H), 8.67 (s, 1H), 8.24 (dd, J=5.1, 1.4 Hz, 1H), 7.75 (dd, J=5.1, 3.0 Hz, 1H), 5.52-5.42 (m, 4H), 5.08-4.96 (m, 1H), 4.62 (t, J=4.8 Hz, 1H), 4.20-4.10 (m, 1H), 4.00-3.84 (m, 3H), 3.45-3.15 (m, 2H), 2.30-2.15 (m, 1H), 2.15-2.00 (m, 1H), 1.089 (s, 9H), 1.085 (s, 9H); $^{31}$P NMR (DMSO-d$_6$): 22.06 (s, 2P); Anal. Calcd. for C$_{26}$H$_{37}$N$_4$O$_9$PS.0.2 H$_2$O: C, 50.67; H, 6.11; N, 9.09; Found: C, 50.79; H, 6.22; N, 8.96; MS (ES$^+$): 613.32 (M+H)$^+$.

HCV NS5B Polymerase Assay

Antiviral activity of the test compounds is assessed (Okuse et al., Antiviral Res. 2005, 65, 23-34) in the stably HCV RNA-replicating cell line, AVA5, derived by transfection of the human hepatoblastoma cell line, Huh7 (Blight et al., Sci. 2000, 290, 1972). Compounds are added to dividing cultures once daily for three days. Media is changed with each addition of compound. Cultures generally start the assay at 30-50% confluence and reach confluence during the last day of treatment. Intracellular HCV RNA levels and cytotoxicity are assessed 24 hours after the last dose of compound.

Triplicate cultures for HCV RNA levels (on 48-well and 96-well plates) and cytotoxicity (on 96-well plates) are used. A total of six untreated control cultures, and triplicate cultures treated with α-interferon and ribavirin serve as positive antiviral and toxicity controls.

Intracellular HCV RNA levels are measured using a conventional blot hybridization method in which HCV RNA levels are normalized to the levels of B-actin RNA in each individual culture (Okuse et al., Antivir. Res. 2005, 65, 23-34). Cytotoxicity is measured using a neutral red dye uptake assay (Korba and Gerin, Antivir. Res. 1992, 19, 55). HCV RNA levels in the treated cultures are expressed as a percentage of the mean levels of RNA detected in untreated cultures.

TABLE 1

Antiviral Activity (HCV Replicon Assay)

| Compound No. | % Inhibition at 10 μM |
|---|---|
| 34d | 60 |
| 34e | 41 |
| 34h | 35 |
| 56f | 62 |
| 73k | 36 |
| 76a | 35 |
| 76b | 18 |
| 79a | 48 |

Formulation

The compounds of the present disclosure can be administered by any conventional means available for use in conjunction with pharmaceuticals, either as individual therapeutic agents or in a combination of therapeutic agents. Example of these further therapeutic are interferon (IFN), interferon α-2a, interferon α-2b, consensus interferon (CIFN), ribavirin, amantadine, rimantadine, interleukine-12, ursodeoxycholic acid (UDCA), glycyrrhizin, and silybum marianum. They can be administered alone, but generally administered with a pharmaceutical carrier selected on the basis of the chosen route of administration and standard pharmaceutical practice.

The pharmaceutically acceptable carriers described herein, for example, vehicles, adjuvants, excipients, or diluents, are well-known to those who are skilled in the art. Typically, the pharmaceutically acceptable carrier is chemically inert to the active compounds and has no detrimental side effects or toxicity under the conditions of use. The pharmaceutically acceptable carriers can include polymers and polymer matrices.

The compounds of this disclosure can be administered by any conventional method available for use in conjunction with pharmaceuticals, either as individual therapeutic agents or in a combination of therapeutic agents.

The dosage administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. A daily dosage of active ingredient can be expected to be about 0.001 to 1000 milligrams (mg) per kilogram (kg) of body weight, with the preferred dose being 0.1 to about 30 mg/kg.

Dosage forms (compositions suitable for administration) contain from about 1 mg to about 500 mg of active ingredient per unit. In these pharmaceutical compositions, the active ingredient will ordinarily be present in an amount of about 0.5-95% weight based on the total weight of the composition.

The active ingredient can be administered orally in solid dosage forms, such as capsules, tablets, and powders, or in liquid dosage forms, such as elixirs, syrups and suspensions. It can also be administered parenterally, in sterile liquid dosage forms. The active ingredient can also be administered intranasally (nose drops) or by inhalation of a drug powder mist. Other dosage forms are potentially possible such as administration transdermally, via patch mechanism or ointment.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, propylene glycol, glycerin, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of the following: lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acadia, emulsions, and gels containing, in addition to the active ingredient, such carriers as are known in the art.

The compounds of the present disclosure, alone or in combination with other suitable components, can be made into aerosol formulations to be administered via inhalation. These aerosol formulations can be placed into pressurized acceptable propellants, such as dichlorodifluoromethane, propane, and nitrogen. They also may be formulated as pharmaceuticals for non-pressured preparations, such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol such as poly(ethyleneglycol) 400, glycerol ketals, such as 2,2-dimethyl-1,3-dioxolane-4-methanol, ethers, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyldialkylammonium halides, and alkylpyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene polypropylene copolymers, (d) amphoteric detergents such as, for example, alkyl β-aminopropionates, and 2-alkylimidazoline quaternary ammonium salts, and (e) mixtures thereof.

The parenteral formulations typically contain from about 0.5% to about 25% by weight of the active ingredient in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol.

Pharmaceutically acceptable excipients are also well-known to those who are skilled in the art. The choice of excipient will be determined in part by the particular compound, as well as by the particular method used to administer the composition. Accordingly, there is a wide variety of suitable formulations of the pharmaceutical composition of the present invention. The following methods and excipients are merely exemplary and are in no way limiting. The pharmaceutically acceptable excipients preferably do not interfere with the action of the active ingredients and do not cause adverse side-effects. Suitable carriers and excipients include solvents such as water, alcohol, and propylene glycol, solid absorbents and diluents, surface active agents, suspending agent, tableting binders, lubricants, flavors, and coloring agents.

The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets. The requirements for effective pharmaceutical carriers for injectable compositions are well known to those of ordinary skill in the art. See *Pharmaceutics and Pharmacy Practice,* J.B. Lippincott Co., Philadelphia, Pa., Banker and Chalmers, Eds., 238-250 (1982) and *ASHP Handbook on Injectable Drugs,* Toissel, 4th ed., 622-630 (1986).

Formulations suitable for topical administration include lozenges comprising the active ingredient in a flavor, usually sucrose and acacia or tragacanth; pastilles comprising the active ingredient in an inert base, such as gelatin and glycerin, or sucrose and acacia; and mouthwashes comprising the active ingredient in a suitable liquid carrier; as well as creams, emulsions, and gels containing, in addition to the active ingredient, such carriers as are known in the art.

Additionally, formulations suitable for rectal administration may be presented as suppositories by mixing with a variety of bases such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

Suitable pharmaceutical carriers are described in Remington's Pharmaceutical Sciences, Mack Publishing Company, a standard reference text in this field.

The dose administered to an animal, particularly a human, in the context of the present invention should be sufficient to effect a therapeutic response in the animal over a reasonable time frame. One skilled in the art will recognize that dosage will depend upon a variety of factors including a condition of the animal, the body weight of the animal.

A suitable dose is that which will result in a concentration of the active agent in a patient which is known to effect the desired response. The size of the dose also will be determined by the route, timing and frequency of administration as well as the existence, nature, and extend of any adverse side effects that might accompany the administration of the compound and the desired physiological effect.

Useful pharmaceutical dosage forms for administration of the compounds according to the present invention can be illustrated as follows:

Hard Shell Capsules

A large number of unit capsules are prepared by filling standard two-piece hard gelatine capsules each with 100 mg of powdered active ingredient, 150 mg of lactose, 50 mg of cellulose and 6 mg of magnesium stearate.

Soft Gelatin Capsules

A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.

Tablets

A large number of tablets are prepared by conventional procedures so that the dosage unit was 100 mg of active ingredient, 0.2 mg. of colloidal silicon dioxide, 5 mg of magnesium stearate, 275 mg of microcrystalline cellulose, 11 mg. of starch, and 98.8 mg of lactose. Appropriate aqueous and non-aqueous coatings may be applied to increase palatability, improve elegance and stability or delay absorption.

Immediate Release Tablets/Capsules

These are solid oral dosage forms made by conventional and novel processes. These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

Moreover, the compounds of the present disclosure can be administered in the form of nose drops, or metered dose and a nasal or buccal inhaler. The drug is delivered from a nasal solution as a fine mist or from a powder as an aerosol.

The foregoing description of the disclosure illustrates and describes the present disclosure. Additionally, the disclosure shows and describes only the preferred embodiments of the invention but, as mentioned above, it is to be understood that the invention is capable of use in various other combinations, modifications, and environments and is capable of changes or modifications within the scope of the inventive concept as expressed herein, commensurate with the above teachings and/or the skill or knowledge of the relevant art. The embodiments described hereinabove are further intended to explain best modes known of practicing the disclosure and to enable others skilled in the art to utilize the invention in such, or other, embodiments and with the various modifications required by the particular applications or uses of the disclosure. Accordingly, the description is not intended to limit the invention to the form disclosed herein. Also, it is intended that the appended claims be construed to include alternative embodiments.

All publications and patent applications cited in this specification are herein incorporated by reference, and for any and all purposes, as if each individual publication or patent application were specifically and individually indicated to be incorporated by reference.

What is claimed is:

1. A compound represented by the formula:

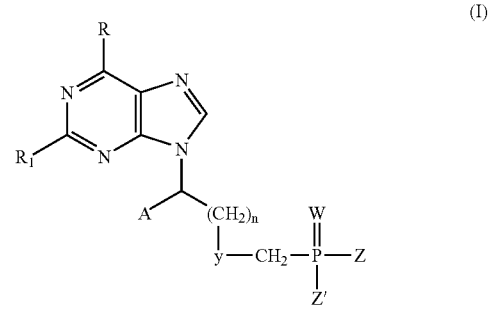

wherein A is selected from the group consisting of $(CH_2)_nR_2$, $-CH=CH_2$, $CH_2-CH=CH_2$, $O(CH_2)_nR_2$, $CH(OH)$ $CH_3$, $CH(OH)CH_2OH$, $CH_2-CH(OH)CH_3$, and $CH_2CH(OH)CH_2OH$, $CH(OH)CH(OH)CH_3$, R is selected from the group consisting of, aryl, substituted aryl, heterocycle, $NR_3R_4$, and $OR_3$, provided that both R and $R_1$ cannot both be $OR_3$, $R_1$ is selected from the group consisting of H, Cl, Br, I, aryl, substituted aryl, heterocycle, $NR_3R_4$, $OR_3$, and $SR_3$, $R_2$ is selected from the group consisting of H, OH, F, $N_3$, $NH_2$, $CO_2H$, SH, alkyl, substituted alkyl, S-alkyl, O-acyl, $CONH_2$, and CONH-alkyl, n is an integer of 1-3, y is selected from the group consisting of O, S and NH, W is selected from the group consisting of O and S, Z and Z' are individually selected from the group consisting of $O(CH_2)_m-O-(CH_2)_xCH_3$, $NH-CH(alkyl)CO_2R_3$, alkyl, substituted alkyl, $OCH_2CH_2S-C(O)CH_3$, $OCH_2CH_2S-C(O)CH(CH_3)_2$, $OCH_2CH_2S-C(O)C(CH_3)_3$, $OCH_2CH_2-SC(O)aryl$, $OCH_2CH_2-S-S-OCH_2CH_2OH$, $OCH_2OC(O)C(CH_3)_3$, $OCH_2-O-C(O)OCH(CH_3)_2$, and $OCH_2-O-C(O)CH(CH_3)_2$, $R_3$ and $R_4$ are individually selected from the group consisting of H, alkyl, substituted alkyl, aryl, and substituted aryl; additionally, $R_3$ and $R_4$ of $NR_3R_4$ can form a monocyclic ring of 4-7 atoms with N or optionally a further heteroatom in the ring, m is an integer of 1-3, x is an integer of 0-19;

and pharmaceutically acceptable salts thereof and prodrugs thereof.

2. The compound according to claim 1 represented by the formula:

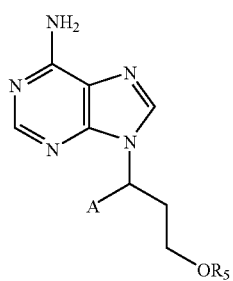

(II)

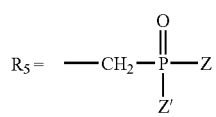

A is selected from the group consisting of $CH_2OH$, $CH_2OCH_3$, $CH_2N_3$, $CH_2NH_2$, $CH(OH)CH_3$, $CH_2F$, and $CH_2CH_2OH$, Z and Z' individually is selected from the group consisting of $O(CH_2)_m-O-(CH_2)_xCH_3$, $NH-CH(alkyl)CO_2R_3$, alkyl, substituted alkyl, $OCH_2CH_2S-C(O)CH_3$, $OCH_2CH_2S-C(O)CH(CH_3)_2$, $OCH_2CH_2S-C(O)C(CH_3)_3$, $OCH_2CH_2-SC(O)$ aryl, $OCH_2CH_2-S-S-OCH_2CH_2OH$, $OCH_2OC(O)C(CH_3)_3$, $OCH_2-O-C(O)OCH(CH_3)_2$, and $OCH_2-O-C(O)CH(CH_3)_2$, $R_3$ is selected from the group consisting of H, alkyl, substituted alkyl, aryl, and substituted aryl, m is an integer of 1-3, x is an integer of 0-19;

and pharmaceutically acceptable salts thereof and prodrugs thereof.

3. The compound according to claim 1 represented by the formula:

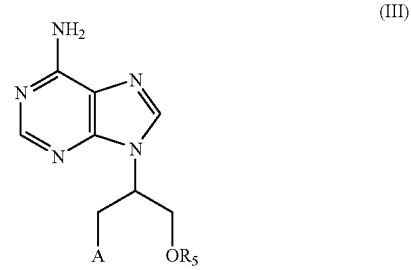

(III)

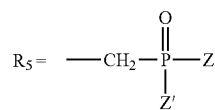

A is selected from the group consisting of $CH_2OH$, $CH_2N_3$, $CH_2NH_2$, $CH_2OCH_3$, $CH_3$, and $CH(OH)CH_3$, Z and Z' are individually selected from the group consisting of $O(CH_2)_m-O-(CH_2)_xCH_3$, $NH-CH(alkyl)CO_2R_3$, alkyl, substituted alkyl, $OCH_2CH_2S-C(O)CH_3$, $OCH_2CH_2S-C(O)CH(CH_3)_2$, $OCH_2CH_2S-C(O)C(CH_3)_3$, $OCH_2CH_2-SC(O)$ aryl, $OCH_2CH_2-S-S-OCH_2CH_2OH$, $OCH_2OC(O)C(CH_3)_3$, $OCH_2-O-C(O)OCH(CH_3)_2$, and $OCH_2-O-C(O)CH(CH_3)_2$, $R_3$ is selected from the group consisting of H, alkyl, substituted alkyl, aryl, and substituted aryl, m is an integer of 1-3, x is an integer of 0-19;

and pharmaceutically acceptable salts thereof and prodrugs thereof.

4. The compound according to claim 2 represented by the formula:

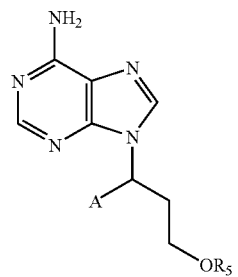

(IV)

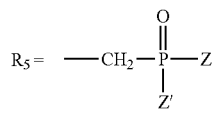

A is selected from the group consisting of CH$_2$OH, CH$_2$OCH$_3$, CH$_2$N$_3$, CH$_2$NH$_2$, CH(OH)CH$_3$, CH$_2$F, and CH$_2$CH$_2$OH, Z and Z' individually is selected from the group consisting of —O—CH$_2$OC(O)C(CH$_3$)$_3$, —O—CH$_2$OC(O)OCH(CH$_3$)$_2$;

and pharmaceutically acceptable salts thereof and prodrugs thereof.

5. The compound according to claim 3 represented by the formula:

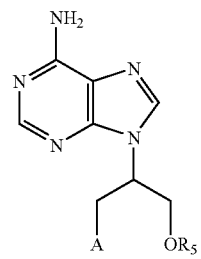

(V)

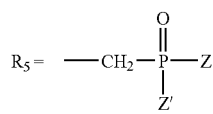

A is selected from the group consisting of CH$_2$OH, CH$_2$N$_3$, CH$_2$NH$_2$, CH$_2$OCH$_3$, CH$_3$, and CH(OH)CH$_3$ Z and Z' individually is selected from the group consisting of —O—CH$_2$—OC(O)C(CH$_3$)$_2$, and OCH$_2$OC(O)OCH(CH$_3$)$_2$;

and pharmaceutically acceptable salts thereof and prodrugs thereof.

6. The compound represented by the formula:

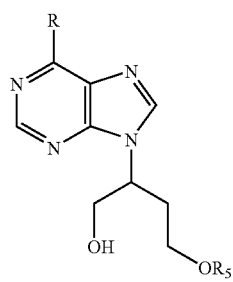

(VI)

-continued

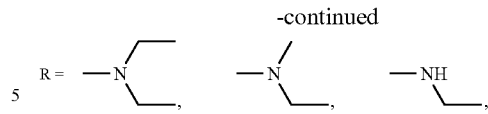

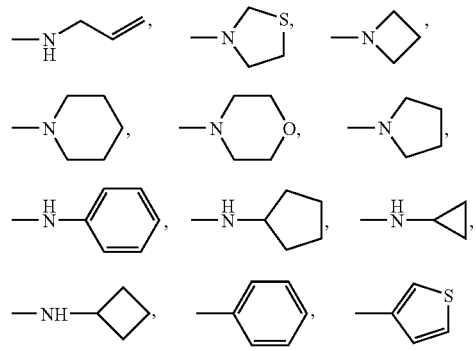

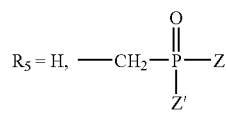

Z and Z' individually is selected from the group consisting of OR$_3$, OR$_1$, O(CH$_2$)$_m$—O—(CH$_2$)$_x$CH$_3$, NH—CH(alkyl)CO$_2$R$_3$, alkyl, substituted alkyl, OCH$_2$CH$_2$S—C(O)CH$_3$, OCH$_2$CH$_2$S—C(O)CH(CH$_3$)$_2$, OCH$_2$CH$_2$S—C(O)C(CH$_3$)$_3$, OCH$_2$CH$_2$—SC(O) aryl, OCH$_2$CH$_2$—S—S—OCH$_2$CH$_2$OH, OCH$_2$OC(O)C(CH$_3$)$_3$, OCH$_2$—O—C(O)OCH(CH$_3$)$_2$, and OCH$_2$—O—C(O)CH(CH$_3$)$_2$ R$_3$ and R$_4$ is selected from the group consisting of H, alkyl, substituted alkyl, aryl, and substituted aryl, m is an integer of 1-3, x is an integer of 0-19;

and pharmaceutically acceptable salts thereof and prodrugs thereof.

7. The compound according to claim 6 represented by the formula:

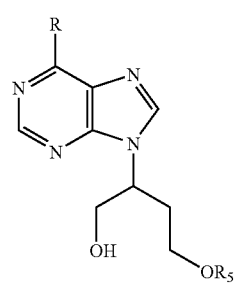

(VII)

-continued

R = 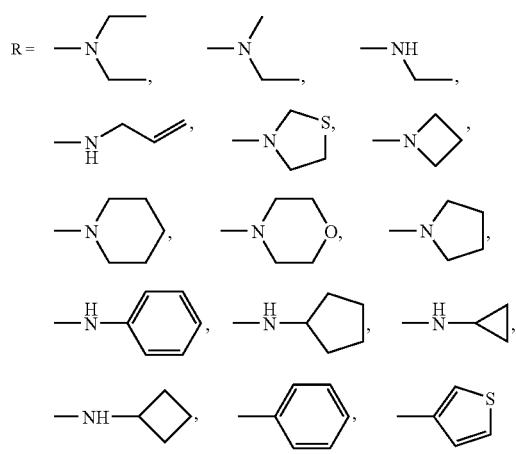

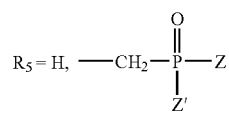

Z and Z' is selected from the group consisting of OH, —O—CH₂OC(O)C(CH₃)₃, and —OCH₂OC(O)OCH(CH₃)₂, and pharmaceutically acceptable salts thereof and prodrugs thereof.

8. The compound represented by the formula:

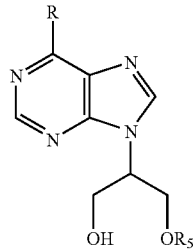

(VIII)

R = 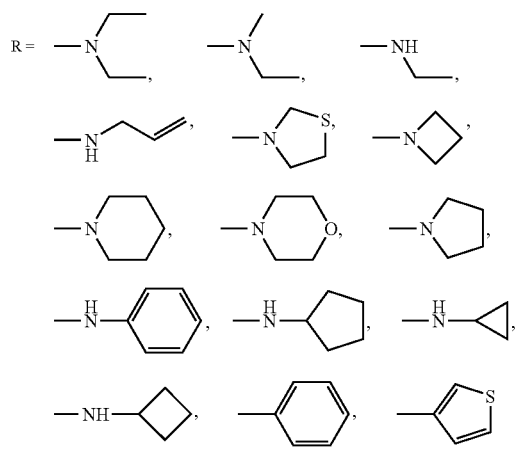

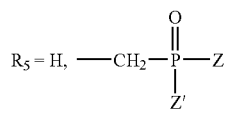

Z and Z' is selected from the group consisting of OH, —O—CH₂OC(O)C(CH₃)₃, and —OCH₂OC(O)OCH(CH₃)₂;

and pharmaceutically acceptable salts thereof and prodrugs thereof.

9. A pharmaceutical composition comprising a compound according to claim 1 and a pharmaceutically acceptable carrier.

10. A method for inhibiting HCV polymerase in a patient by administering to the patient at least one compound according to claim 1.

11. A method for treating a patient suffering from HCV which comprises administering to said patient an effective amount of at least one compound according to claim 1.

12. A method for inhibiting in a patient in need thereof a HCV viral polymerase which comprises administering to said patient an effective amount of at least one compound according to claim 1 and at least one further therapeutic agent from the group consisting of interferon (IFN), interferon α-2a, interferon α-2b, consensus interferon (CIFN), ribavirin, amantadine, rimantadine, interleukine-12, ursodeoxycholic acid (UDCA), and glycyrrhizin.

13. A method for treating a patient suffering from a HCV viral infection which comprises administering to the patient an effective amount of at least one compound according to claim 1 and at least one further therapeutic agent chosen from interferon (IFN), interferon α-2a, interferon α-2b, consensus interferon (CIFN), ribavirin, amantadine, rimantadine, interleukine-12, ursodeoxycholic acid (UDCA), and glycyrrhizin.

14. A pharmaceutical composition comprising a compound according to claim 3 and a pharmaceutically acceptable carrier.

15. A pharmaceutical composition comprising a compound according to claim 6 and a pharmaceutically acceptable carrier.

16. A pharmaceutical composition comprising a compound according to claim 8 and a pharmaceutically acceptable carrier.

* * * * *